(12) United States Patent
Meade et al.

(10) Patent No.: US 6,770,261 B2
(45) Date of Patent: Aug. 3, 2004

(54) MAGNETIC RESONANCE IMAGING AGENTS FOR THE DETECTION OF PHYSIOLOGICAL AGENTS

(75) Inventors: Thomas J. Meade, Altadena, CA (US); Scott Fraser, La Canada, CA (US)

(73) Assignee: Research Corporation Technologies, Tucson, AZ (US)

(*) Notice: Subject to any disclaimer, the term of this patent is extended or adjusted under 35 U.S.C. 154(b) by 0 days.

(21) Appl. No.: 09/866,512

(22) Filed: May 24, 2001

(65) Prior Publication Data

US 2003/0053954 A1 Mar. 20, 2003

Related U.S. Application Data

(63) Continuation-in-part of application No. 09/405,046, filed on Sep. 27, 1999, which is a continuation-in-part of application No. 09/134,072, filed on Aug. 13, 1998, now Pat. No. 5,980,862, which is a continuation of application No. 08/971,855, filed as application No. PCT/US96/08548 on Jun. 3, 1996, now abandoned, which is a continuation of application No. 08/486,968, filed on Jun. 7, 1995, now Pat. No. 5,707,605, which is a continuation of application No. 08/460,511, filed on Jun. 2, 1995, now abandoned.

(60) Provisional application No. 60/287,619, filed on May 26, 2000, and provisional application No. 60/063,328, filed on Oct. 27, 1997.

(51) Int. Cl.[7] .................................................. A61B 5/55
(52) U.S. Cl. .................... 424/9.34; 424/1.11; 424/1.65; 424/9.1; 424/9.3; 424/9.323; 424/1.69; 424/9.36; 530/300; 530/329
(58) Field of Search .............................. 424/1.11, 1.65, 424/1.69, 9.1, 9.3, 9.322, 9.323, 9.34, 9.36; 530/300, 329

(56) References Cited

U.S. PATENT DOCUMENTS

| | | |
|---|---|---|
| 4,637,988 A | 1/1987 | Hinshaw et al. |
| 4,647,447 A | 3/1987 | Gries et al. |
| 4,678,667 A | 7/1987 | Meares et al. |
| 4,822,594 A | 4/1989 | Gibby |
| 4,837,169 A | 6/1989 | Toner |
| 4,877,872 A | 10/1989 | Morgan et al. |
| 4,885,363 A | 12/1989 | Tweedle et al. |
| 5,087,440 A | 2/1992 | Cacheris et al. |
| 5,095,099 A | 3/1992 | Parkinson et al. |
| 5,133,956 A | 7/1992 | Garlich et al. |
| 5,155,215 A | 10/1992 | Ranney |
| 5,188,816 A | 2/1993 | Sherry et al. |
| 5,219,553 A | 6/1993 | Kraft et al. |
| 5,230,883 A | 7/1993 | Kornguth et al. |
| 5,256,395 A | 10/1993 | Barbet et al. |
| 5,262,532 A | 11/1993 | Tweedle et al. |
| 5,292,414 A | 3/1994 | Sessler et al. |
| 5,310,539 A | 5/1994 | Williams |
| 5,322,681 A | 6/1994 | Klaveness |
| 5,332,567 A | 7/1994 | Goldenberg |
| 5,338,532 A | 8/1994 | Tomalia et al. |
| 5,358,704 A | 10/1994 | Desreux et al. |
| 5,407,657 A | 4/1995 | Unger et al. |
| 5,419,893 A | 5/1995 | Berg et al. |
| 5,446,145 A | 8/1995 | Love et al. |
| 5,466,438 A | 11/1995 | Unger et al. |
| 5,466,439 A | 11/1995 | Gibby et al. |
| 5,531,978 A | 7/1996 | Berg et al. |
| 5,554,748 A | 9/1996 | Sieving et al. |
| 5,622,821 A | 4/1997 | Selvin et al. |
| 5,707,605 A | 1/1998 | Meade et al. |
| 5,914,095 A | 6/1999 | Watson |
| 5,955,605 A | 9/1999 | Axworthy et al. |
| 5,980,862 A | 11/1999 | Meade et al. |

FOREIGN PATENT DOCUMENTS

| | | |
|---|---|---|
| CA | 2139374 A1 | 7/1995 |
| CA | 2182686 A1 | 8/1995 |
| WO | WO 90/12050 A1 | 10/1990 |
| WO | WO 92/19264 A1 | 11/1992 |
| WO | WO 95/27705 A1 | 10/1995 |
| WO | WO 95/28966 A1 | 11/1995 |
| WO | WO 95/31444 A1 | 11/1995 |
| WO | WO 95/32741 A1 | 12/1995 |
| WO | WO 96/05167 A1 | 2/1996 |
| WO | WO 96/23526 A2 | 8/1996 |
| WO | WO 96/38184 A2 | 12/1996 |
| WO | WO 97/21431 A1 | 6/1997 |
| WO | WO 97/32862 A1 | 9/1997 |
| WO | WO 97/36619 A2 | 10/1997 |
| WO | WO 99/21592 A1 | 5/1999 |

OTHER PUBLICATIONS

Jacobs and Fraser, "Magnetic Resonance Microscopy of Embryonic Cell Lineages and Movements," *Science*, 263:681–684 (1994).

Staubli and Meade, "The Design and Synthesis of Fluorescently Detectable Magnetic Resonance imaging Agents for Embryonic Cell Lincage Analysis," *American Chemical Society: Divison of Inorganic Chemistry*, 209th ACS National Meeting, Anaheim, California. Abstract No. 385 (Apr. 2–6, 1995).

Aguayo, J.B., et al. "Nuclear Magnetic Resonance Imaging of a Single Cell," Nature, Letters to Nature 322:190–191 (Jul. 10, 1986).

Alexander, "Design and Synthesis of Macrocyclic Ligands and Their Complexes of Lanthanides and Antinides," Chem. Review, 95:273–342 (1995).

Borch, R.F., et al. "The Cyanohydridoborate Anion as a Selective Reducing Agent," Journal of the American Chemical Society 93(12):2897–2904 (Jun. 16, 1971).

Cho, Z.H., et al. "Some Experiences on a 4$\mu\mu$m NMR Microscopy," Book of Abstracts, vol. 1, p. 233, Society of Magnetic Resonance in Medicine, 6th Annual Meeting and Exhibition, Aug. 17–21, 1987, New York City, NY.

(List continued on next page.)

*Primary Examiner*—Dameron L. Jones
(74) *Attorney, Agent, or Firm*—Robin M. Silva, Esq.; Renee M. Kosslak, Esq.; Dorsey & Whitney LLP

(57) ABSTRACT

The invention relates to novel magnetic resonance imaging contrast agents and methods of detecting physiological signals or substances.

16 Claims, 24 Drawing Sheets

OTHER PUBLICATIONS

Grynkiewicz, G., et al. "A New Generation of Ca2+ Indicators with Greatly Improved Fluorescence Properties," The Journal of Biological Chemistry, 260(6): 3440–3450 (1985).

Hennessy, M.J., et al. "NMR Surface Coil Microscopy," Book of Abstracts, vol. 2, p. 461–462, Society of Magnetic Resonance in Medicine, 5th Annual Meeting and Exhibition, Aug. 19–22, 1986, Montreal, Quebec, Canada.

Hoult, D.I., et al. "The Signal–to–Noise Ratio of the Nuclear Magnetic Resonance Experiment," Journal of Magnetic Resonance, 24: 71–85 (1976).

Jackels, "Section III: Enhancement Agents for Magnetic Resonance and Ultrasound Imaging, Chapter 20: Enhancement Agents for Magnetic Resonance Imaging: Fundamentals," Pharm. Med. Imag. Section III, Chap. 20, pp. 645–661 (1990).

Johnson, G.A., et al., "MR Microscopy at 7.0 T," Works in Progress, Society of Magnetic Resonance in Medicine, Sixth Annual Meeting and Exhibition, Aug. 17–21, 1987, New York City, NY. p.23.

Li, et al., "A Calcium–Sensitive Magnetic Resonance Imaging Contrast Agent," J. Am. Chem. Soc., 121:1413–1414 (1999).

Meade, T.J. et al., "Hydrophobic, Regiospecific Guest Binding by Transition–Metal Host Complexes Having Permanent Voids as Revealed by FT–NMR Relaxation Studies," J. Am. Chem. Soc., 108:1954–1962 (1986).

Meyer et al., "Advances in Macrocyclic Gadolinium Complexes as Magnetic Resonance Imaging Contrast Agents," Investigative Radiology, 25(1):S53–S55 (Sep. 1990).

Moats, et al., "A "Smart" Magnetic Resonance Imaging Agent That Reports on Specific Enzymatic Activity," Angew. Chem. Int. Ed. Engl., 36(7): 726–728 (Apr. 1997).

Moi, M.K., et al. "The Peptide Way to Macrocyclic Bifunctional Chelating Agents: Synthesis of 2–(p–Nitrobenzyl) – 1,4,7,10–tetraazacyclododecan–N, N", N, N""–tetraacetic Acid and Study of Its Yttrium (III) Complex, J. Am. Chem. Soc. 110(18):6266–6267 (1988).

Nijhof, E.J., et al. "High–Resolution Proton Imaging at 4.7 Tesla," Proceedings of Soc. Magn. Reson. Med., p. 925 (1987).

Runge, V.M., et al. "Future Directions in Magnetic Resonance Contrast Media," Top Magn. Reson. Imaging., 3(2):85–97 (1991).

Russell, E.J., et al. "Multicenter Double–Blind Placebo–Controlled Study of Gadopentetate Dimeglumine as an MR Contrast Agent: Evaluation in Patients with Cerebral Lesions," American Journal of Roentgenology, 152:813–823 (Apr. 1989).

Shukla, et al., "Design of Conformationally Rigid Dimeric MRI Agents," Magnetic Resonance in Medicine, 36(6): 928–931 (1996).

Sillerud, L.O., et al. "Proton NMR Microscopy of Intact Multicellular Tumor Spheroids," Book of Abstracts, vol. 1, p. 468, Society of Magnetic Resonance in Medicine, 6th Annual Meeting and Exhibition, Aug. 17–21, 1987, New York City, NY.

Tsien, R.Y. "New Calcium Indicators and Buffers with High Selectivity Against Magnesium and Protons: Design, Synthesis, and Properties of Prototype Structures," Biochemistry, 19(11): 2396–2404 (1980).

Tweedle, M.F., et al. "Considerations Involving Paramagnetic Coordination Compounds as Useful NMR Contrast Agents," Nucl. Med. Bio. 15(1):31–36 (1988).

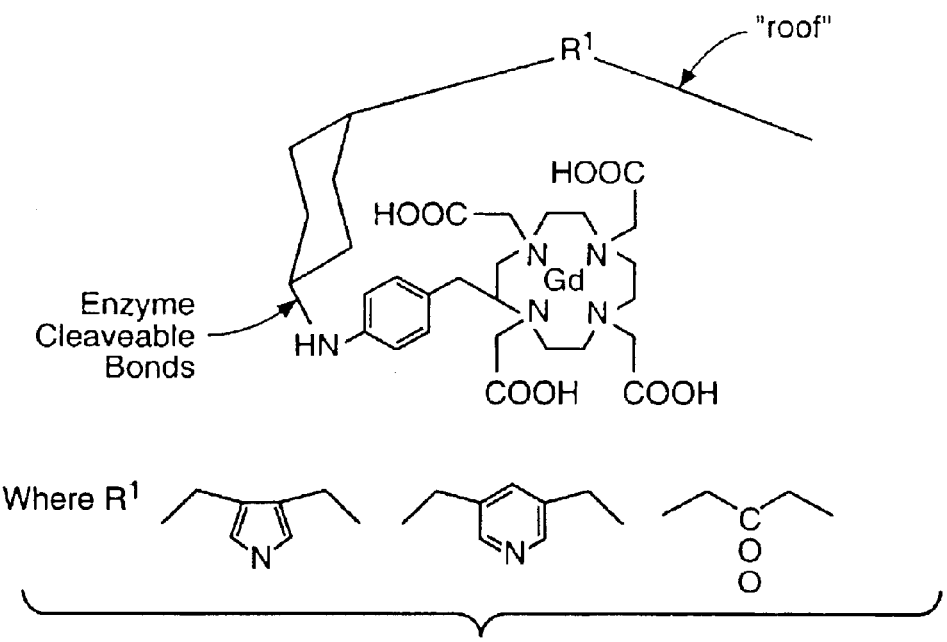
FIG._1
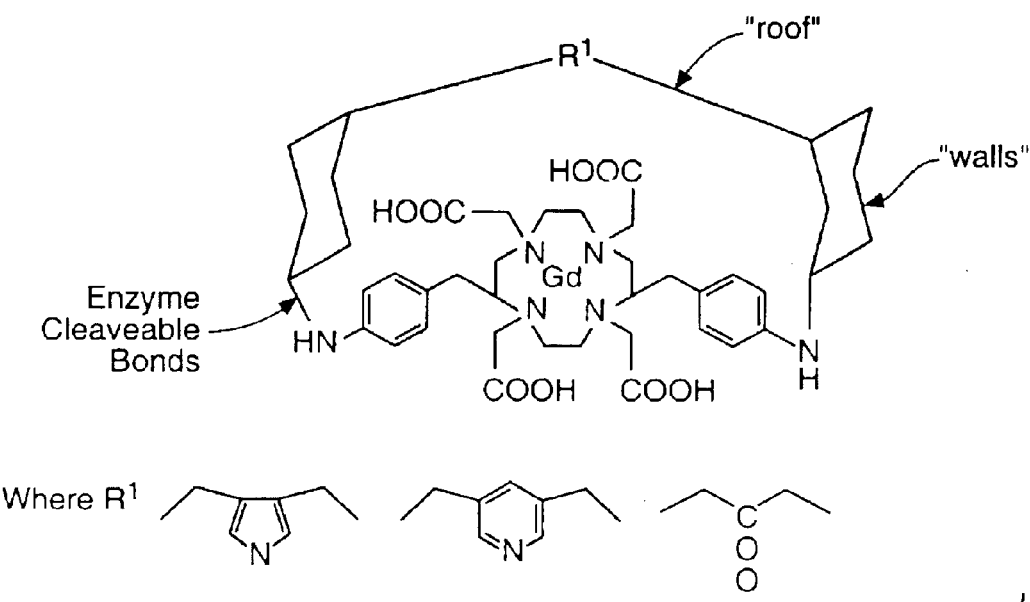
FIG._2

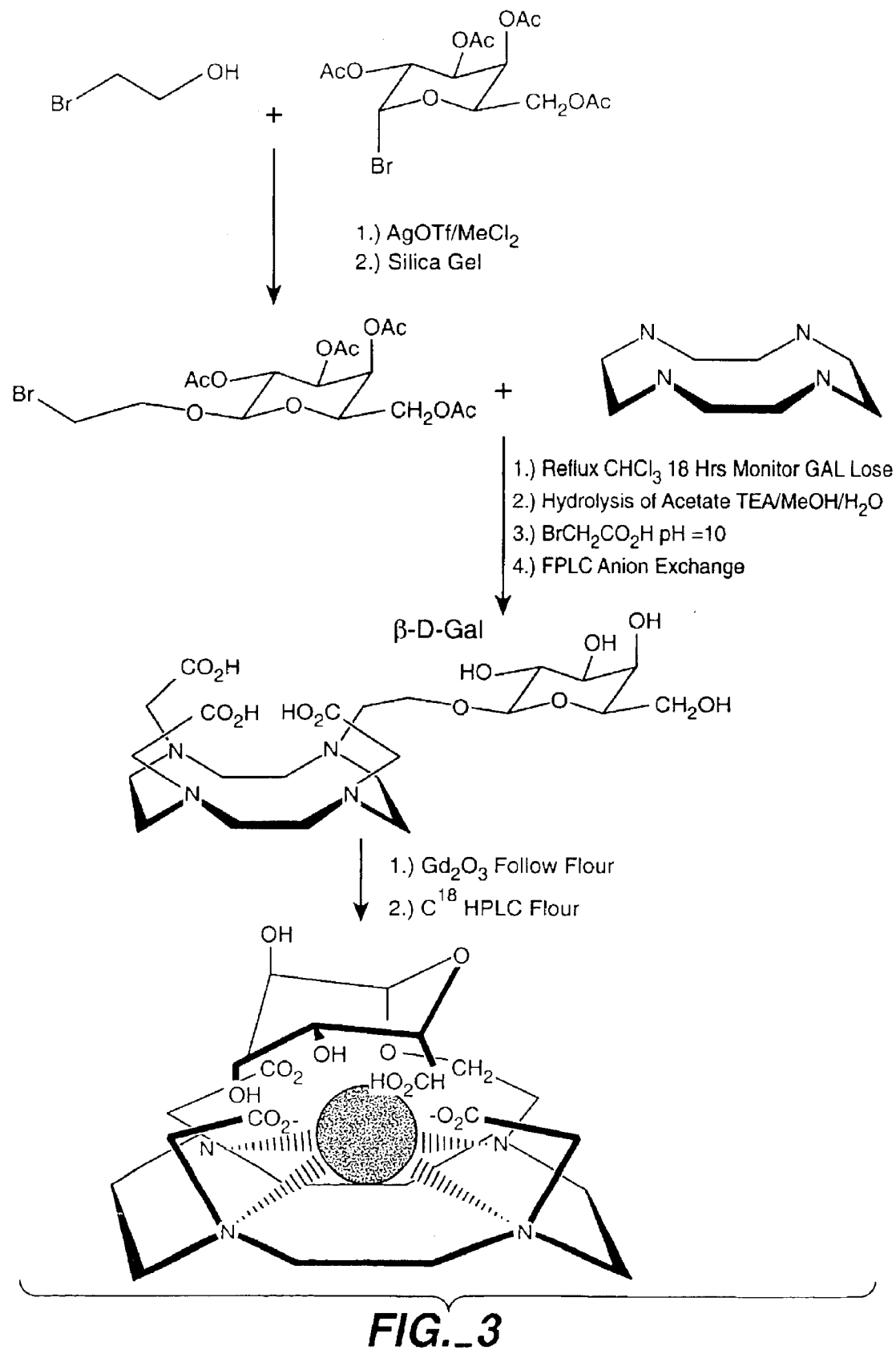
FIG._3

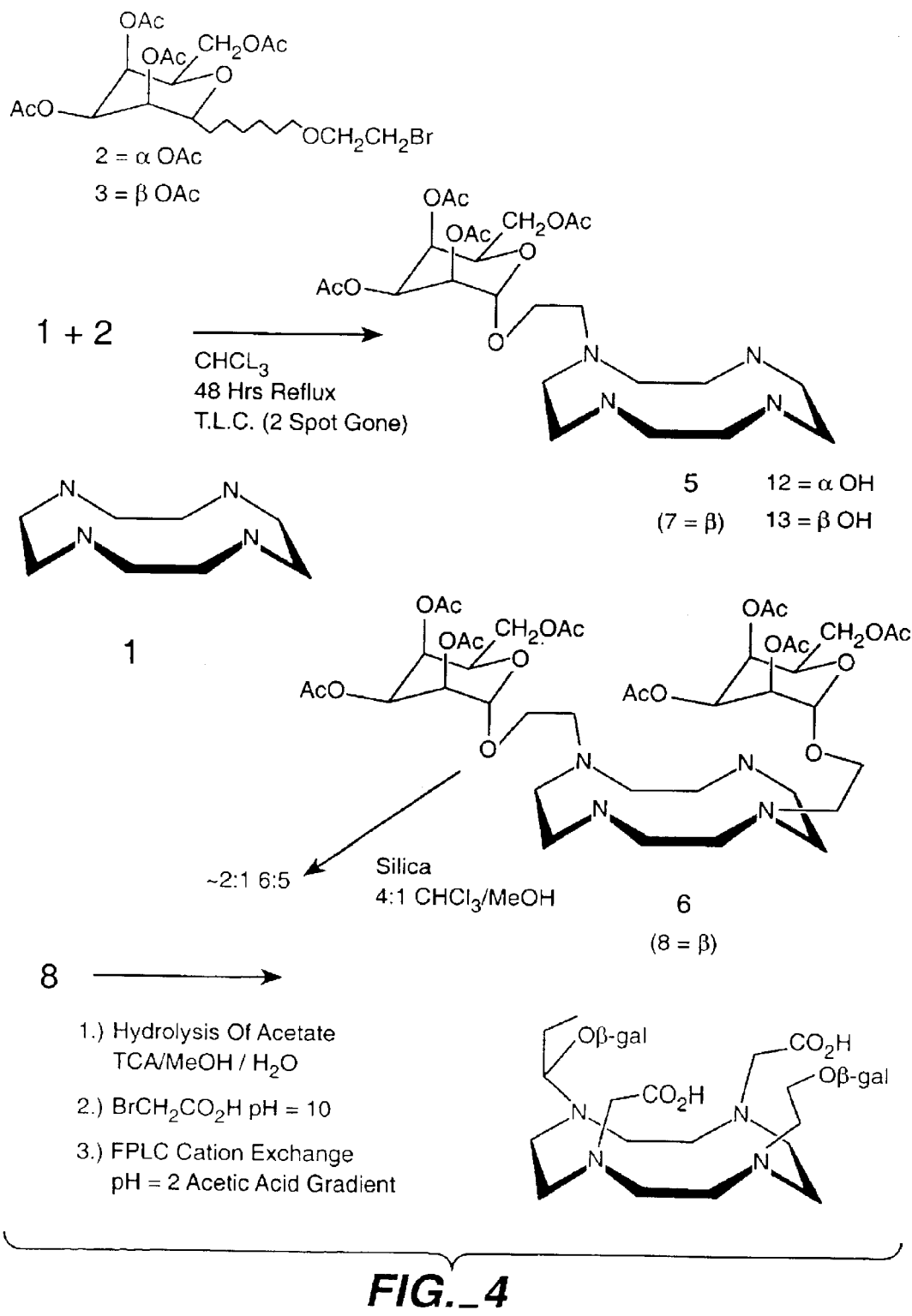
FIG._4

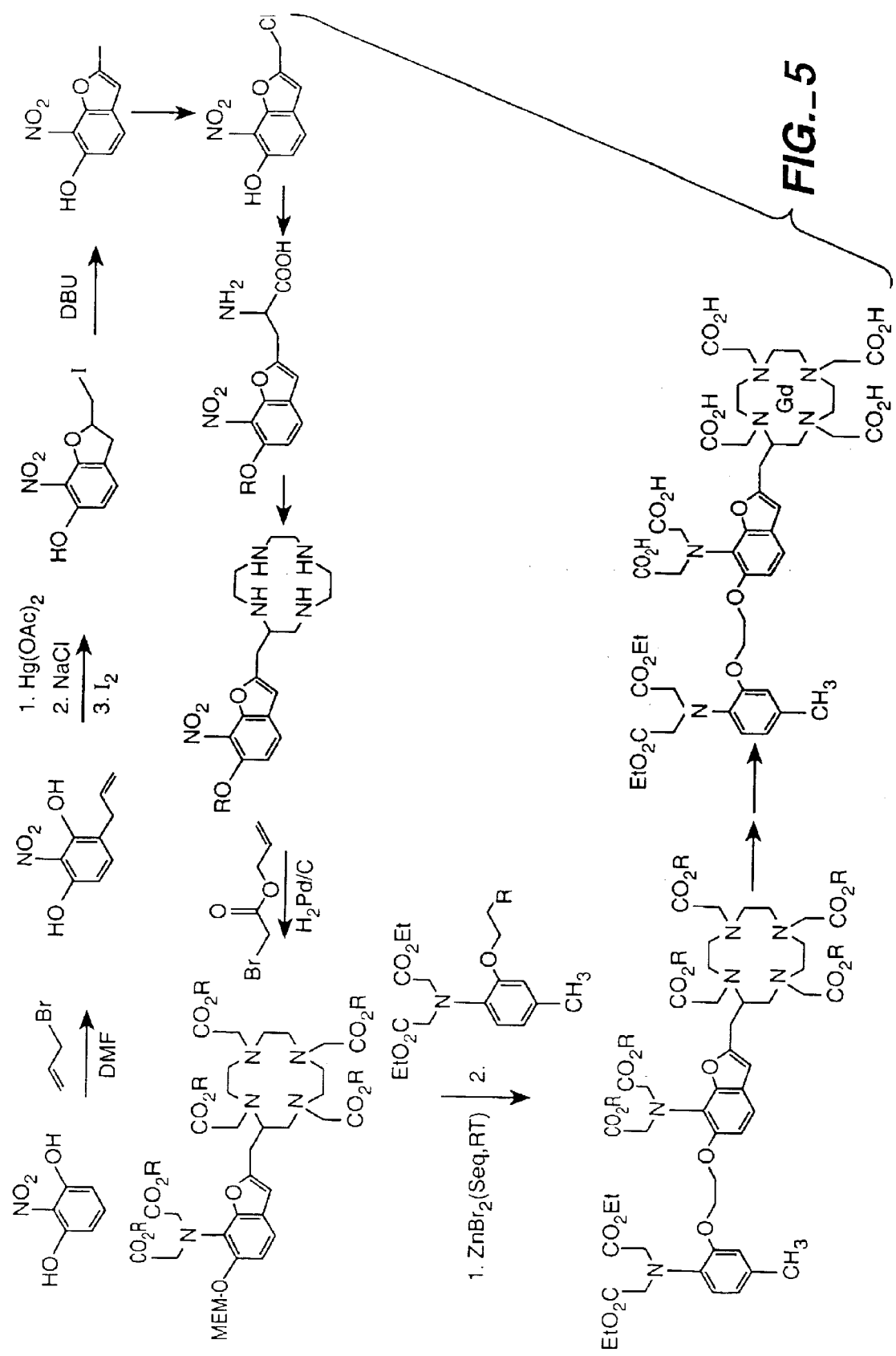
FIG._5

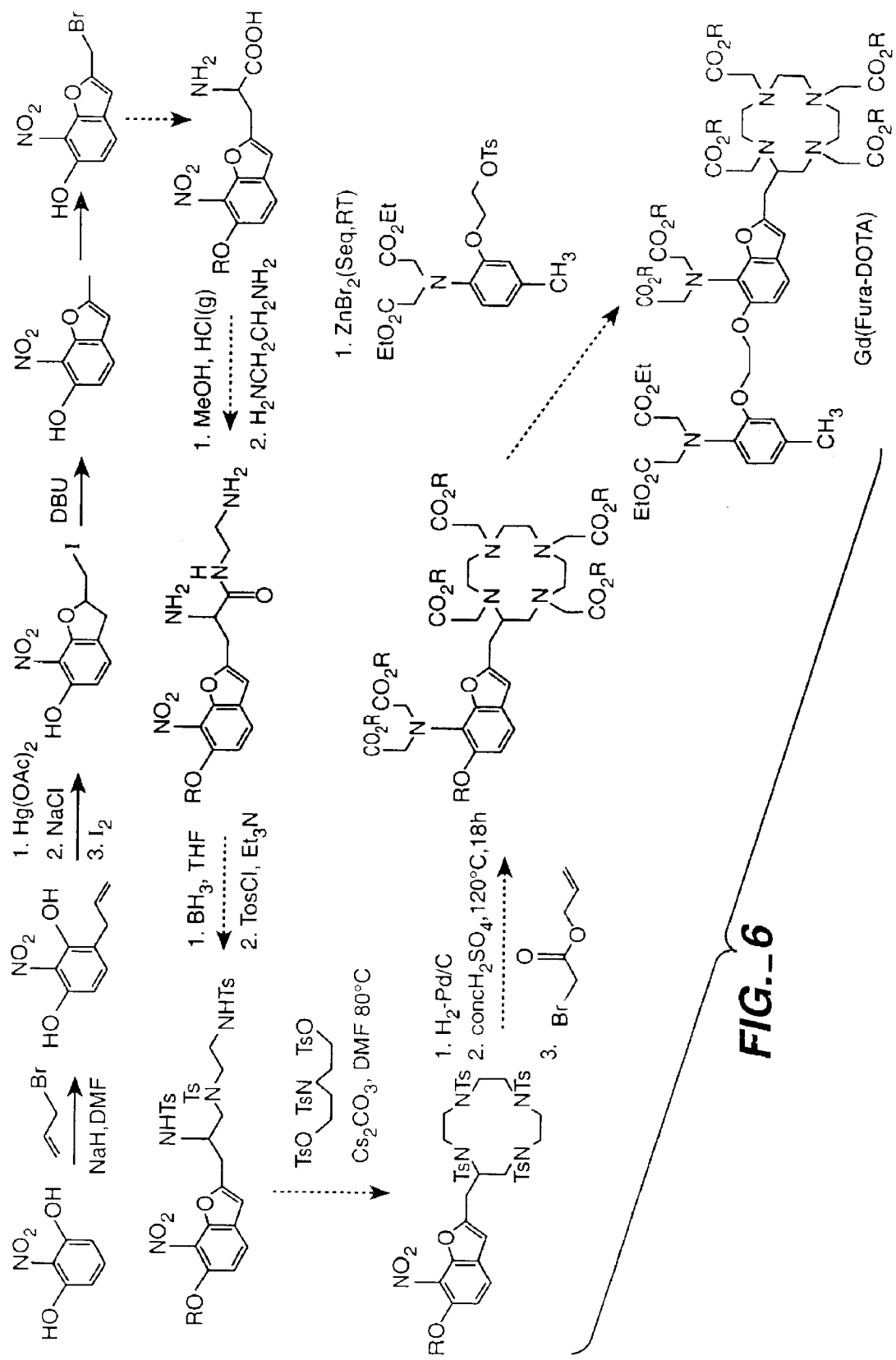
FIG._6

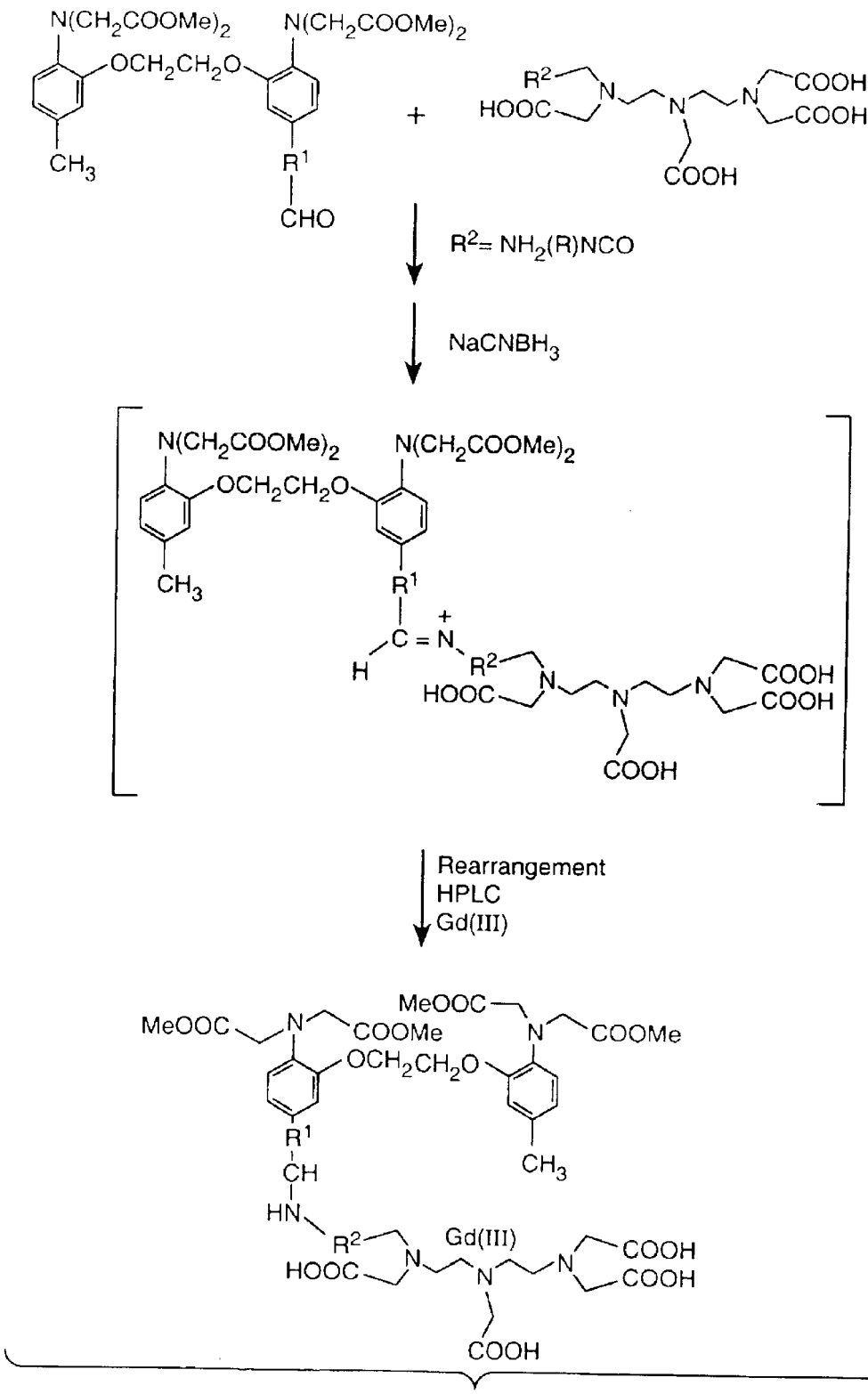
FIG._7

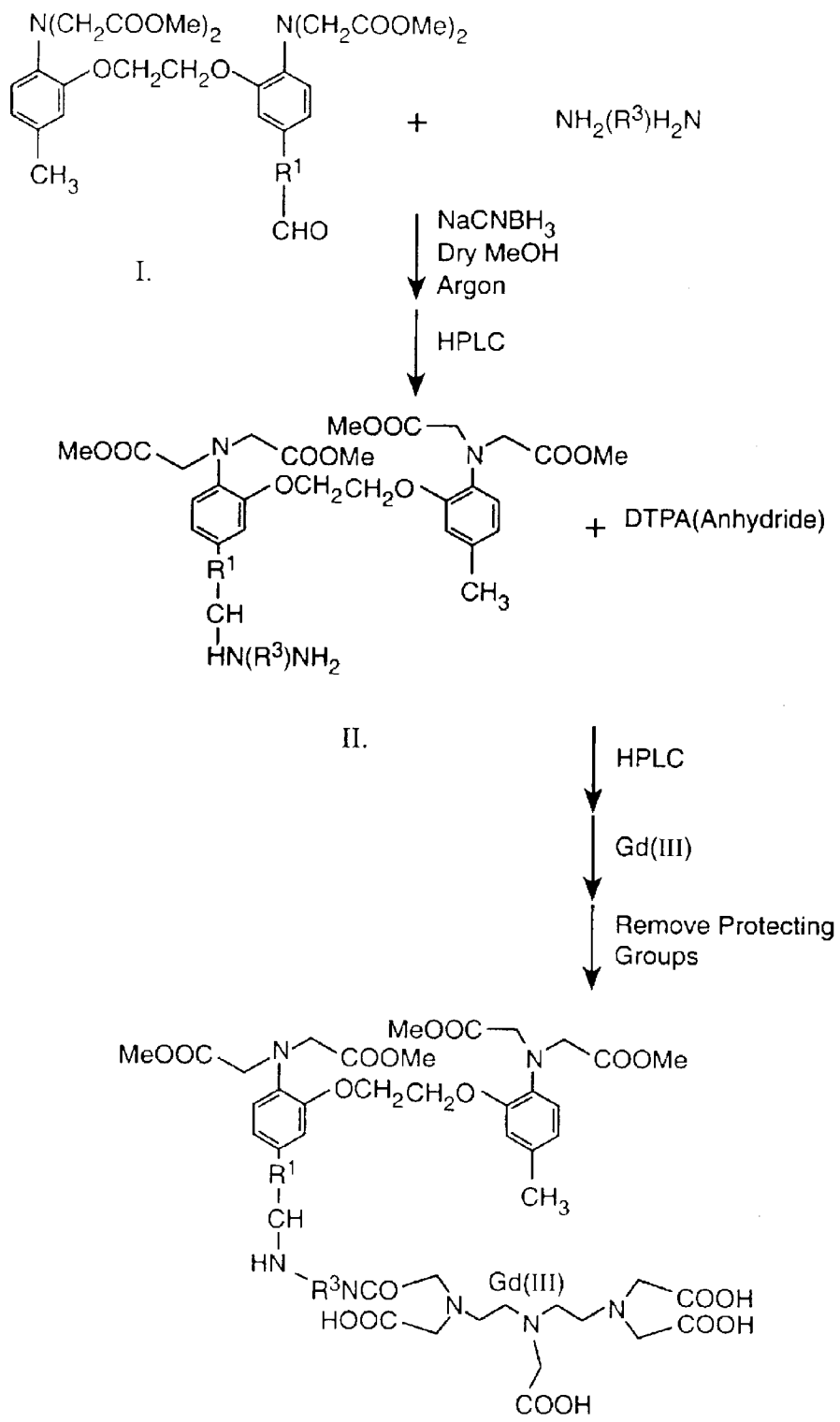
FIG._8

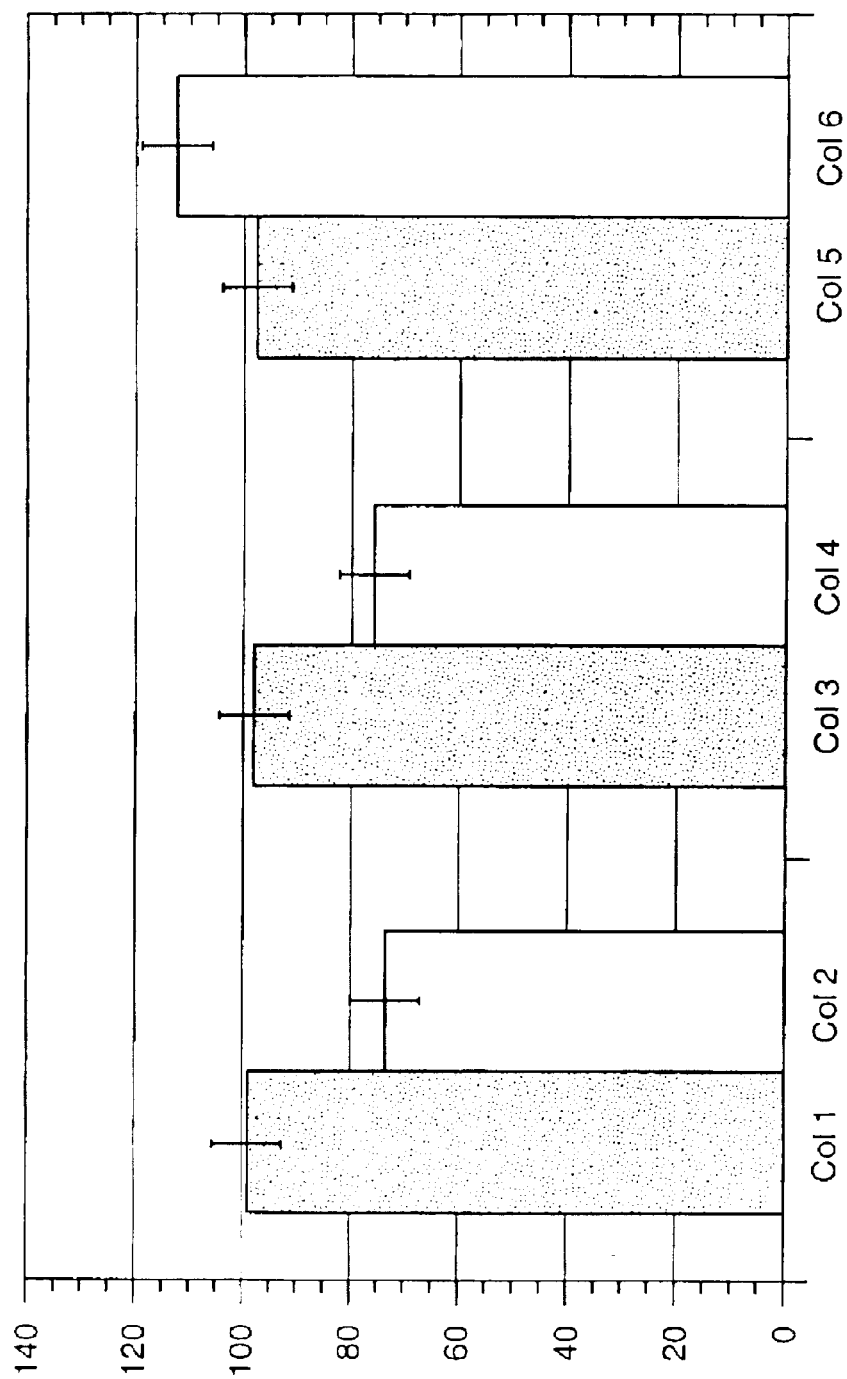
FIG._9

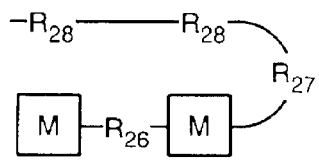
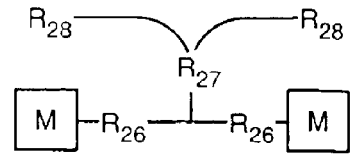
*FIG._10A*       *FIG._10B*
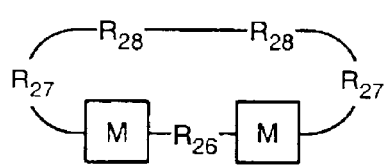
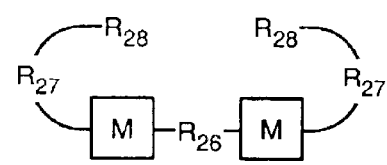
*FIG._10C*       *FIG._10D*
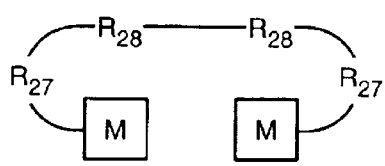
*FIG._10E*
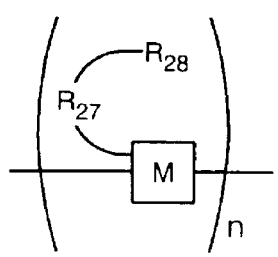
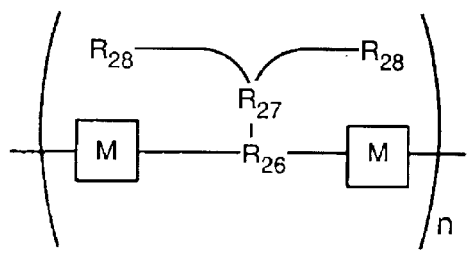
*FIG._10F*       *FIG._10G*
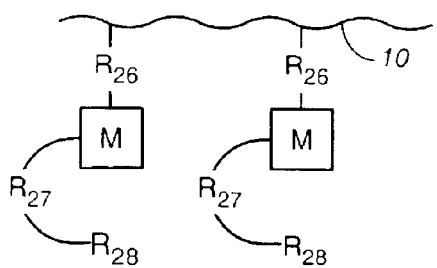
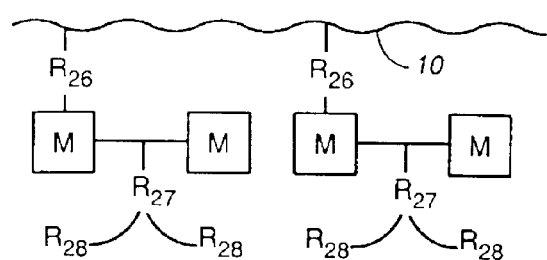
*FIG._10H*       *FIG._10I*

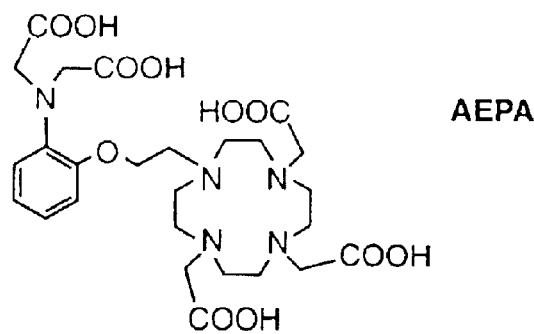
1-o-aminophenoxy-2-(cyclen)ethane-N,N,N',N'',N'''-pentaacetic acid
FIG._11A
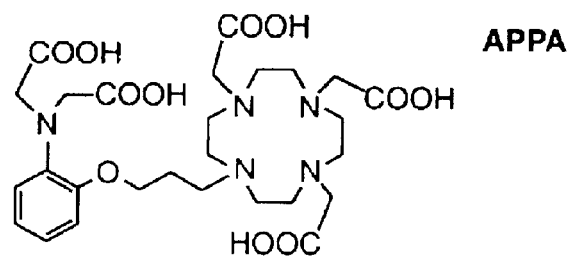
1-o-aminophenoxy-3-(cyclen)propane-N,N,N',N'',N'''-pentaacetic acid
FIG._11B
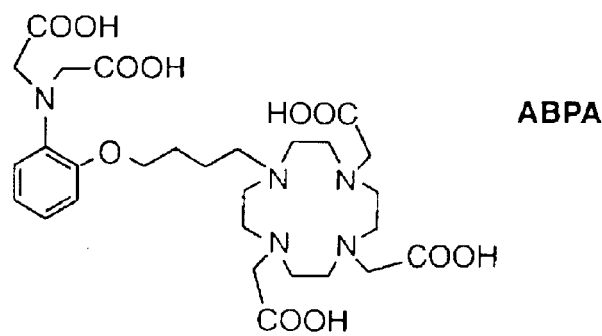
1-o-aminophenoxy-4-(cyclen)butane-N,N,N',N'',N'''-pentaacetic acid
FIG._11C

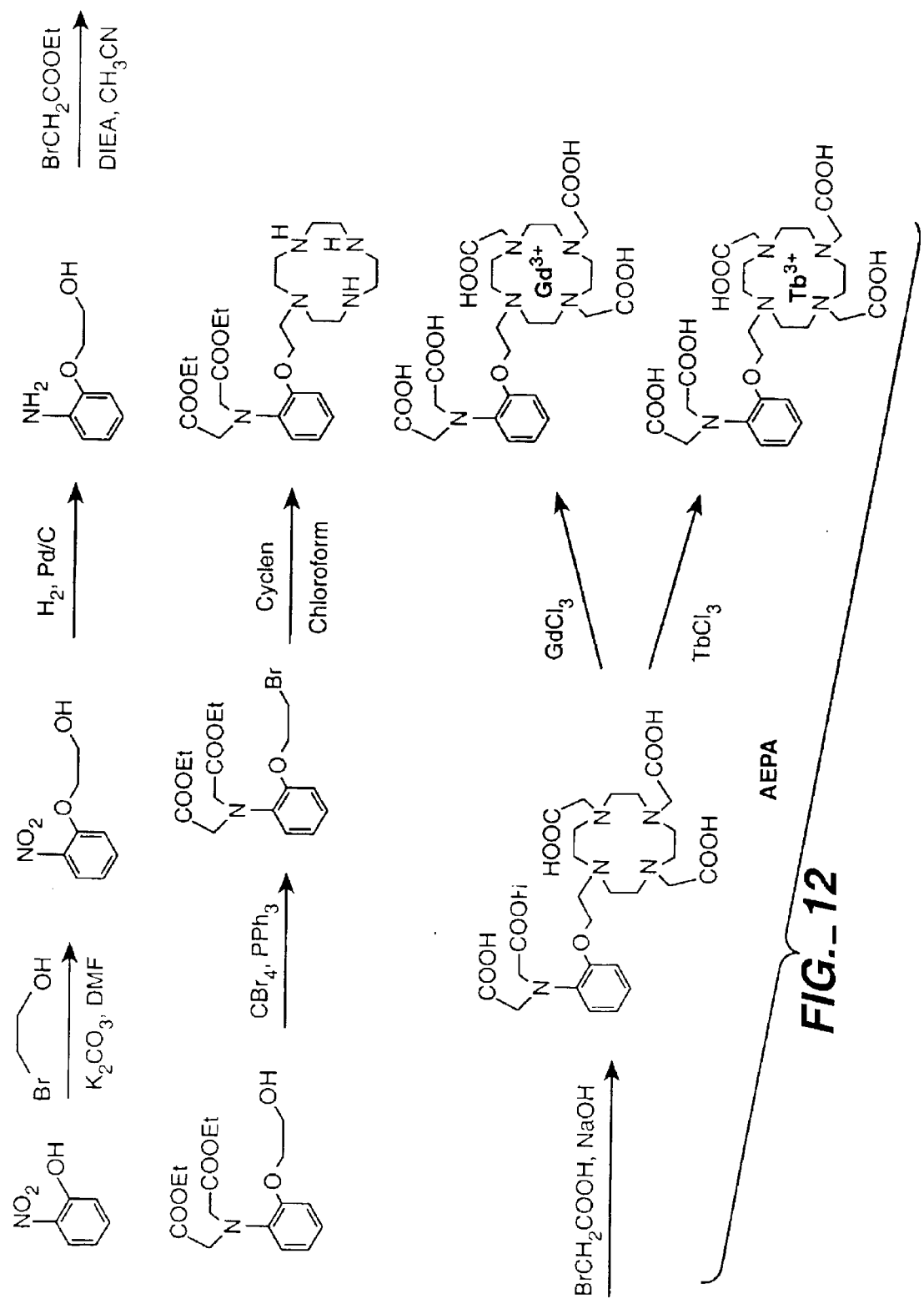
FIG._12

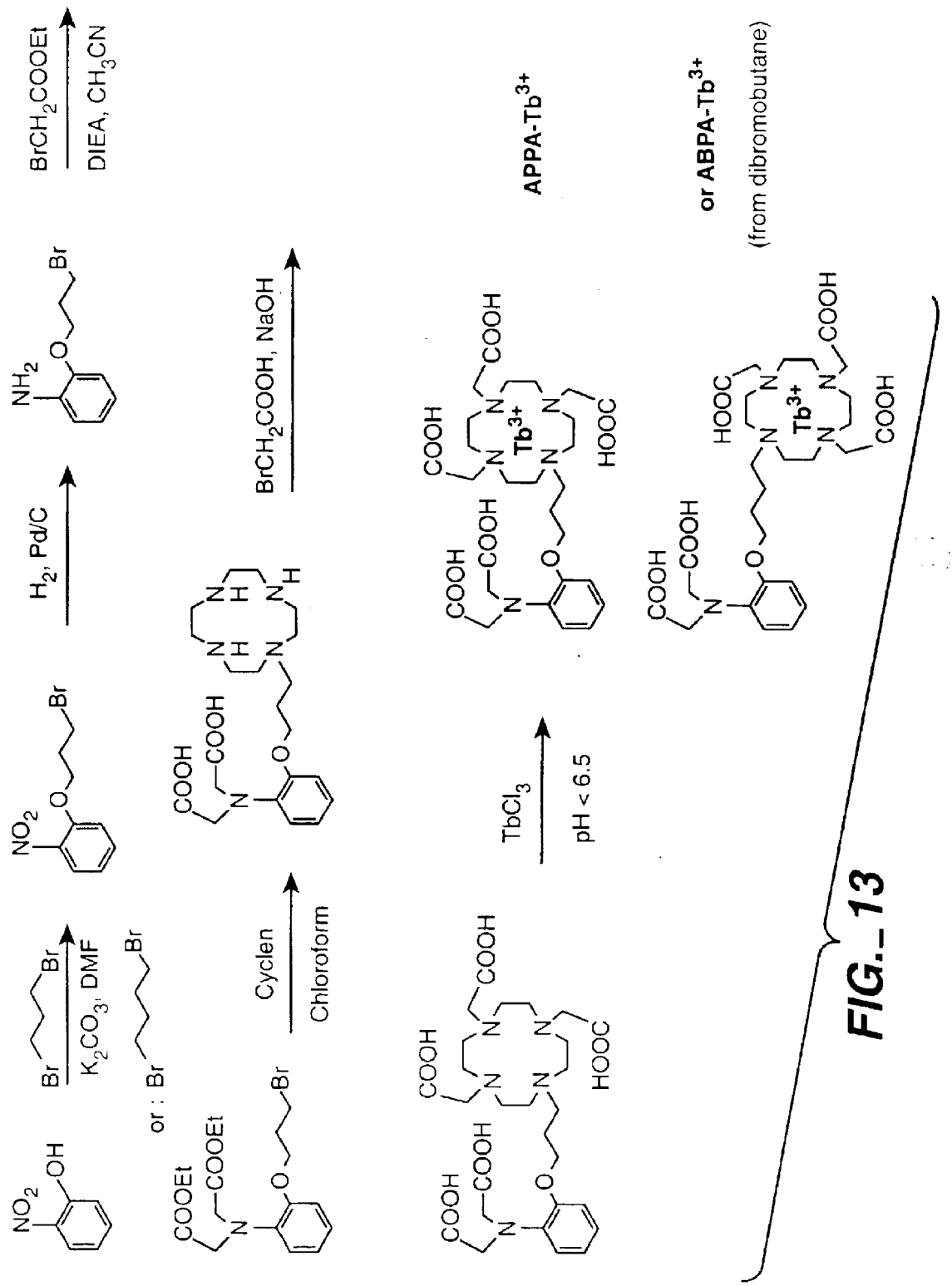
FIG._13

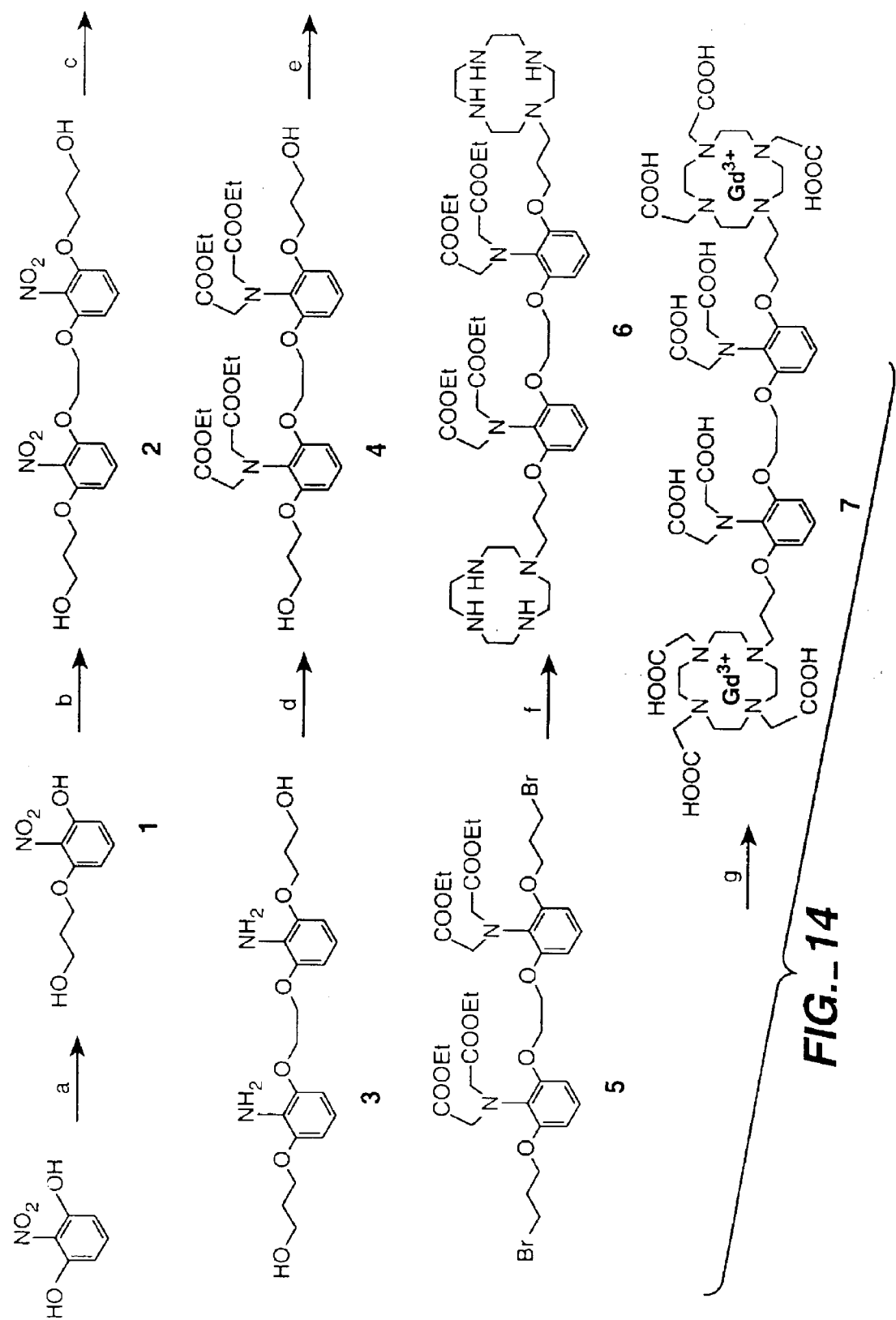
FIG._14

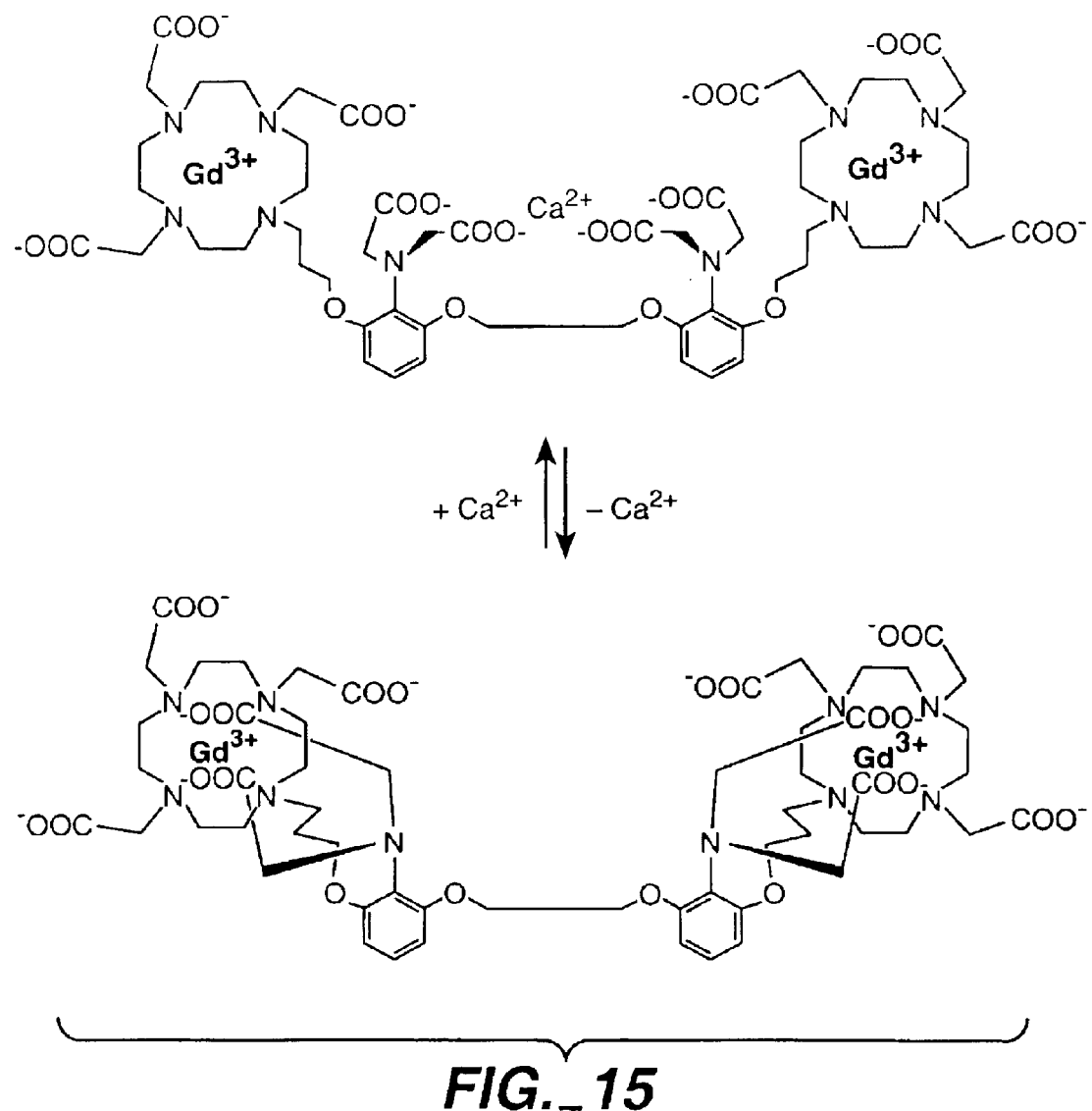
FIG._15

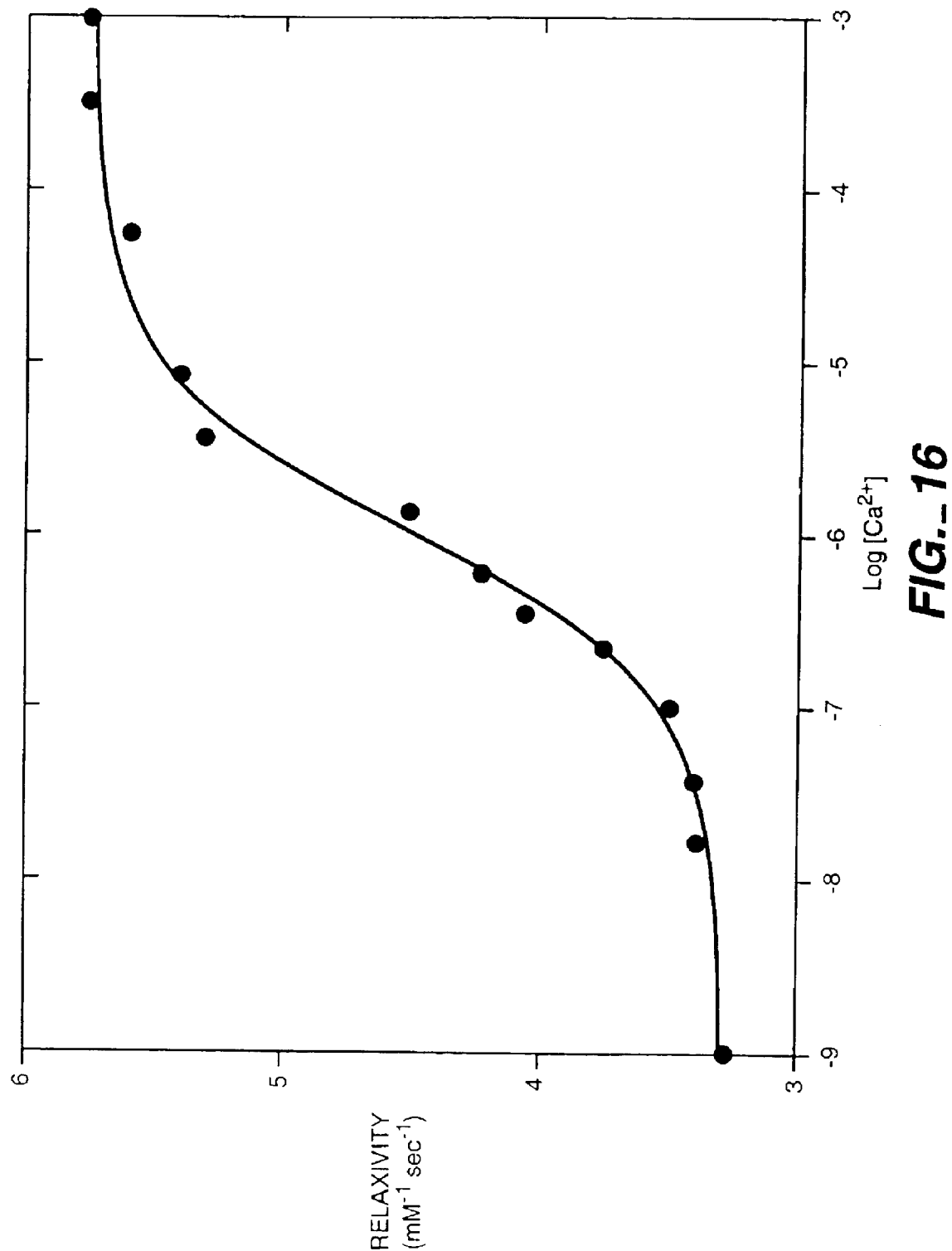
FIG._16

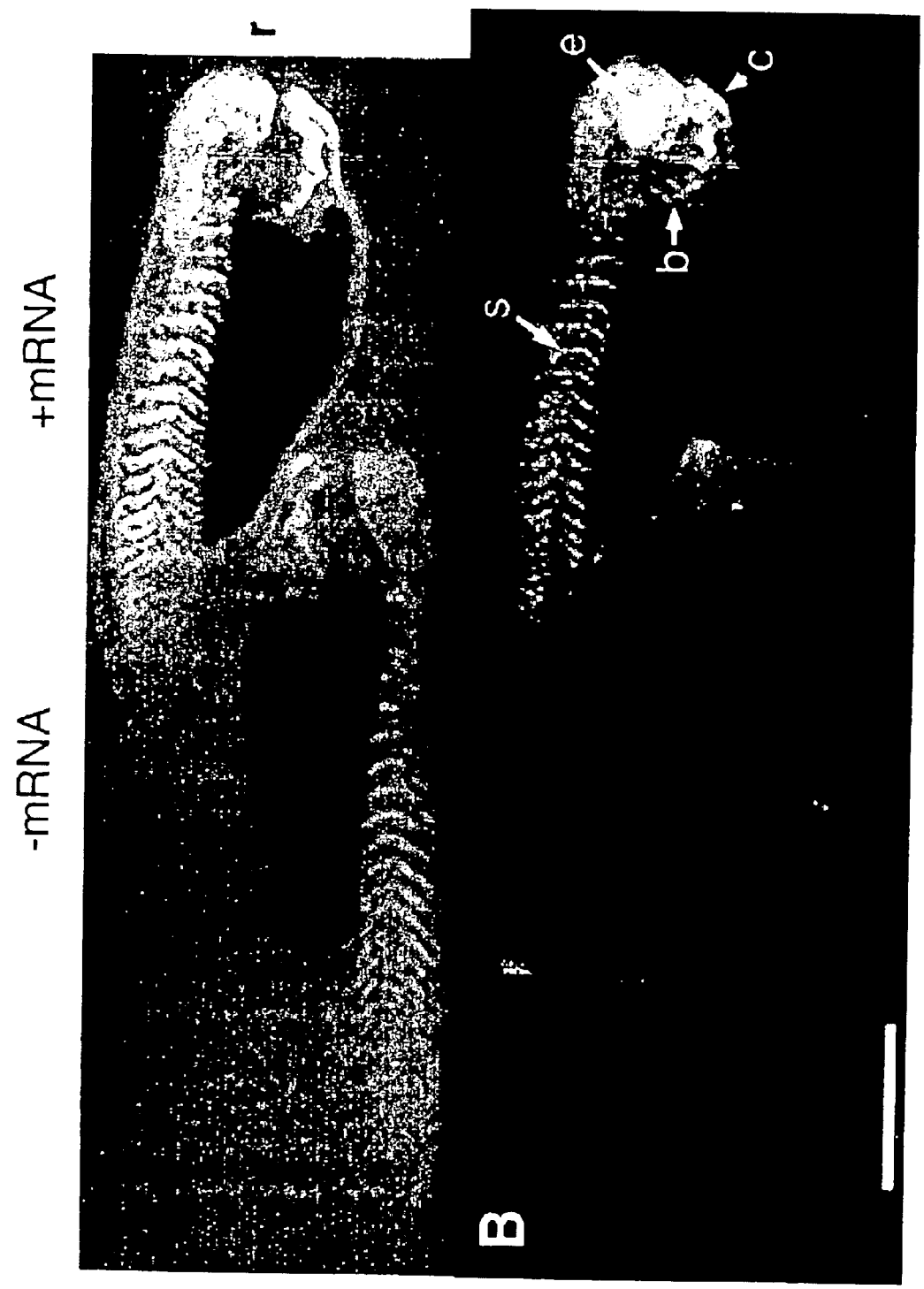
FIG._17

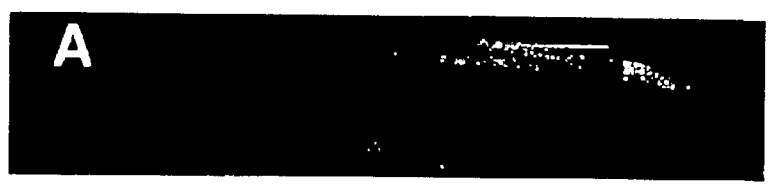
FIG._18A
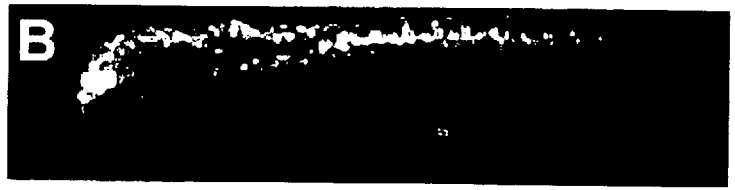
FIG._18B
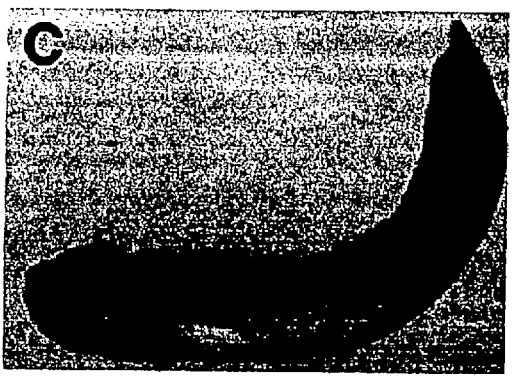
FIG._18C
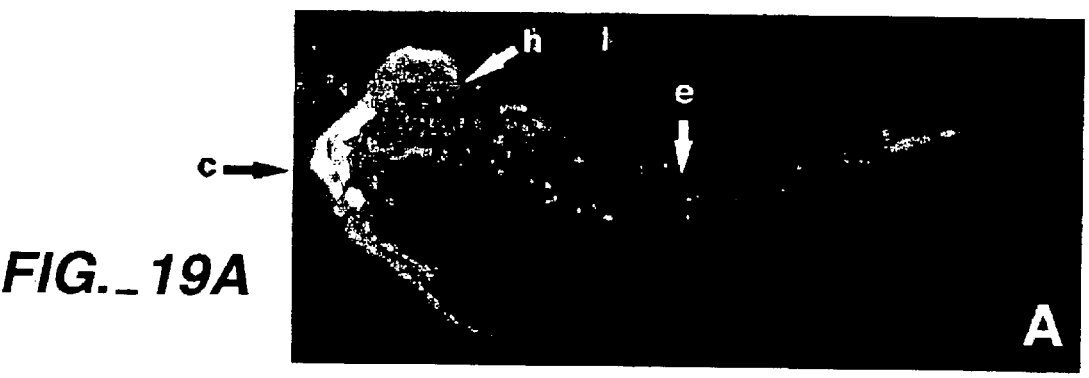
FIG._19A
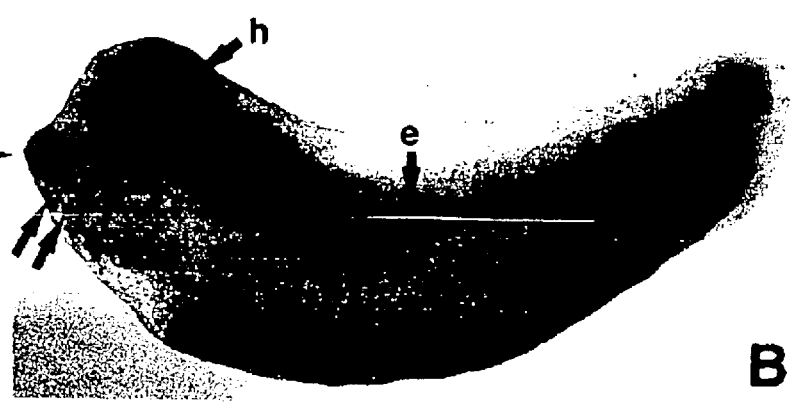
FIG._19B

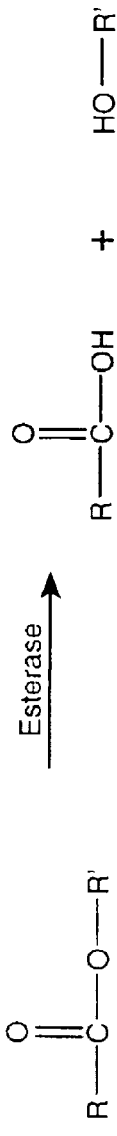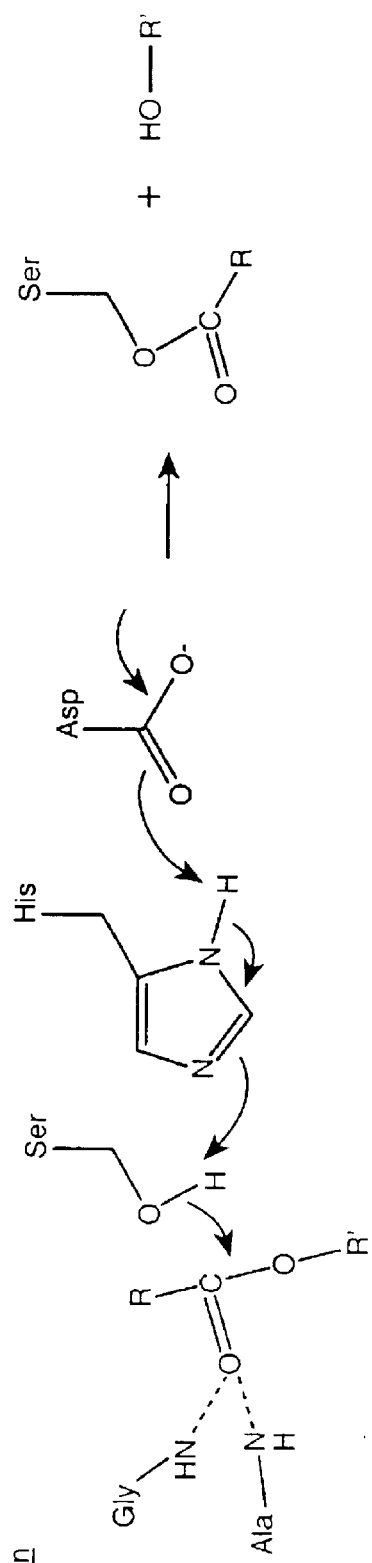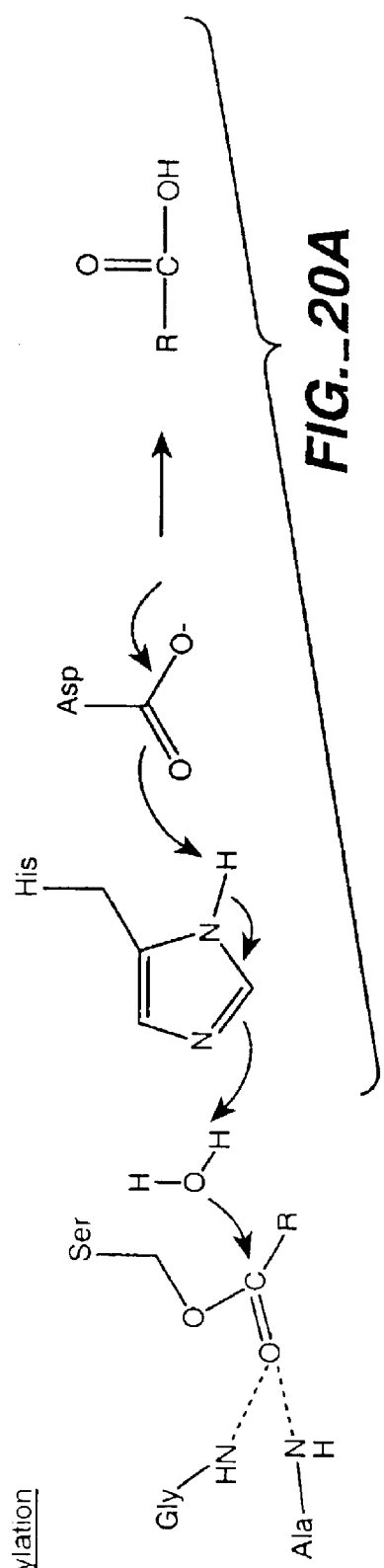
FIG. 20A

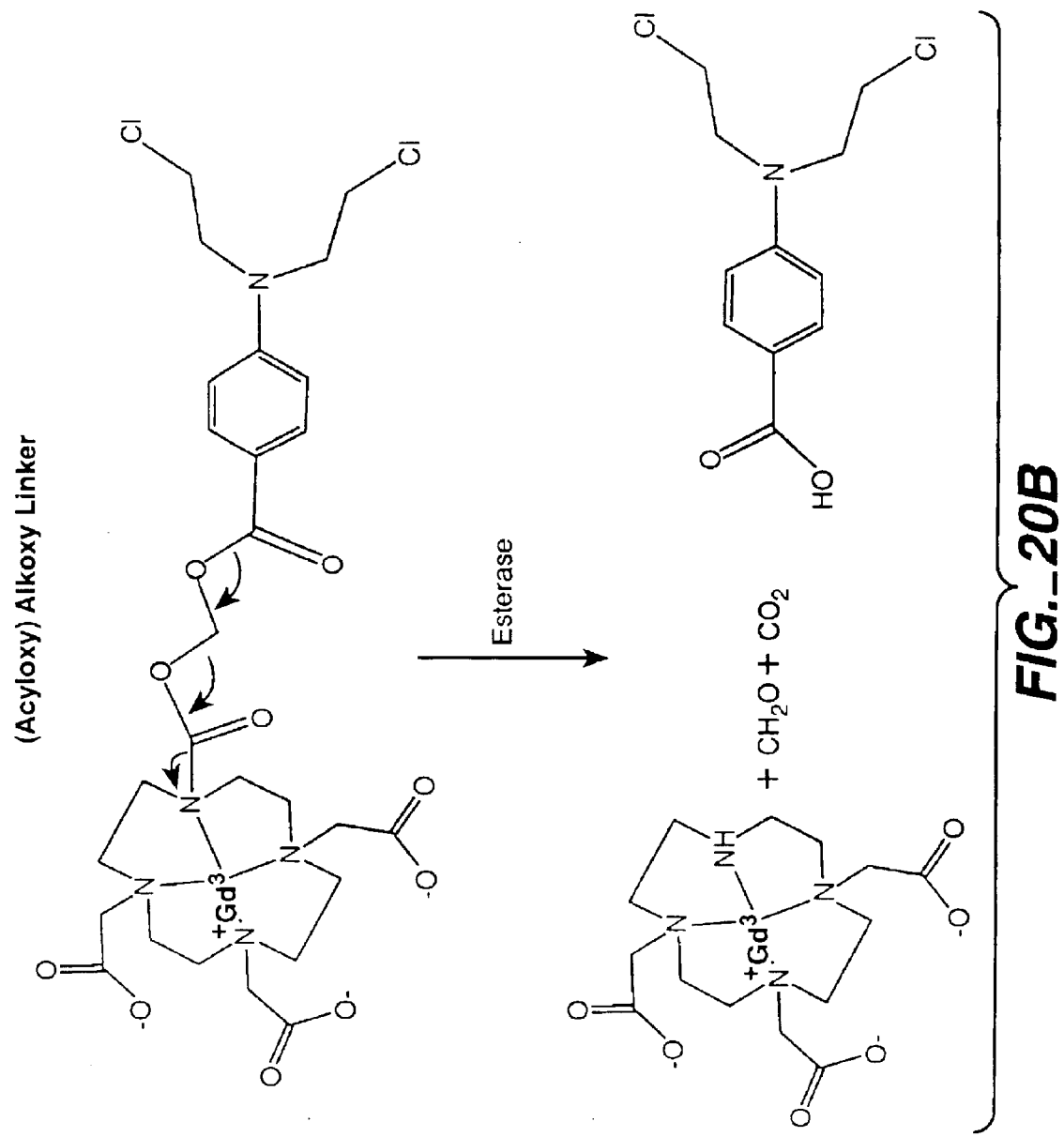
FIG._20B

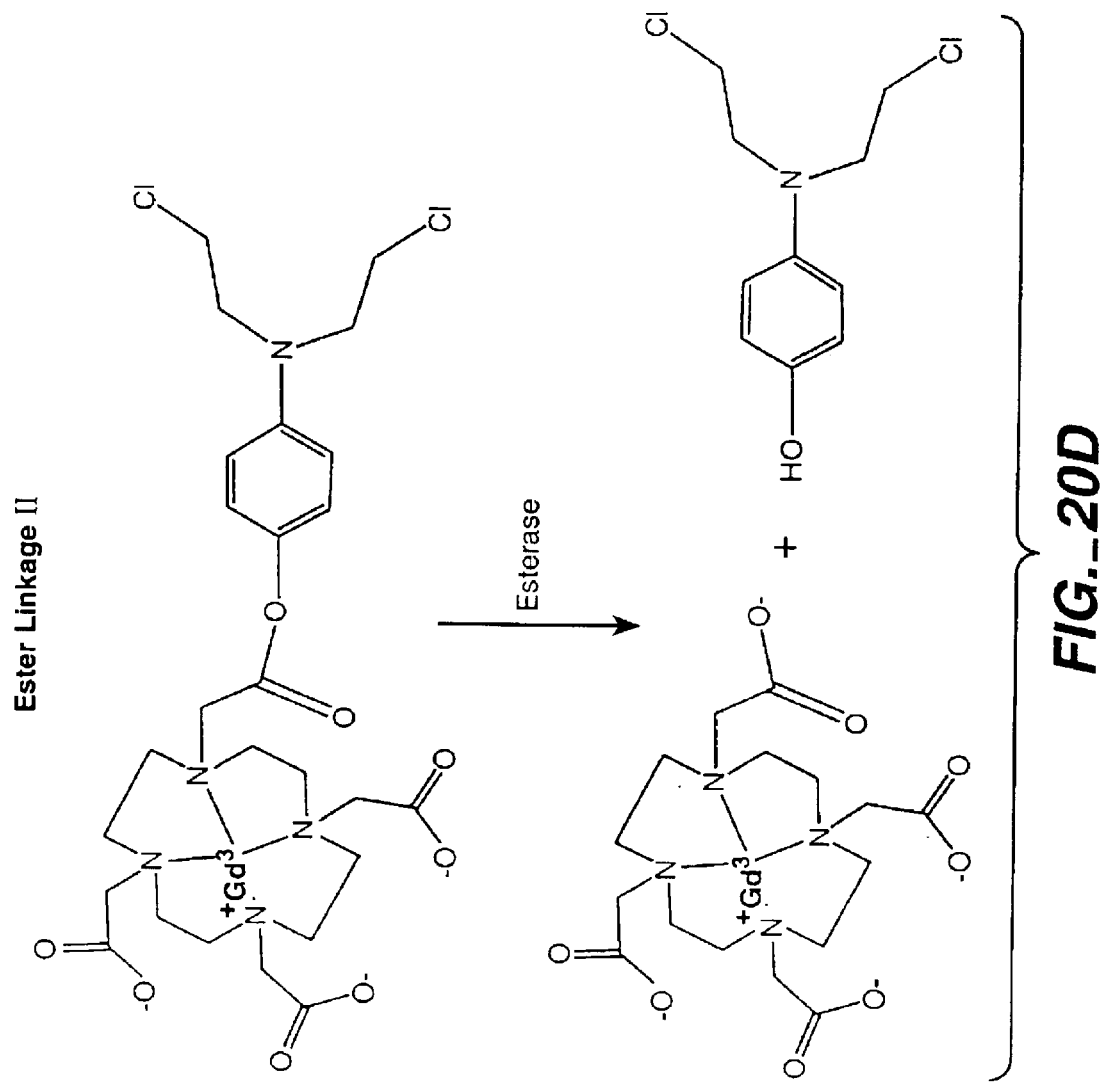

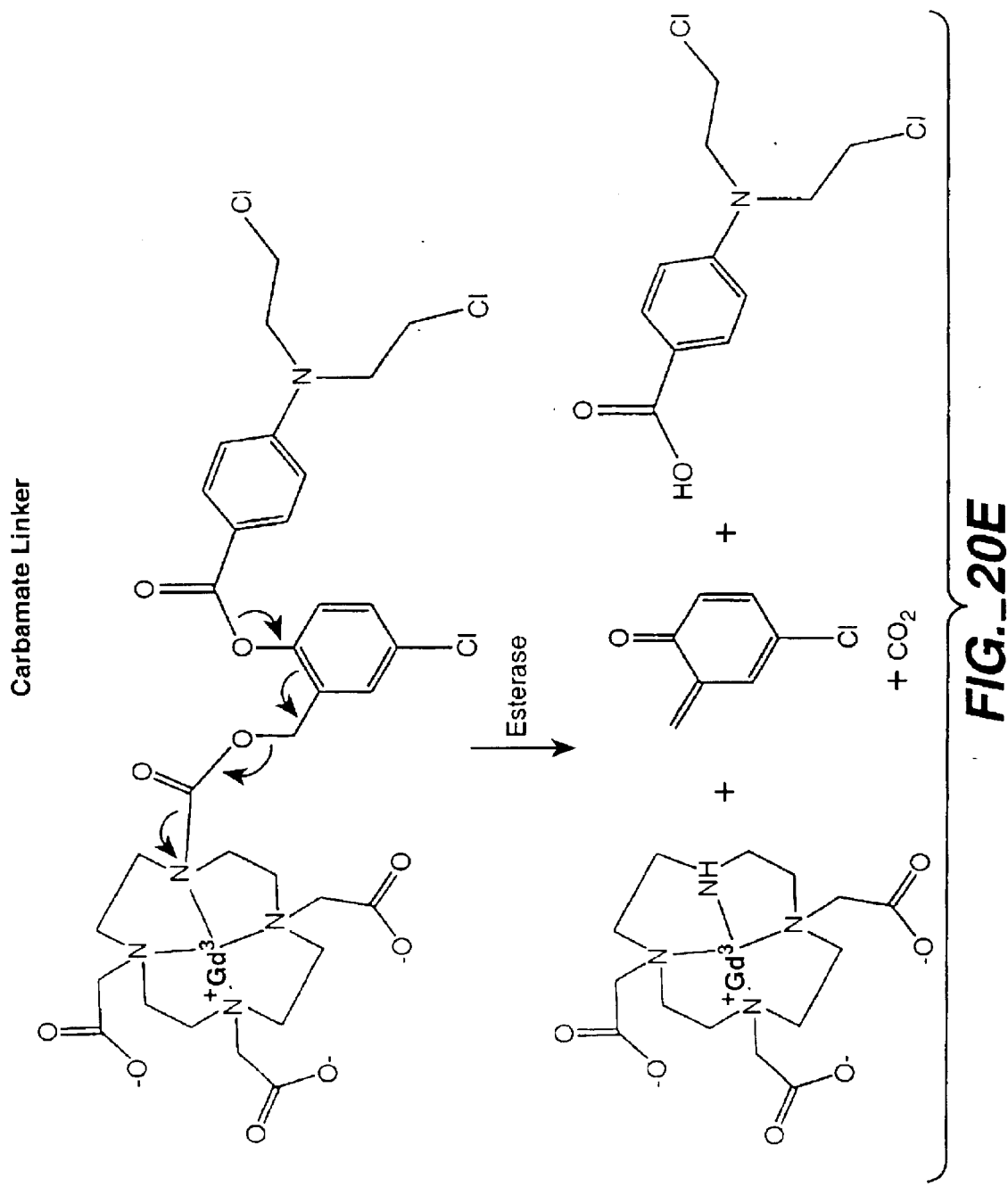
FIG._20E

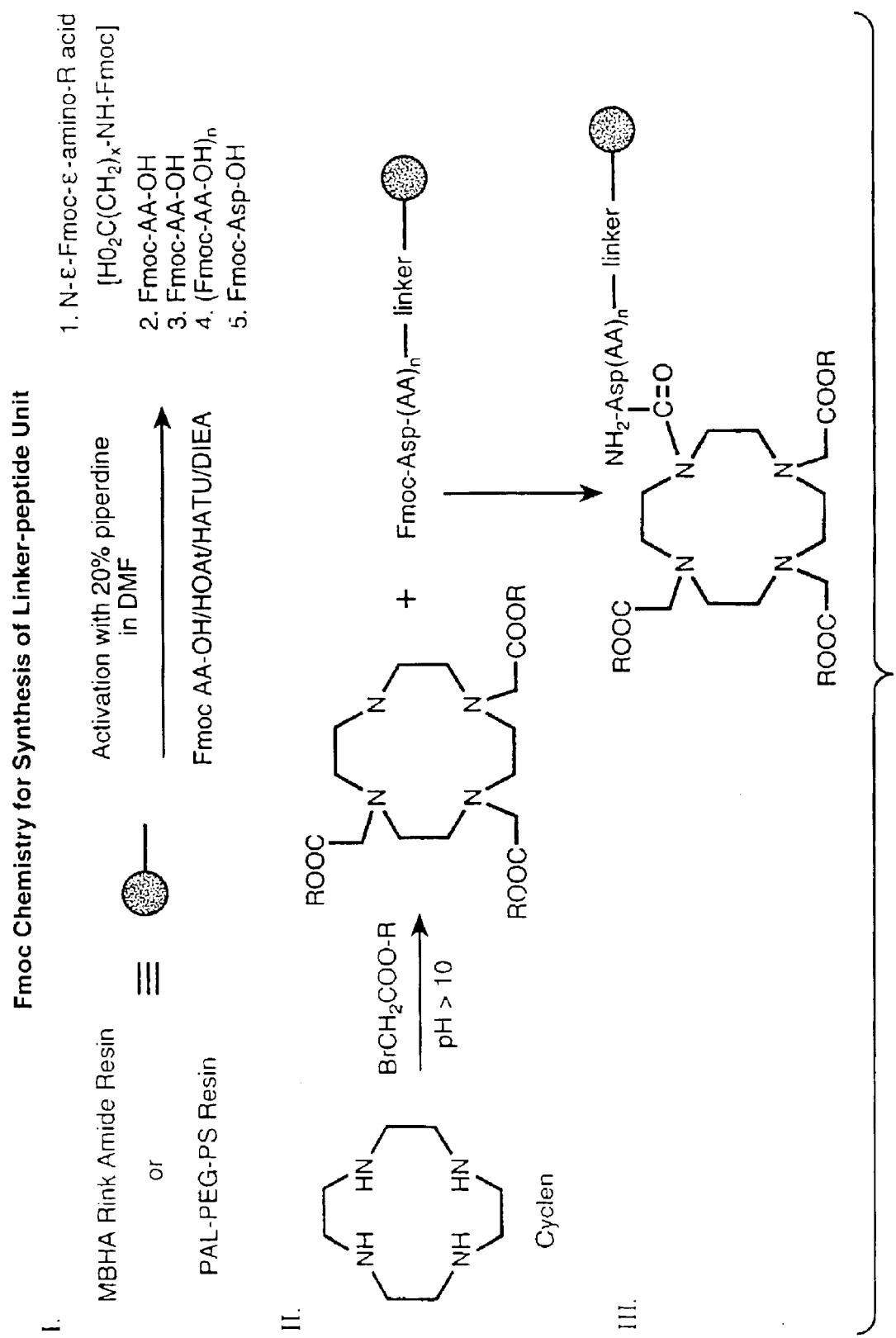
FIG._21

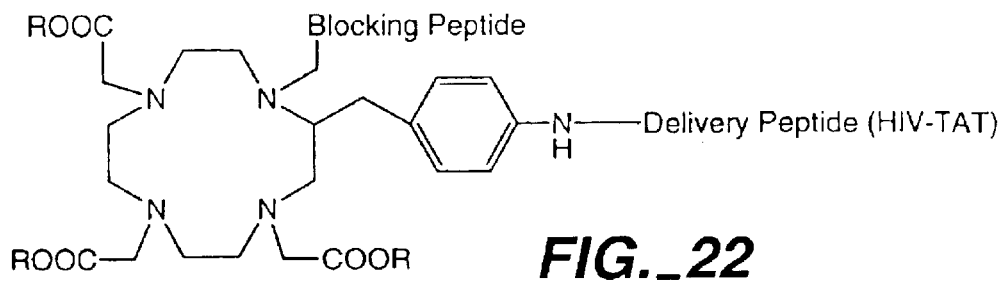
FIG._22
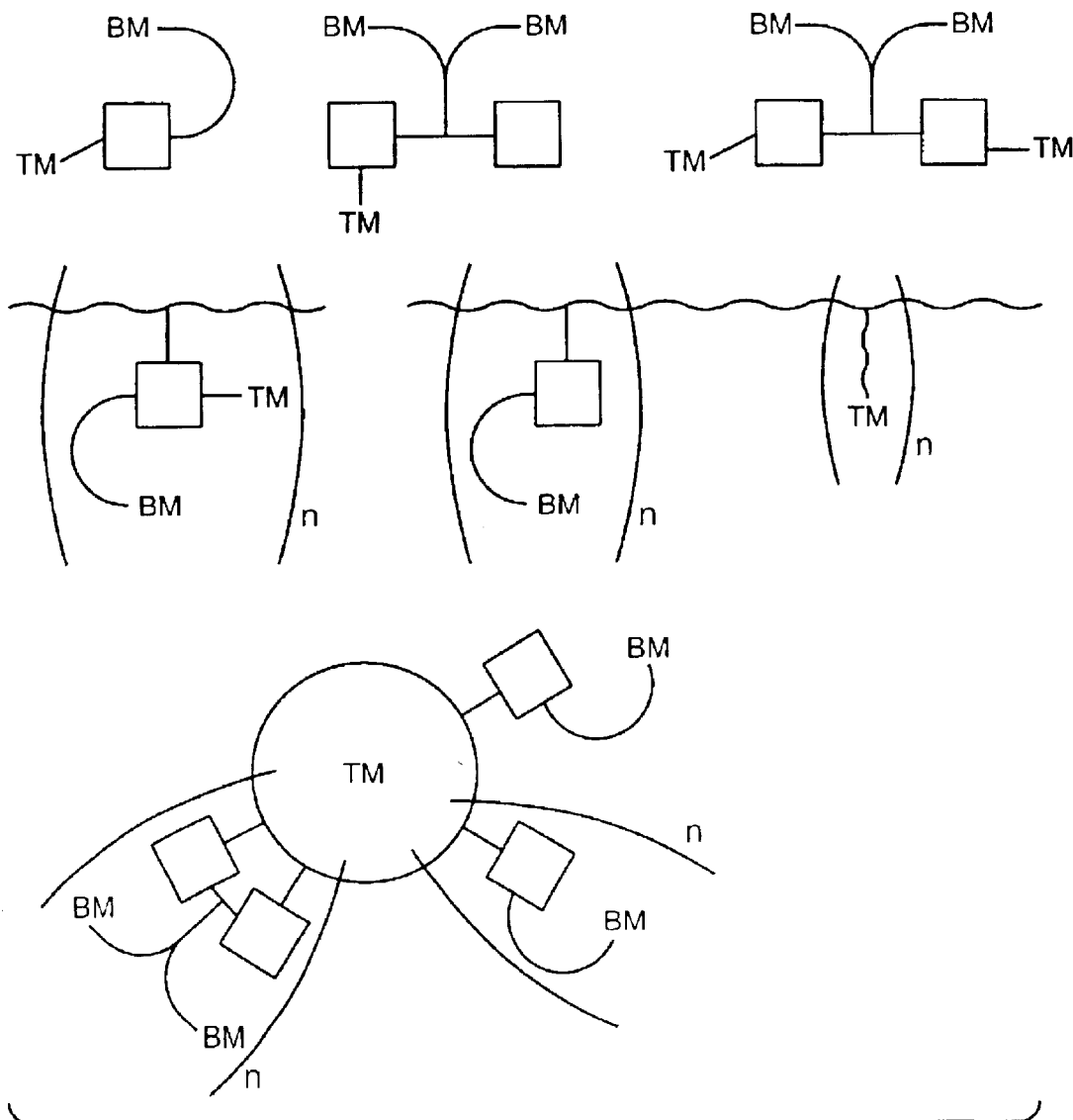
FIG._23

SEQUENCE LISTING

<160> NUMBER OF SEQ ID NOS: 17

<210> SEQ ID NO 1
<211> LENGTH: 4
<212> TYPE: PRT
<213> ORGANISM: Unknown
<220> FEATURE:
<223> OTHER INFORMATION: could be from any mammal.

<400> SEQUENCE: 1

Gly Gly Gly Phe
1

<210> SEQ ID NO 2
<211> LENGTH: 10
<212> TYPE: PRT

```
<213> ORGANISM: Unknown
<220> FEATURE:
<223> OTHER INFORMATION: could be from any mammal.

<400> SEQUENCE: 2

Gly Phe Gln Gly Val Gln Phe Ala Gly Phe
1               5                   10

<210> SEQ ID NO 3
<211> LENGTH: 10
<212> TYPE: PRT
<213> ORGANISM: Unknown
<220> FEATURE:
<223> OTHER INFORMATION: could be from any mammal.

<400> SEQUENCE: 3

Cys Phe Gly Ser Val Gly Phe Ala Gly Phe
1               5                   10

<210> SEQ ID NO 4
<211> LENGTH: 10
<212> TYPE: PRT
<213> ORGANISM: Unknown
<220> FEATURE:
<223> OTHER INFORMATION: could be from any mammal.

<400> SEQUENCE: 4

Gly Leu Val Gly Gly Ala Gly Ala Gly Phe
1               5                   10

<210> SEQ ID NO 5
<211> LENGTH: 10
<212> TYPE: PRT
<213> ORGANISM: Unknown
<220> FEATURE:
<223> OTHER INFORMATION: could be from any mammal.

<400> SEQUENCE: 5

Gly Gly Phe Leu Gly Leu Gly Ala Gly Phe
1               5                   10

<210> SEQ ID NO 6
<211> LENGTH: 10
<212> TYPE: PRT
<213> ORGANISM: Unknown
<220> FEATURE:
<223> OTHER INFORMATION: could be from any mammal.

<400> SEQUENCE: 6

Cys Phe Gly Ser Thr Phe Phe Ala Gly Phe
1               5                   10

<210> SEQ ID NO 7
<211> LENGTH: 4
<212> TYPE: PRT
<213> ORGANISM: Unknown
<220> FEATURE:
<223> OTHER INFORMATION: could be from any mammal.

<400> SEQUENCE: 7

Asp Glu Val Asp
1

<210> SEQ ID NO 8
<211> LENGTH: 4
<212> TYPE: PRT
<213> ORGANISM: Unknown
```

```
<220> FEATURE:
<223> OTHER INFORMATION: could be from any mammal.

<400> SEQUENCE: 8

Pro Glu Leu Arg
1

<210> SEQ ID NO 9
<211> LENGTH: 6
<212> TYPE: PRT
<213> ORGANISM: Unknown
<220> FEATURE:
<223> OTHER INFORMATION: could be from any mammal.

<400> SEQUENCE: 9

Pro Leu Gly Leu Ala Arg
1               5

<210> SEQ ID NO 10
<211> LENGTH: 7
<212> TYPE: PRT
<213> ORGANISM: Unknown
<220> FEATURE:
<223> OTHER INFORMATION: could be from any mammal.

<400> SEQUENCE: 10

Pro Gly Leu Trp Ala Asp Arg
1               5

<210> SEQ ID NO 11
<211> LENGTH: 7
<212> TYPE: PRT
<213> ORGANISM: Unknown
<220> FEATURE:
<223> OTHER INFORMATION: could be from any mammal.

<400> SEQUENCE: 11

Pro Met Ala Leu Trp Met Arg
1               5

<210> SEQ ID NO 12
<211> LENGTH: 6
<212> TYPE: PRT
<213> ORGANISM: Unknown
<220> FEATURE:
<223> OTHER INFORMATION: could be from any mammal.

<400> SEQUENCE: 12

Pro Met Gly Leu Arg Ala
1               5

<210> SEQ ID NO 13
<211> LENGTH: 7
<212> TYPE: PRT
<213> ORGANISM: Simian virus 40

<400> SEQUENCE: 13

Pro Lys Lys Lys Arg Lys Val
1               5

<210> SEQ ID NO 14
<211> LENGTH: 6
<212> TYPE: PRT
<213> ORGANISM: Homo sapiens

<400> SEQUENCE: 14
```

```
-continued

Ala Arg Arg Arg Arg Pro
 1               5

<210> SEQ ID NO 15
<211> LENGTH: 10
<212> TYPE: PRT
<213> ORGANISM: Mus musculus

<400> SEQUENCE: 15

Glu Glu Val Gln Arg Lys Arg Gln Lys Leu
 1               5                  10

<210> SEQ ID NO 16
<211> LENGTH: 9
<212> TYPE: PRT
<213> ORGANISM: Mus musculus

<400> SEQUENCE: 16

Glu Glu Lys Arg Lys Arg Thr Tyr Glu
 1               5

<210> SEQ ID NO 17
<211> LENGTH: 20
<212> TYPE: PRT
<213> ORGANISM: Xenopus laevis

<400> SEQUENCE: 17

Ala Val Lys Arg Pro Ala Ala Thr Lys Lys Ala Gly Gln Ala Lys Lys
 1               5                  10                  15

Lys Lys Leu Asp
             20
```

MAGNETIC RESONANCE IMAGING AGENTS FOR THE DETECTION OF PHYSIOLOGICAL AGENTS

This application claims the benefit of the filing date of Ser. No. 60/287,619, filed May 26, 2000 and is a continuation-in-part application of Ser. No. 09/405,046, filed Sep. 27, 1999; which is a continuation-in-part of application of Ser. No. 09/134,072, filed Aug. 13, 1998, now U.S. Pat. No. 5,980,862; which is a continuation of Ser. No. 08/971,855, filed Nov. 17, 1997, now abandoned; which is a 371 of PCT/US96/08548, filed Jun. 3, 1996, which is a continuation of provisional Ser. No. 60/063,328, filed Oct. 27, 1997; which is a continuation of Ser. No. 08/486,968, filed Jun. 7, 1995, now U.S. Pat. No. 5,707,605; which is a continuation of Ser. No. 08/460,511, filed Jun. 2, 1995, now abandoned.

FIELD OF THE INVENTION

The invention relates to novel magnetic resonance imaging contrast agents and methods of detecting physiological signals or substances.

BACKGROUND OF THE INVENTION

Magnetic resonance imaging (MRI) is a diagnostic and research procedure that uses high magnetic fields and radio-frequency signals to produce images. The most abundant molecular species in biological tissues is water. It is the quantum mechanical "spin" of the water proton nuclei that ultimately gives rise to the signal in all imaging experiments. In MRI the sample to be imaged is placed in a strong static magnetic field (1–12 Tesla) and the spins are excited with a pulse of radio frequency (RF) radiation to produce a net magnetization in the sample. Various magnetic field gradients and other RF pulses then act on the spins to code spatial information into the recorded signals. MRI is able to generate structural information in three dimensions in relatively short time spans.

The Image.

MR images are typically displayed on a gray scale with black the lowest and white the highest measured intensity (I). This measured intensity I=C*M, where C is the concentration of spins (in this case, water concentration) and M is a measure of the magnetization present at time of the measurement. Although variations in water concentration (C) can give rise to contrast in MR images, it is the strong dependence of the rate of change of M on local environment that is the source of image intensity variation in MRI. Two characteristic relaxation times, $T_1$ & $T_2$, govern the rate at which the magnetization can be accurately measured. $T_1$ is the exponential time constant for the spins to decay back to equilibrium after being perturbed by the RF pulse. In order to increase the signal-to-noise ratio (SNR) a typical MR imaging scan (RF & gradient pulse sequence and data acquisition) is repeated at a constant rate for a predetermined number of times and the data averaged. The signal amplitude recorded for any given scan is proportional to the number of spins that have decayed back to equilibrium since the previous scan. Thus, regions with rapidly decaying spins (i.e. short $T_1$ values) will recover all of their signal amplitude between successive scans.

The measured intensities in the final image will accurately reflect the spin density (i.e. water content). Regions with long $T_1$ values compared to the time between scans will progressively lose signal until a steady state condition is reached and will appear as darker regions in the final image. Changes in $T_2$ (spin-spin relaxation time) result in changes in the signal linewidth (shorter $T_2$ values) yielding larger linewidths. In extreme situations the linewidth can be so large that the signal is indistinguishable from background noise. In clinical imaging, water relaxation characteristics vary from tissue to tissue, providing the contrast which allows the discrimination of tissue types. Moreover, the MRI experiment can be setup so that regions of the sample with short $T_1$ values and/or long $T_2$ values are preferentially enhanced so called $T_1$-weighted and $T_2$-weighted imaging protocol.

MRI Contrast Agents.

There is a rapidly growing body of literature demonstrating the clinical effectiveness of paramagnetic contrast agents (currently 8 are in clinical trials or in use). The capacity to differentiate regions/tissues that may be magnetically similar but histologically distinct is a major impetus for the preparation of these agents [1, 2]. In the design of MRI agents, strict attention must be given to a variety of properties that will ultimately effect the physiological outcome apart from the ability to provide contrast enhancement [3]. Two fundamental properties that must be considered are biocompatability and proton relaxation enhancement. Biocompatability is influenced by several factors including toxicity, stability (thermodynamic and kinetic), pharmacokinetics and biodistribution. Proton relaxation enhancement (or relaxivity) is chiefly governed by the choice of metal and rotational correlation times.

The first feature to be considered during the design stage is the selection of the metal atom, which will dominate the measured relaxivity of the complex. Paramagnetic metal ions, as a result of their unpaired electrons, act as potent relaxation enhancement agents. They decrease the $T_1$ and $T_2$ relaxation times of nearby ($r^6$ dependence) spins. Some paramagnetic ions decrease the $T_1$ without causing substantial linebroadening (e.g. gadolinium (III), ($Gd^{3+}$)), while others induce drastic linebroadening (e.g. superparamagnetic iron oxide). The mechanism of $T_1$ relaxation is generally a through space dipole—dipole interaction between the unpaired electrons of the paramagnet (the metal atom with an unpaired electron) and bulk water molecules (water molecules that are not "bound" to the metal atom) that are in fast exchange with water molecules in the metal's inner coordination sphere (are bound to the metal atom).

For example, regions associated with a $Gd^{3+}$ ion (near-by water molecules) appear bright in an MR image where the normal aqueous solution appears as dark background if the time between successive scans in the experiment is short (i.e. $T_1$ weighted image). Localized $T_2$ shortening caused by superparamagnetic particles is believed to be due to the local magnetic field inhomogeneities associated with the large magnetic moments of these particles. Regions associated with a superparamagnetic iron oxide particle appear dark in an MR image where the normal aqueous solution appears as high intensity background if the echo time (TE) in the spin-echo pulse sequence experiment is long (i.e. $T_2$-weighted image). The lanthanide atom $Gd^{3+}$ is by the far the most frequently chosen metal atom for MRI contrast agents because it has a very high magnetic moment ($u^2$= 63$BM^2$), and a symmetric electronic ground state, ($S^8$). Transition metals such as high spin Mn(II) and Fe(III) are also candidates due to their high magnetic moments.

Once the appropriate metal has been selected, a suitable ligand or chelate must be found to render the complex nontoxic. The term chelator is derived from the Greek word chele which means a "crabs claw", an appropriate description for a material that uses its many "arms" to grab and hold on to a metal atom (see DTPA below). Several factors influence the stability of chelate complexes include enthalpy and entropy effects (e.g. number, charge and basicity of coordinating groups, ligand field and conformational effects). Various molecular design features of the ligand can be directly correlated with physiological results. For example, the presence of a single methyl group on a given ligand structure can have a pronounced effect on clearance rate. While the addition of a bromine group can force a given complex from a purely extracellular role to an effective agent that collects in hepatocytes.

Diethylenetriaminepentaacetic (DTPA) chelates and thus acts to detoxify lanthanide ions. The stability constant (K) for Gd(DTPA)$^{2-}$ is very high (logK=22.4) and is more commonly known as the formation constant (the higher the logK, the more stable the complex). This thermodynamic parameter indicates the fraction of Gd$^{3+}$ ions that are in the unbound state will be quite small and should not be confused with the rate (kinetic stability) at which the loss of metal occurs ($k_f/k_d$). The water soluble Gd(DTPA)$^{2-}$ chelate is stable, nontoxic, and one of the most widely used contrast enhancement agents in experimental and clinical imaging research. It was approved for clinical use in adult patients in June of 1988. It is an extracellular agent that accumulates in tissue by perfusion dominated processes.

To date, a number of chelators have been used, including diethylenetriaminepentaacetic (DTPA), 1,4,7,10-tetraazacyclododecane'-N,N'N'',N'''-tetracetic acid (DOTA), and derivatives thereof. See U.S. Pat. Nos. 5,155,215, 5,087,440, 5,219,553, 5,188,816, 4,885,363, 5,358,704, 5,262,532, and Meyer et al., Invest. Radiol. 25: S53 (1990).

Image enhancement improvements using Gd(DTPA) are well documented in a number of applications (Runge et al., Magn, Reson. Imag. 3:85 (1991); Russell et al., AJR 152:813 (1989); Meyer et al., Invest. Radiol. 25:S53 (1990)) including visualizing blood-brain barrier disruptions caused by space occupying lesions and detection of abnormal vascularity. It has recently been applied to the functional mapping of the human visual cortex by defining regional cerebral hemodynamics (Belliveau et al., (1991) 254:719).

Another chelator used in Gd contrast agents is the macrocyclic ligand 1,4,7,10-tetraazacyclododecane-N,N',N''N'''-tetracetic acid (DOTA). The Gd-DOTA complex has been thoroughly studied in laboratory tests involving animals and humans. The complex is conformationally rigid, has an extremely high formation constant (logK=28.5), and at physiological pH possess very slow dissociation kinetics. Recently, the GdDOTA complex was approved as an MRI contrast agent for use in adults and infants in France and has been administered to over 4500 patients.

As noted above, these MRI contrast agents have a variety of uses. However, there are no MRI contrast agents that report on physiologic or metabolic processes within a biological or other type of sample. Accordingly, it is an object of the present invention to provide MRI contrast or enhancement agents which allow the visualization and detection of physiological agents within an animal, tissue or cells.

SUMMARY OF THE INVENTION

In accordance with the above objects, the invention provides MRI agents comprising a paramagnetic metal ion bound to a complex. The complex comprises a chelator and a blocking moiety in at least a first coordination sites of said metal ion. The blocking moiety is covalently attached to the chelator, and capable of interacting with a target substance such that the exchange of water in at least said first coordination site in the metal ion complex is altered.

In one aspect, the invention provides MRI agents comprising a) a Gd(III) ion bound to a chelator such that the Gd(III) ion has coordination atoms in at least 5 coordination sites, and b) a blocking moiety covalently attached to the chelator which hinders the rapid exchange of water in the remaining coordination sites. The blocking moiety is capable of interacting with a target substance such that the exchange of water in the remaining coordination sites is increased.

In an additional aspect, the invention provides MRI agents having the formula:

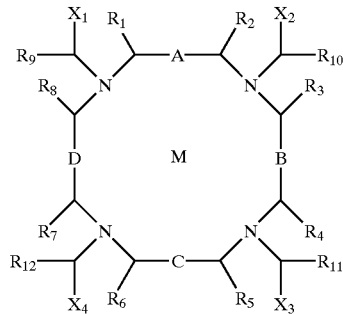

wherein

M is a paramagnetic metal ion selected from the group consisting of Gd(III), Fe(III), Mn(II), Yt(III), Cr(III) and Dy(III);

A, B, C and D are either single bonds or double bonds;

$X_1$, $X_2$, $X_3$ and $X_4$ are —OH, —COO—, —CH$_2$OH—CH$_2$COO—, or a blocking moiety;

$R_1$–$R_{12}$ are hydrogen, alkyl, aryl, phosphorus moiety, or a blocking moiety;

wherein at least one of $X_1$–$X_4$ and $R_1$–$R_{12}$ is a blocking moiety.

In a further aspect, the invention provides MRI contrast agents comprising a first paramagnetic metal ion bound to a first complex, and at least a second paramagnetic metal ion bound to a second complex. The first and second complexes each comprise a chelator with a covalently attached blocking moiety. The complexes can be attached via a linker, for example a polymer.

In an additional aspect, the MRI agent comprise a) a first chelator comprising a first paramagnetic metal ion; b) a second chelator comprising a second paramagnetic metal ion; and c) a blocking moiety covalently attached to at least one of the first or second chelators. The blocking moiety provides at least a first coordination atom of each of the first and second metal ions, or serves as a coordination site barrier. As above, the blocking moiety is capable of interacting with a target substance such that the exchange of water in at least a first coordination site of at least one of the metal ions is increased.

The invention also provides methods of magnetic resonance imaging of a cell, tissue, experimental animal or patient comprising administering an MRI agent of the invention to a cell, tissue, experimental animal or patient and rendering a magnetic resonance image of said cell, tissue, experimental animal or patient.

BRIEF DESCRIPTION OF THE DRAWINGS

FIG. 1 depicts a representative complex of the invention, where the blocking moiety is tethered at one end only. The blocking moiety comprises a enzyme substrate and a coordination site barrier. The R group is the coordination site barrier.

FIG. 2 depicts a representative complex of the invention, wherein the blocking moiety is tethered at two ends. The R group is the coordination site barrier.

FIG. 3 depicts a representative synthesis of Do3a-hydroxyethyl-β-galactose, which has a single galactose moiety attached to the DOTA ring.

FIG. 4 depicts a representative synthesis of a β-galactose-DOTA derivative that has two galactose moieties attached to the DOTA ring.

FIG. 5 depicts the synthesis of a BAPTA-DOTA derivative.

FIG. 6 depicts the syntheis of a FURA-DOTA derivative.

FIG. 7 depicts a synthetic scheme for the synthesis of BAPTA-DTPA.

FIG. 8 depicts an alternative synthesis of a BAPTA-DTPA derivative.

FIG. 9 depicts the change in $T_1$ observed upon the β-galactosidase catalyzed cleavage of the galactopyranose residue (n=3). The first Column of each pair (1,3,5) represents the $T_1$ of the galactose-DOTA complex and β-galactosidase mixture immediately after addition. The second column represents the $T_1$ of the solution after a period of time in the presence of β-galactosidase. Each column is reported as a ratio to a control containing only the complex. Column 1 and 2: 2.0 mM Gd complex plus 1.7 uM β-galactosidase phosphate buffer (25 mM) pH 7.3. Column 3 and 4: 2.0 mM Gd plus 5.1 uM β-galactosidase phosphate buffer (25 mM) pH 7.3. Column 5 and 6: 2 mM Gd complex plus 5.1 uM heat inactivated β-galactosidase (10 minutes at 80 degrees) phosphate buffer (25 mM) pH 7.3. The complexes were incubated with the enzyme for 7 days and HPLC traces indicated greater than 95% cleavage. A minimal concentration of enzyme was used in these experiments to reduce potential effects of any contrast agent-enzyme interactions. $T_1$ were carried out using a Bruker AMX 500 spectrometer at 26 degrees using a standard inversion-recovery sequence. The solution was placed in a 40 ul round bottomed NMR tube insert (Wilmad glass) and inserted into a tube containing $d_3$-chloroform. A two dimensional data file was collected containing 16 different inversion delays with 8 scans each. The raw nmr data was processed (Felix, BIOSYM/Molecular Simulations, San Diego, Calif.) and the peak heights were fitted to an exponential rise to a max to obtain $T_1$. The R value was always greater than 0.999.

FIGS. 10A, 10B, 10C, 10D, 10E, 10F, and 10G depict several of the possible conformations of the dimer embodiments. Boxes represent chelators, with M being the paramagnetic metal ions. FIGS. 10A and 10B represent two possible duplex conformations. In FIG. 10A, $R_{27}$ can be a linker, such as described herein as $R_{26}$, a cleavable moiety such as an enzyme substrate such as a peptide, or a blocking moiety that will preferentially interact with the target molecule. $R_{28}$, which may or may not be present depending on $R_{27}$, is a coordination site barrier similar to $R_{23}$ or a blocking moiety. FIG. 10B has $R_{28}$ blocking moieties or coordination site barriers attached via an $R_{27}$ group to two chelators. FIG. 10C is similar to FIG. 10A, but at least one of the $R_{27}$ groups must be a cleavable moiety. FIG. 10D depicts the case where two blocking moieties or coordination site barriers are present; if $R_{27}$ is a blocking moiety, $R_{28}$ need not be present. FIG. 10E is similar to 10B but the chelators need not be covalently attached. FIGS. 10F (single MRI agents) and and 10G (duplex agents) are multimers of MRI contrast agents, wherein n can be from 1 to 1000, with from 1 to about 20 being preferred, and from about 1 to 10 being especially preferred. FIGS. 10H and 10I depict polymer 10 as defined herein being attached to either single MRI agents (10H) or duplex MRI agents (10I).

FIGS. 11A, 11B and 11C depicts precursors for making MRI duplexes for $Ca^{+2}$ detection using BAPTA derivatives as the blocking moiety, each with a different $R_{26}$ linkers. FIG. 11A depicts AEPA, which when Gd is present exhibits a q of 0.7 (q is the number of water molecules associated with the complex, which is an indicator of the ability of the blocking moiety to block the exchange of water; the lower the q the better). The q values were determined using fluorescence lifetime measurements using Terbium ($Tb^{3+}$) as the metal ion in $D_2O$ and $H_2O$ (data not shown). FIG. 11B depicts APPA, which has a q of 0.3. FIG. 11C depicts ABPA, which has a q of 0.7.

FIG. 12 depicts the synthesis of AEPA. As will be appreciated by those in the art, the full duplex can be made by functionalizing the other ortho position on the nitrobenzyl ring.

FIG. 13 depicts the synthesis of APPA and ABPA. As will be appreciated by those in the art, the full duplexes can be made by functionalizing the other ortho position on the nitrobenzyl ring.

FIG. 14 depicts the synthesis of Gd3+-BAPTA-DO3A$_2$ ("CalGad").

FIG. 15 schematically depicts the structural changes in CalGad that occur upon binding of calcium.

FIG. 16 depicts the relaxivity of the CalGad complex as a function of calcium ion concentration.

FIG. 17 depicts MRI detection of β-galactosidase mRNA expression in living *Xenopus laevis* embryos. Background corrected MR images of two embryos injected with EGadMe at the 2-cell stage. The embryo on the right was also injected with β-gal mRNA, resulting in the higher intensity regions. The observed contrast enhancement makes it possible to recognize the eye, head, brachial arches, and somites of both embryos, but the signal strength is 45–65% greater in the embryo on the right containing β-gal (contrast-to-noise ratio ranges from 3.5 to 6). The cement gland has intrinsically short $T_1$, thus is visible as a bright structure on both embryos. d: dorsal; v: ventral; r: rostral; e: eye; c: cement gland; s: somite; b: brachial arches. Scale Bar=1 mm.

FIG. 18 depicts MRI detection of regions positive for β-galactosidase within a single living *Xenopus laevis* embryo. Embryos were injected at the 2-cell stage. Both cells received EGadMe; one cell also received mRNA for β-galactosidase. The 2 cells at this stage represent the future left and right sides of the animal. The head of embryo is to the left in all three panels. FIG. 18A depicts GFP fluorescence image of a living embryo. In this dorsal view, fluorescence is clearly localized to the right side of the embryo (top), although absent from the head, indicating the position of the descendants of the mRNA injected blastomere. FIG. 18B depicts MR image of the same living embryo depicted in A, with signal from water made transparent. The high intensity region on the right side indicates cleavage of EGadMe. Blocks of somites are visible on the right side. Labeling is present in the skin on both sides, with fainter label in the skin on the left side. MRI also visualizes internal regions of the animal rather than the surface-only views offered by light microscopy (A, C), and detects expression deep in the head that is not visible from the surface view offered by light microscopy. FIG. 18C depicts the same embryo stained for β-galactosidase after completion of the MR imaging. Whole-mount cytochemistry reveals that β-galactosidase is located primarily on the right side of the embryo, with less in the head, with some skin label toward the ventral half of the left side. The embryo curled slightly during fixation. Scale Bar=1 mm FIG. 19 demonstrates use of EGadMe for MR detection of lacZ gene expression. FIG. 19A depicts MR image of living embryo injected with plasmids carrying the lacZ gene. Plasmid carrying the lacZ gene was injected to one cell at the two-cell stage and subsequent enzyme expression was on the left side of the embryo as shown. Regions of high signal intensity are found in the bright stripe of endoderm (e), regions of the head (h) and ventrally, including two distinct spots (red arrows) found just ventral to the cement gland (c). FIG. 19B depicts bright field image of same embryo fixed and stained for β-galactosidase. Whole mount cytochemistry shows that regions demonstrating enzyme expression correlate with the regions of high intensity in the MR image.

FIGS. 20A, 20B, 20C, 20D and 20E depict several different linkers that are cleavable by esterases. FIG. 20A depicts schematic esterase enzyme mechanisms. FIGS. 20B, 20C, 20D and 20E depict several different linkers, using a blocking moiety, although as will be appreciated, other blocking moieties can be used as well.

FIG. 21 depicts a synthetic scheme for the synthesis of the compositions of the invention that have peptides as a component of the system (either as a blocking moiety, linker or targeting moiety, for example).

FIG. 22 depicts a representative structure utilizing a blocking moiety comprising a peptide and a HIV-TAT peptide as a targeting moiety, attached with an aryl amine linker, although as outlined herein, any number of different linkers may be used.

FIG. 23 depicts a variety of configurations for adding targeting moieties to the compositions of the invention.

DETAILED DESCRIPTION OF THE INVENTION

Figure 20C:
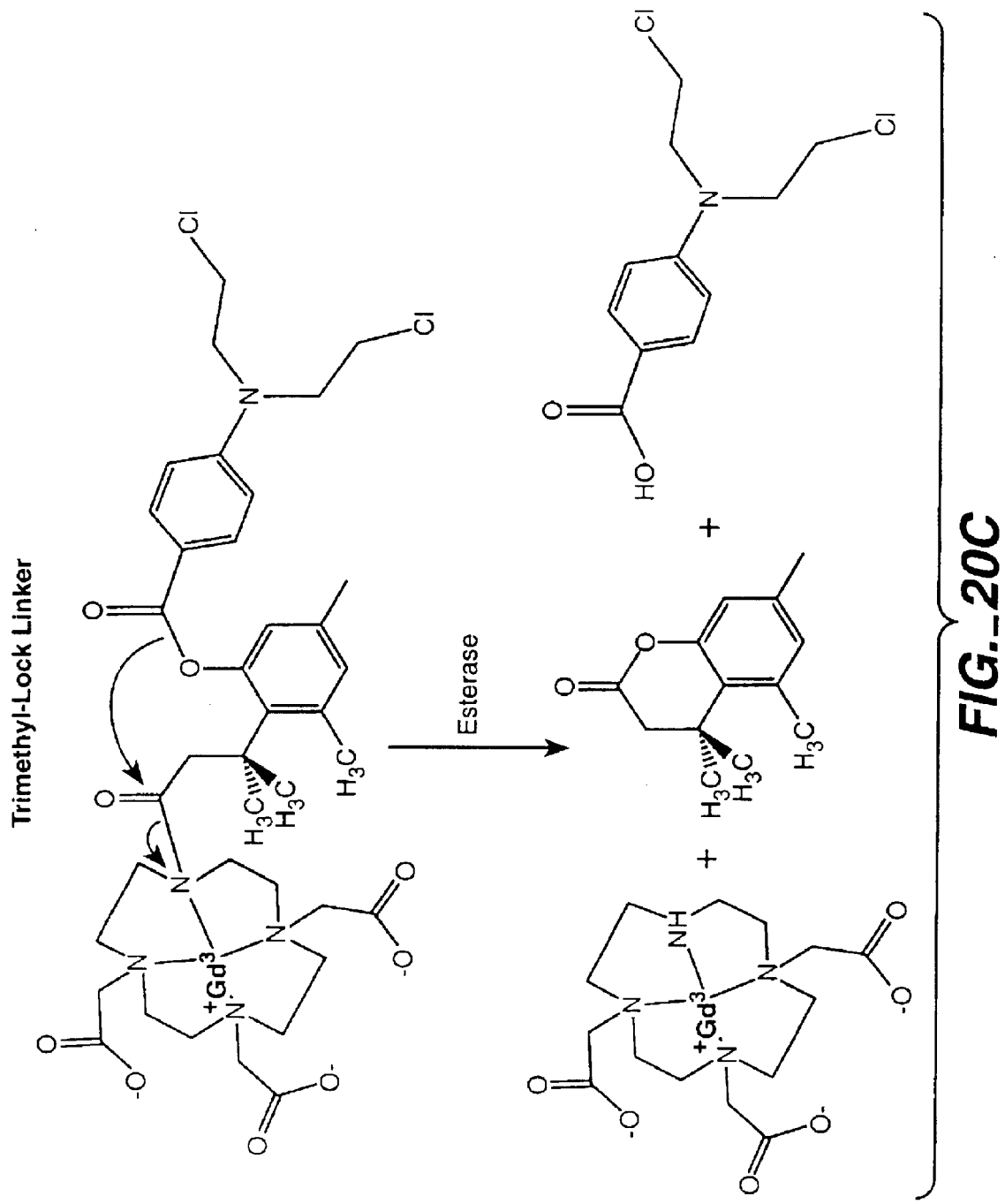

The present invention provides magnetic resonance imaging contrast agents which can detect physiological agents or target substances. The MRI agents of the invention are relatively inactive, or have weak relaxivity, as contrast enhancement agents in the absence of the physiological target substance, and are activated, thus altering the MR image, in the presence of the physiological target substance.

Viewed simplistically, this "trigger" mechanism, whereby the contrast agent is "turned on" (i.e. increases the relaxivity) by the presence of the target substance, is based on a dynamic equilibrium that affects the rate of exchange of water molecules in one or more coordination sites of a paramagnetic metal ion contained in the MRI contrast agents of the present invention. In turn, the rate of exchange of the water molecule is determined by the presence or absence of the target substance in the surrounding environment. Thus, in the absence of the target substance, the metal ion complexes of the invention which chelate the paramagnetic ion have reduced coordination sites available which can rapidly exchange with the water molecules of the local environment. In such a situation, the water coordination sites are substantially occupied or blocked by the coordination atoms of the chelator and at least one blocking moiety. Thus, the paramagnetic ion has essentially no water molecules in its "inner-coordination sphere", i.e. actually bound to the metal when the target substance is absent. It is the interaction of the paramagnetic metal ion with the protons on the inner coordination sphere water molecules and the rapid exchange of such water molecules that cause the high observed relaxivity, and thus the imaging effect, of the paramagnetic metal ion. Accordingly, if all the coordination sites of the metal ion in the metal ion complex are occupied with moieties other than water molecules, as is the case when the target substance is absent, there is little if any net enhancement of the imaging signal by the metal ion complexes of the invention. However, when present, the target substance interacts with the blocking moiety or moities of the metal ion complex, effectively freeing at least one of the inner-sphere coordination sites on the metal ion complex. The water molecules of the local environment are then available to occupy the inner-sphere coordination site or sites, which will cause an increase in the rate of exchange of water and relaxivity of the metal ion complex toward water thereby producing image enhancement which is a measure of the presence of the target substance.

Generally, a 2 to 5% change in the MRI signal used to generate the image is sufficient to be detectable. Thus, it is preferred that the agents of the invention in the presence of a target substance increase the MRI signal by at least 2 to 5% as compared to the signal gain the absence of the target substance. Signal enhancement of 2 to 90% is preferred, and 10 to 50% is more preferred for each coordination site made available by the target substance interaction with the blocking moiety. That is, when the blocking moiety occupies two or more coordination sites, the release of the blocking moiety can result in double the increase in signal or more as compared to a single coordination site.

It should be understood that even in the absence of the target substance, at any particular coordination site, there will be a dynamic equilibrium for one or more coordination sites as between a coordination atom of the blocking moiety and water molecules. That is, even when a coordination atom is tightly bound to the metal, there will be some exchange of water molecules at the site. However, in most instances, this exchange of water molecules is neither rapid nor significant, and does not result in significant image enhancement. However, upon exposure to the target substance, the blocking moiety dislodges from the coordination site and the exchange of water is increased, i.e. rapid exchange and therefore an increase in relaxivity may occur, with significant image enhancement.

The complexes of the invention comprise a chelator and a blocking moiety. The metal ion complexes of the invention comprise a paramagnetic metal ion bound to a complex comprising a chelator and a blocking moiety. By "paramagnetic metal ion", "paramagnetic ion" or "metal ion" herein is meant a metal ion which is magnetized parallel or antiparallel to a magnetic field to an extent proportional to the field. Generally, these are metal ions which have unpaired electrons; this is a term understood in the art. Examples of suitable paramagnetic metal ions, include, but are not limited to, gadolinium III (Gd+3 or Gd(III)), iron III (Fe+3 or Fe(III)), manganese II (Mn+2 or Mn(II)), yttrium III (Yt+3 or Yt(III)), dysprosium (Dy+3 or Dy(III)), and chromium (Cr(III) or Cr+3). In a preferred embodiment the paramagnetic ion is the lanthanide atom Gd(III), due to its high magnetic moment ($u^2$=63BM2), a symmetric electronic ground state (S8), and its current approval for diagnostic use in humans.

In addition to the metal ion, the metal ion complexes of the invention comprise a chelator and a blocking moiety which may be covalently attached to the chelator. Due to the relatively high toxicity of many of the paramagnetic ions, the ions are rendered nontoxic in physiological systems by binding to a suitable chelator. Thus, the substitution of blocking moieties in coordination sites of the chelator, which in the presence of the target substance are capable of vacating the coordination sites in favor of water molecules, may render the metal ion complex more toxic by decreasing the half-life of dissociation for the metal ion complex. Thus, in a preferred embodiment, only a single coordination site is occupied or blocked by a blocking moiety. However, for some applications, e.g. analysis of tissue and the like, the toxicity of the metal ion complexes may not be of paramount importance. Similarly, some metal ion complexes are so stable that even the replacement of one or more additional coordination atoms with a blocking moiety does not significantly effect the half-life of dissociation. For example, DOTA, described below, when complexed with Gd(III) is extremely stable. Accordingly, when DOTA serves as the chelator, several of the coordination atoms of the chelator may be replaced with blocking moieties without a significant increase in toxicity. Additionally such an agent would potentially produce a larger signal since it has two or more coordination sites which are rapidly exchanging water with the bulk solvent.

There are a variety of factors which influence the choice and stability of the chelate metal ion complex, including enthalpy and entropy effects (e.g. number, charge and basicity of coordinating groups, ligand field and conformational effects).

In general, the chelator has a number of coordination sites containing coordination atoms which bind the metal ion. The number of coordination sites, and thus the structure of the chelator, depends on the metal ion. The chelators used in the metal ion complexes of the present invention preferably have at least one less coordination atom (n-1) than the metal ion is capable of binding (n), since at least one coordination site of the metal ion complex is occupied or blocked by a blocking moeity, as described below, to confer functionality on the metal ion complex. Thus, for example, Gd(III) may have 8 strongly associated coordination atoms or ligands and is capable of weakly binding a ninth ligand. Accordingly, suitable chelators for Gd(III) will have less than 9 coordination atoms. In a preferred embodiment, a Gd(III) chelator will have 8 coordination atoms, with a blocking moiety either occupying or blocking the remaining site in the metal ion complex. In an alternative embodiment, the chelators used in the metal ion complexes of the invention have two less coordination atoms (n-2) than the metal ion is capable of binding (n), with these coordination sites occupied by one or more blocking moieties. Thus, alternative embodiments utilize Gd(III) chelators with at least 5 coordination atoms, with at least 6 coordination atoms being preferred, at least 7 being particularly preferred, and at least 8 being especially preferred, with the blocking moiety either occupying or blocking the remaining sites. It should be appreciated that the exact structure of the chelator and blocking moiety may be difficult to determine, and thus the exact number of coordination atoms may be unclear. For example, it is possible that the chelator provide a fractional or non-integer number of coordination atoms; i.e. the chelator may provide 7.5 coordination atoms, i.e. the 8th coordination atom is on average not fully bound to the metal ion. However, the metal ion complex may still be functional, if the 8th coordination atom is sufficiently bound to prevent the rapid exchange of water at the site, and/or the blocking moiety impedes the rapid exchange of water at the site.

There are a large number of known macrocyclic chelators or ligands which are used to chelate lanthanide and paramagnetic ions. See for example, Alexander, Chem. Rev. 95:273–342 (1995) and Jackels, Pharm. Med. Imag, Section III, Chap. 20, p645 (1990), expressly incorporated herein by reference, which describes a large number of macrocyclic chelators and their synthesis. Similarly, there are a number of patents which describe suitable chelators for use in the invention, including U.S. Pat. Nos. 5,155,215, 5,087,440, 5,219,553, 5,188,816, 4,885,363, 5,358,704, 5,262,532, and Meyer et al., Invest. Radiol. 25: S53 (1990), all of which are also expressly incorporated by reference. Thus, as will be understood by those in the art, any of the known paramagnetic metal ion chelators or lanthanide chelators can be easily modified using the teachings herein to further comprise at least one blocking moiety.

When the metal ion is Gd(III), a preferred chelator is 1,4,7,10-tetraazacyclododecane-N,N',N",N'''-tetracetic acid (DOTA) or substituted DOTA. DOTA has the structure shown below:

Structure 1

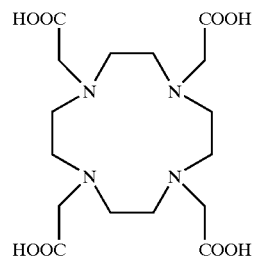

By "substituted DOTA" herein is meant that the DOTA may be substituted at any of the following positions, as shown below:

Structure 2

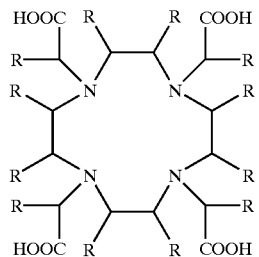

Suitable R substitution groups include a wide variety of groups, as will be understood by those in the art. For example, suitable substitution groups include substitution groups disclosed for DOTA and DOTA-type compounds in U.S. Pat. Nos. 5,262,532, 4,885,363, and 5,358,704. These groups include hydrogen, alkyl groups including substituted alkyl groups and heteroalkyl groups, aryl groups including substituted aryl and heteroaryl groups, phosphorus moieties, and blocking moieties. As will be appreciated by those skilled in the art, each position designated above may have two R groups attached (R' and R"), although in a preferred embodiment only a single non-hydrogen R group is attached at any particular position; that is, preferably at least one of the R groups at each position is hydrogen. Thus, if R is an alkyl or aryl group, there is generally an additional hydrogen attached to the carbon, although not depicted herein. In a preferred embodiment, one R group is a blocking moiety and the other R groups are hydrogen.

By "alkyl group" or grammatical equivalents herein is meant a straight or branched chain alkyl group, with straight chain alkyl groups being preferred. If branched, it may be branched at one or more positions, and unless specified, at any position. Also included within the definition of alkyl are heteroalkyl groups, wherein the heteroatom is selected from nitrogen, oxygen, phosphorus, sulfur and silicon. Also included within the definition of an alkyl group are cycloalkyl groups such as C5 and C6 rings, and heterocycloalkyl.

Additional suitable heterocyclic substituted rings are depicted in U.S. Pat. No. 5,087,440, expressly incorporated by reference. In some embodiments, two adjacent R groups may be bonded together to form ring structures together with the carbon atoms of the chelator, such as is described in U.S. Pat. No. 5,358,704, expressly incorporated by reference. These ring structures may be similarly substituted.

The alkyl group may range from about 1 to 20 carbon atoms (C1–C20), with a preferred embodiment utilizing from about 1 to about 10 carbon atoms (C1–C10), with about C1 through about C5 being preferred. However, in some embodiments, the alkyl group may be larger, for example when the alkyl group is the coordination site barrier.

By "alkyl amine" or grammatical equivalents herein is meant an alkyl group as defined above, substituted with an amine group at any position. In addition, the alkyl amine may have other substitution groups, as outlined above for alkyl group. The amine may be primary (—NH$_2$R), secondary (—NHR$_2$), or tertiary (—NR$_3$). When the amine is a secondary or tertiary amine, suitable R groups are alkyl groups as defined above. A preferred alkyl amine is p-aminobenzyl. When the alkyl amine serves as the coordination site barrier, as described below, preferred embodiments utilize the nitrogen atom of the amine as a coordination atom, for example when the alkyl amine includes a pyridine or pyrrole ring.

By "aryl group" or grammatical equivalents herein is meant aromatic aryl rings such as phenyl, heterocyclic aromatic rings such as pyridine, furan, thiophene, pyrrole, indole and purine, and heterocyclic rings with nitrogen, oxygen, sulfur or phosphorus.

Included within the definition of "alkyl" and "aryl" are substituted alkyl and aryl groups. That is, the alkyl and aryl groups may be substituted, with one or more substitution groups. For example, a phenyl group may be a substituted phenyl group. Suitable substitution groups include, but are not limited to, halogens such as chlorine, bromine and fluorine, amines, hydroxy groups, carboxylic acids, nitro groups, carbonyl and other alkyl and aryl groups as defined herein. Thus, arylalkyl and hydroxyalkyl groups are also suitable for use in the invention. Preferred substitution groups include alkyl amines and alkyl hydroxy.

By "phosphorous moieties" herein is meant moieties containing the —PO(OH)(R$_{25}$)$_2$ group. The phosphorus may be an alkyl phosphorus; for example, DOTEP utilizes ethylphosphorus as a substitution group on DOTA. R$_{25}$ may be alkyl, substituted alkyl, hydroxy. A preferred embodiment has a —PO(OH)$_2$R$_{25}$ group.

The substitution group may also be hydrogen or a blocking moiety, as is described below.

In an alternative embodiment, when the metal ion is Gd(III), a preferred chelator is below:

Structure 3

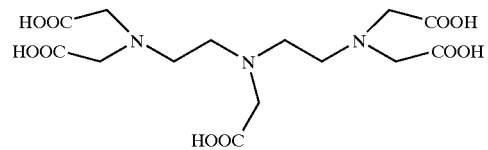

By "substituted DPTA" herein is meant that the DPTA may be substituted at any of the following positions, as shown below:

Structure 4

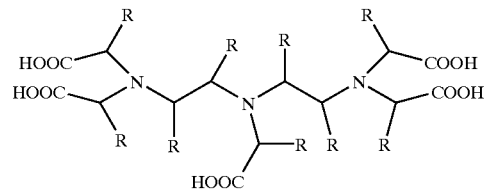

See for example U.S. Pat. No. 5,087,440.

Suitable R substitution groups include those outlined above for DOTA. Again, those skilled in the art will appreciate that there may be two R groups (R' and R") at each position designated above, although as described herein, at least one of the groups at each position is hydrogen, which is generally not depicted herein.

In an alternative embodiment, when the metal ion is Gd(III), a preferred chelator is 1,4,7,10-tetraazacyclododecane-N,N',N",N'''-tetraethylphosphorus (DOTEP) or substituted DOTEP (see U.S. Pat. No. 5,188,816). DOTEP has the structure shown below:

Structure 5

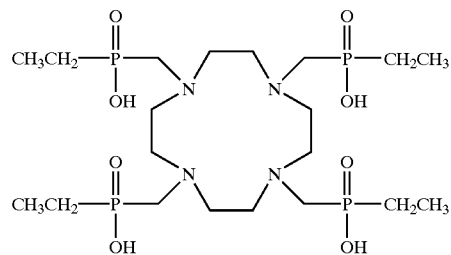

DOTEP may have similar R substitution groups as outlined above.

Other suitable Gd(III) chelators are described in Alexander, supra, Jackels, supra, U.S. Pat. Nos. 5,155,215, 5,087,440, 5,219,553, 5,188,816, 4,885,363, 5,358,704, 5,262,532, and Meyer et al., Invest. Radiol. 25: S53 (1990), among others.

When the paramagnetic ion is Fe(III), appropriate chelators will have less than 6 coordination atoms, since Fe(III) is capable of binding 6 coordination atoms. Suitable chelators for Fe(III) ions are well known in the art, see for example Lauffer et al., J. Am. Chem. Soc. 109:1622 (1987); Lauffer, Chem. Rev. 87:901–927 (1987); and U.S. Pat. Nos. 4,885,363, 5,358,704, and 5,262,532, all which describe chelators suitable for Fe(III).

When the paramagnetic ion is Mn(II) (Mn+2), appropriate chelators will have less than 5 or 6 coordination atoms, since Mn(II) is capable of binding 6 or 7 coordination atoms. Suitable chelators for Mn(II) ions are well known in the art; see for example Lauffer, Chem. Rev. 87:901–927 (1987) and U.S. Pat. Nos. 4,885,363, 5,358,704, and 5,262,532.

When the paramagnetic ion is Yt(III), appropriate chelators will have less than 7 or 8 coordination atoms, since Yt(III) is capable of binding 8 or 9 coordination atoms. Suitable chelators for Yt(III) ions include, but are not limited to, DOTA and DPTA and derivatives thereof (see Moi et al., J. Am. Chem. Soc. 110:6266–6267 (1988)) and those chelators described in U.S. Pat. No. 4,885,363 and others, as outlined above.

When the paramagnetic ion is Dy+3 (Dy(III)), appropriate chelators will have less than 7 or 8 coordination atoms, since DyIII is capable of binding 8 or 9 coordination atoms. Suitable chelators are known in the art, as above.

In a preferred embodiment, the chelator and the blocking moiety are covalently linked; that is, the blocking moiety is a substitution group on the chelator. In this embodiment, the substituted chelator, with the bound metal ion, comprises the metal ion complex which in the absence of the target substance has all possible coordination sites occupied or blocked; i.e. it is coordinatively saturated.

In an alternative embodiment, the chelator and the blocking moiety are not covalently attached. In this embodiment, the blocking moiety has sufficient affinity for the metal ion to prevent the rapid exchange of water molecules in the absence of the target substance. However, in this embodiment the blocking moiety has a higher affinity for the target substance than for the metal ion. Accordingly, in the presence of the target substance, the blocking moiety will have a tendency to be dislodged from the metal ion to interact with the target substance, thus freeing up a coordination site in the metal ion complex and allowing the rapid exchange of water and an increase in relaxivity.

What is important is that the metal ion complex, comprising the metal ion, the chelator and the blocking moiety, is not readily able to rapidly exchange water molecules when the blocking moeities are in the inner coordination sphere of the metal ion, such that in the absence of the target substance, there is less or little substantial image enhancement.

By "blocking moiety" or grammatical equivalents herein is meant a functional group associated with the chelator metal ion complexes of the invention which is capable of interacting with a target substance and which is capable, under certain circumstances, of substantially blocking the exchange of water in at least one inner coordination site of the metal ion of the metal ion complex. For example, when bound to or associated with the metal ion complexes of the invention, the blocking moiety occupies or blocks at least one coordination site of the metal ion in the absence of the target substance. Thus, the metal ion is coordinately saturated with the chelator and the blocking moiety or moieties in the absence of the target substance.

A blocking moiety may comprise several components. The blocking moiety has a functional moiety which is capable of interacting with a target substance, as outlined below. This functional moiety may or may not provide the coordination atom(s) of the blocking moiety. In addition, blocking moieties may comprise one or more linker groups to allow for correct spacing and attachment of the components of the blocking moiety. Furthermore, in the embodiment where the functional group of the blocking moiety does not contribute a coordination atom, the blocking moiety may comprise a coordination site barrier, which serves to either provide a coordination site atom or sterically prevent the rapid exchange of water at the coordination site; i.e. the coordination site barrier may either occupy or block the coordination site.

By "capable of interacting with a target substance" herein is meant that the blocking moiety has an affinity for the target substance, such that the blocking moiety will stop blocking or occupying at least one coordination site of the metal ion complex when the target substance is present. Thus, as outlined above, the blocking moiety is blocking or occupying at least one coordination site of the metal ion in the absence of the target substance. However, in the presence of the target substance, the blocking moiety associates or interacts with the target substance and is released from its association with the metal ion, thus freeing at least one coordination site of the metal ion such that the rapid exchange of water can occur at this site, resulting in image enhancement.

The nature of the interaction between the blocking moiety and the target substance will depend on the target substance to be detected or visualized via MRI. For example, suitable target substances include, but are not limited to, enzymes; proteins; peptides; nucleic acids; ions such as Ca+2, Mg+2, Zn+2, K+, Cl−, and Na+; cAMP; receptors such as cell-surface receptors and ligands; hormones; antigens; antibodies; ATP; NADH; NADPH; $FADH_2$; $FNNH_2$; coenzyme A (acyl CoA and acetyl CoA); and biotin, among others.

In some embodiments, the nature of the interaction is irreversible, such that the blocking moiety does not reassociate to block or occupy the coordination site; for example, when the blocking moiety comprises an enzyme substrate which is cleaved upon exposure to the target enzyme. Alternatively, the nature of the interaction is reversible, such that the blocking moiety will reassociate with the complex to hinder the exchange of water; for example, when the blocking moiety comprises an ion ligand, or a receptor ligand, as outlined below.

The corresponding blocking moieties will be enzyme substrates or inhibitors, receptor ligands, antibodies, antigens, ion binding compounds, substantially complementary nucleic acids, nucleic acid binding proteins, etc.

In a preferred embodiment, the target substance is an enzyme, and the blocking moiety is an enzyme substrate. In this embodiment, the blocking moiety is cleaved from the metal ion complex of the invention, allowing the exchange of water in at least one coordination site of the metal ion complex. This embodiment allows the amplification of the image enhancement since a single molecule of the target substance is able to generate many activated metal ion complexes, i.e. metal ion complexes in which the blocking moiety is no longer occupying or blocking a coordination site of the metal ion.

As will be appreciated by those skilled in the art, the possible enzyme target substances are quite broad. The target substance enzyme may be chosen on the basis of a correlation to a disease condition, for example, for diagnositic purposes. Alternatively, the metal ion complexes of the present invention may be used to establish such correlations.

Suitable classes of enzymes include, but are not limited to, hydrolases such as proteases, carbohydrases, lipases and nucleases; isomerases such as racemases, epimerases, tautomerases, or mutases; transferases, kinases and phophatases.

As will be appreciated by those skilled in the art, the potential list of suitable enzyme targets is quite large. Enzymes associated with the generation or maintenance of arterioschlerotic plaques and lesions within the circulatory system, inflammation, wounds, immune response, tumors, may all be detected using the present invention. Enzymes such as lactase, maltase, sucrase or invertase, cellulase, α-amylase, aldolases, glycogen phosphorylase, kinases such as hexokinase, proteases such as serine, cysteine, aspartyl and metalloproteases may also be detected, including, but not limited to, trypsin, chymotrypsin, and other therapeutically relevant serine proteases such as tPA and the other proteases of the thrombolytic cascade; cysteine proteases including: the cathepsins, including cathepsin B, L, S, H, J, N and O; and calpain; metalloproteinases including MMP-1 through MMP-10, particularly MMP-1, MMP-2, MMP-7 and MMP-9; and caspases, such as caspase-3, -5, -8 and other caspases of the apoptotic pathway, and interleukin-converting enzyme (ICE). Similarly, bacterial and viral infections may be detected via characteristic bacterial and viral enzymes. As will be appreciated in the art, this list is not meant to be limiting.

Once the target enzyme is identified or chosen, enzyme substrate blocking moieties can be designed using well known parameters of enzyme substrate specificities.

For example, when the enzyme target substance is a protease, the blocking moiety may be a peptide or polypeptide which is capable of being cleaved by the target protease. By "peptide" or "polypeptide" herein is meant a compound of about 2 to about 15 amino acid residues covalently linked by peptide bonds. Preferred embodiments utilize polypeptides from about 2 to about 8 amino acids, with about 2 to about 4 being the most preferred. Preferably, the amino acids are naturally occurring amino acids, although amino acid analogs and peptidomimetic structures are also useful. Under certain circumstances, the peptide may be only a single amino acid residue.

Preferred target substance/peptide blocking moiety pairs include, but are not limited to, cat B and GGGF (SEQ ID NO: 1); cat B and GFQGVQFAGF (SEQ ID NO: 2); cat B and GFGSVGFAGF (SEQ ID NO: 3); cat B and GLVG-GAGAGF (SEQ ID NO: 4); cat B and GGFLGLGAGF (SEQ ID NO: 5); cat D and GFGSTFFAGF (SEQ ID NO: 6); caspase-3 and DEVD (SEQ ID NO: 7); MMP-7 and PELR (SEQ ID NO: 8); MMP-7 and PLGLAR (SEQ ID NO: 9); MMP-7 and PGLWA-(D-arg) (SEQ ID NO: 10); MMP-7 and PMALWMR (SEQ ID NO: 11); and MMP-7 and PMGLRA (SEQ ID NO: 12).

Similarly, when the enzyme target substance is a carbohydrase, the blocking moiety will be a carbohydrate group which is capable of being cleaved by the target carbohydrase. For example, when the enzyme target is lactase or β-galactosidase, the enzyme substrate blocking moiety is lactose or galactose. Similar enzyme/blocking moiety pairs include sucrase/sucrose, maltase/maltose, and α-amylase/amylose. In addition, the addition of carbohydrate moieties such as galactose, outlined herein, can alter the biodistribution of the agents; for example, the galactose blocking moieties outlined herein cause concentration in liver, kidneys and spleen.

In another embodiment, the blocking moiety may be an enzyme inhibitor, such that in the presence of the enzyme, the inhibitor blocking moiety disassociates from the metal ion complex to interact or bind to the enzyme, thus freeing an inner coordination sphere site of the metal ion for interaction with water. As above, the enzyme inhibitors are chosen on the basis of the enzyme target substance and the corresponding known characteristics of the enzyme.

In a preferred embodiment, the blocking moiety is a phosphorus moiety, as defined above, such as—(OPO(OR$_2$))$_n$, wherein n is an integer from 1 to about 10, with from 1 to 5 being preferred and 1 to 3 being particularly preferred. Each R is independently hydrogen or a substitution group as defined herein, with hydrogen being preferred. This embodiment is particularly useful when the target molecule is alkaline phosphatase or a phosphodiesterase, or other enzymes known to cleave phosphorus containing moieties such as these.

In one embodiment, the blocking moiety is a nucleic acid. The nucleic acid may be single-stranded or double stranded, and includes nucleic acid analogs such as peptide nucleic acids and other well-known modifications of the ribose-phosphate backbone, such as phosphorthioates, phosphoramidates, morpholino structures, etc. The target molecule can be a substantially complementary nucleic acid or a nulceic acid binding moiety, such as a protein.

In a preferred embodiment, the target substance is a physiological agent. As for the enzyme/substrate embodiment, the physiological agent interacts with the blocking moiety of the metal ion complex, such that in the presence of the physiological agent, there is rapid exchange of water in at least one inner sphere coordination site of the metal ion complex. Thus, the target substance may be a physiologically active ion, and the blocking moiety is an ion binding ligand. For example, as shown in the Examples, the target substance may be the Ca+2 ion, and the blocking moiety may be a calcium binding ligand such as is known in the art (see Grynkiewicz et al., J. Biol. Chem. 260(6):3440–3450 (1985); Haugland, R. P., Molecular Probes Handbook of Fluorescent Probes and Research Chemicals (1989–1991)). Other suitable target ions include Mn+2, Mg+2, Zn+2, Na+, and Cl−.

When Ca+2 is the target substance, preferred blocking moieties include, but are not limited to, the acetic acid groups of bis(o-amino-phenoxy)ethane-N,N,N',N'-tetraacetic acid (BAPTA), ethylene glycol bis(β-aminoethyl ether)-N,N,N',N'-tetraacetic acid (EGTA); ethylenediamine-tetracetic acid (EDTA); and derivatives thereof, such as disclosed in Tsien, Biochem. 19:2396–2404 (1980). Other known chelators of Ca+2 and other divalent ions, such as quin2 (2-[[2-[bis(carboxymethyl)amino]-5-methylphenoxy]methyl-6-methoxy-8-[bis(carboxymethyl)amino]quinoline; fura-1, fura-2, fura-3, stil-1, stil-2 and indo-1 (see Grynkiewicz et al., supra).

As for the enzyme/substrate embodiments, the metabolite may be associated with a particular disease or condition within an animal. For example, as outlined below, BAPTA-DOTA derivatives may be used to diagnose Alzeheimer's disease and other neurological disorders.

In a preferred embodiment, the blocking moiety is a ligand for a cell-surface receptor or is a ligand which has affinity for a extracellular component. In this embodiment, as for the physiological agent embodiment, the ligand has sufficient affinity for the metal ion to prevent the rapid exchange of water molecules in the absence of the target substance. Alternatively, there may be R groups "locking" the ligand into place, as described herein, resulting in either the contribution of a coordination atom or that the ligand serves as a coordination site barrier. In this embodiment ligand blocking moiety has a higher affinity for the target substance than for the metal ion. Accordingly, in the presence of the target substance, the ligand blocking moiety will interact with the target substance, thus freeing up at least one coordination site in the metal ion complex and allowing the rapid exchange of water and an increase in relaxivity. Additionally, in this embodiment, this may result in the accumulation of the MRI agent at the location of the target, for example at the cell surface. This may be similar to the situation where the blocking moiety is an enzyme inhibitor, as well.

In a preferred embodiment, the blocking moiety is a photocleavable moiety. That is, upon exposure to a certain wavelength of light, the blocking moiety is cleaved, allowing an increase in the exchange rate of water in at least one coordination site of the complex. This embodiment has particular use in developmental biology fields (cell lineage, neuronal development, etc.), where the ability to follow the fates of particular cells is desirable. Suitable photocleavable moieties are similar to "caged" reagents which are cleaved upon exposure to light. A particularly preferred class of photocleavable moieties are the O-nitrobenzylic compounds, which can be synthetically incorporated into a blocking moiety via an ether, thioether, ester (including phosphate esters), amine or similar linkage to a heteroatom (particularly oxygen, nitrogen or sulfur). Also of use are benzoin-based photocleavable moieties. A wide variety of suitable photocleavable moieties is outlined in the Molecular Probes Catalog, supra.

In a preferred embodiment, the compounds have a structure depicted below in Structure 18, which depicts a nitrobenzyl photocleavable group, although as will be appreciated by those in the art, a wide variety of other moieties may be used:

Structure 18

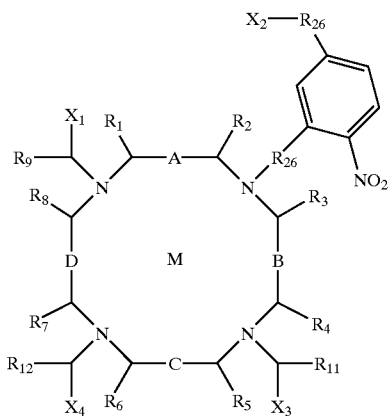

Structure 18 depicts a DOTA-type chelator, although as will be appreciated by those in the art, other chelators may be used as well. $R_{26}$ is a linker as defined below. Similarly, the $X_2$ group may be as defined above, although additional structures may be used, for example a coordination site barrier as outlined herein. Similarly, there may be substitutent groups on the aromatic ring, as is known in the art.

The blocking moiety itself may block or occupy at least one coordination site of the metal ion. That is, one or more atoms of the blocking moiety (i.e. the enzyme substrate, ligand, moiety which interacts with a physiological agent, photocleavable moiety, etc.) itself serves as a coordination atom, or otherwise blocks access to the metal ion by steric hinderance. For example, it appears that one or more of the atoms of the galactose blocking moiety outlined in the Examples may be direct coordination atoms for the Gd(III) metal ion. Similarly, peptide based blocking moieties for protease targets may contribute coordination atoms.

In an alternative embodiment, the blocking moiety further comprises a "coordination site barrier" which is covalently tethered to the complex in such a manner as to allow disassociation upon interaction with a target substance. For example, it may be tethered by one or more enzyme substrate blocking moieties. In this embodiment, the coordination site barrier blocks or occupies at least one of the coordination sites of the metal ion in the absence of the target enzyme substance. Coordination site barriers are used when coordination atoms are not provided by the functional portion of the blocking moiety, i.e. the component of the blocking moiety which interacts with the target substance. The blocking moiety or moieties such as an enzyme substrate serves as the tether, covalently linking the coordination site barrier to the metal ion complex. In the presence of the enzyme target, the enzyme cleaves one or more of the enzyme substrates, either within the substrate or at the point of attachment to the metal ion complex, thus freeing the coordination site barrier. The coordination site or sites are no longer blocked and the bulk water is free to rapidly exchange at the coordination site of the metal ion, thus enhancing the image. As will be appreciated by those in the art, a similar result can be accomplished with other types of blocking moieties.

In one embodiment, the coordination site barrier is attached to the metal ion complex at one end, as is depicted in FIG. 1. When the enzyme target cleaves the substrate blocking moiety, the coordination site barrier is released. In another embodiment, the coordination site barrier is attached to the metal ion complex with more than one substrate blocking moiety, as is depicted in FIG. 2 for two attachments. The enzyme target may cleave only one side, thus removing the coordination site barrier and allowing the exchange of water at the coordination site, but leaving the coordination site barrier attached to the metal ion complex. Alternatively, the enzyme may cleave the coordination site barrier completely from the metal ion complex.

In a preferred embodiment, the coordination site barrier occupies at least one of the coordination sites of the metal ion. That is, the coordination site barrier contains at least one atom which serves as at least one coordination atom for the metal ion. In this embodiment, the coordination site barrier may be a heteroalkyl group, such as an alkyl amine group, as defined above, including alkyl pyridine, alkyl pyrroline, alkyl pyrrolidine, and alkyl pyrole, or a carboxylic or carbonyl group. The portion of the coordination site barrier which does not contribute the coordination atom may also be consider a linker group. Preferred coordination site barriers are depicted in FIG. 2.

In an alternative embodiment, the coordination site barrier does not directly occupy a coordination site, but instead blocks the site sterically. In this embodiment, the coordination site barrier may be an alkyl or substituted group, as defined above, or other groups such as peptides, proteins, nucleic acids, etc.

In this embodiment, the coordination site barrier is preferrably linked via two enzyme substrates to opposite sides of the metal ion complex, effectively "stretching" the coordination site barrier over the coordination site or sites of the metal ion complex, as is depicted in FIG. 2.

In some embodiments, the coordination site barrier may be "stretched" via an enzyme substrate on one side, covalently attached to the metal ion complex, and a linker moeity, as defined below, on the other. In an alternative embodiment, the coordination site barrier is linked via a single enzyme substrate on one side; that is, the affinity of the coordination site barrier for the metal ion is higher than that of water, and thus the blocking moiety, comprising the coordination site barrier and the enzyme substrate, will block or occupy the available coordination sites in the absence of the target enzyme.

In some embodiments, the metal ion complexes of the invention have a single associated or bound blocking moiety. In such embodiments, the single blocking moiety impedes the exchange of water molecules in at least one coordination site. Alternatively, as is outlined below, a single blocking moiety may hinder the exchange of water molecules in more than one coordination site, or coordination sites on different chelators.

In alternative embodiments, two or more blocking moieties are associated with a single metal ion complex, to implede the exchange of water in at least one or more coordination sites.

It should be appreciated that the blocking moieties of the present invention may further comprise a linker group as well as a functional blocking moiety. That is, blocking moieties may comprise functional blocking moieties in combination with a linker group and/or a coordination site barrier.

Linker groups (sometimes depicted herein as $R_{26}$) will be used to optimize the steric considerations of the metal ion complex. That is, in order to optimize the interaction of the blocking moiety with the metal ion, linkers may be introduced to allow the functional blocking moiety to block or occupy the coordination site. In general, the linker group is chosen to allow a degree of structural flexibility. For example, when a blocking moiety interacts with a physiological agent which does not result in the blocking moiety being cleaved from the complex, the linker must allow some movement of the blocking moiety away from the complex, such that the exchange of water at at least one coordination site is increased.

Generally, suitable linker groups include, but are not limited to, alkyl and aryl groups, including substituted alkyl and aryl groups and heteroalkyl (particularly oxo groups) and heteroaryl groups, including alkyl amine groups, as defined above. Preferred linker groups include p-aminobenzyl, substituted p-aminobenzyl, diphenyl and substituted diphenyl, alkyl furan such as benzylfuran, carboxy, and straight chain alkyl groups of 1 to 10 carbons in length. Particularly preferred linkers include p-aminobenzyl, methyl, ethyl, propyl, butyl, pentyl, hexyl, acetic acid, propionic acid, aminobutyl, p-alkyl phenols, 4-alkylimidazole. The selection of the linker group is generally done using well known molecular modeling techniques, to optimize the obstruction of the coordination site or sites of the metal ion. In addition, as outlined in the Examples, the length of this linker may be very important in order to achieve optimal results. As shown in FIG. 11, the length of the linker, i.e. the spacer between the chelator and the coordination atom(s) of the blocking moiety, contributes to the steric conformation and association of the coordination atoms with the metal ion, thus allowing excellent blocking of the metal ion by the blocking moiety.

In a preferred embodiment, a coordination site barrier can be attached by a cleavable linker as outlined herein. A preferred embodiment utilizes esterase linkages such as are generally depicted in FIG. 20. Esterase linkages are particularly preferred when the blocking moiety is attached via an "arm" of the chelate, as the product of an esterase reaction is a carboxylic acid, which thus allows the regeneration of a stable chelate (and, in the case of DOTA and DPTA, chelates that are approved for human use). Alternatively, cleavable peptide linkers can also be used.

The blocking moiety is attached to the metal ion complex in a variety of ways. In a preferred embodiment, as noted above, the blocking moiety is attached to the metal ion complex via a linker group. Alternatively, the blocking moiety is attached directly to the metal ion complex; for example, as outlined below, the blocking moiety may be a substituent group on the chelator.

In a preferred embodiment at least one of the R groups attached to the "arms" of the chelator, for example $R_9$, $R_{10}$, $R_{11}$ or $R_{12}$ of the DOTA structures, or $R_{13}$, $R_{14}$, $R_{17}$, $R_{20}$ or $R_{21}$ of the DTPA structures, comprises an alkyl (including substituted and heteroalkyl groups), or aryl (including substituted and heteroaryl groups), i.e. is a group sterically bulkier than hydrogen. This is particular useful to drive the equilibrium towards "locking" the coordination atom of the arm into place to prevent water exchange, as is known for standard MRI contrast agents. Preferred groups include the C1 through C6 alkyl groups with methyl being particularly preferred.

This is particularly preferred when the blocking moiety is attached via one of the "arms", for example when a blocking moiety is at position $X_1$ to $X_4$ (Structure 6), position S, T, U or V (Structure 8) or position H, I, J or K of Structure 16.

However the inclusion of too many groups may drive the equilibrium in the other direction effectively locking the coordination atom out of position, as is shown in Example 3. Therefore in a preferred embodiment only 1 or 2 of these positions is a non-hydrogen group, unless other methods are used to drive the equilibrium towards binding.

The blocking moieties are chosen and designed using a variety of parameters. In the embodiment which uses a coordination site barrier, i.e. when the functional group of the blocking moiety does not provide a coordination atom, and the coordination site barrier is fastened or secured on two sides, the affinity of the coordination site barrier of the blocking moiety for the metal ion complex need not be great, since it is tethered in place. That is, in this embodiment, the complex is "off" in the absence of the target substance. However, in the embodiment where the blocking moiety is linked to the complex in such a manner as to allow some rotation or flexibility of the blocking moiety, for example, it is linked on one side only, such as the galactose embodiment of the examples, the blocking moiety should be designed such that it occupies the coordination site a majority of the time. Thus, for example, the galactose-DOTA structure of Example 1 gives roughly a 20% increase in the signal in the presence of galactosidase, thus indicating that the galactose blocking moiety is in equilibrium between blocking or occupying the coordination site and rotating free in solution. However, as described herein and shown in Example 3, these agents may be "locked" off using R groups on the carboxylic acid "arms" of a chelator, to reduce the rotational freedom of the group and thus effectively drive the equilibrium to the "off" position, and thus result in a larger percentage increase in the signal in the presence of the target.

When the blocking moiety is not covalently tethered on two sides, as is depicted in FIG. 1, it should be understood that blocking moieties and coordination site barriers are chosen to maximize three basic interactions that allow the blocking moiety to be sufficiently associated with the complex to hinder the rapid exchange of water in at least one coordination site of the complex. First, there may be electrostatic interactions between the blocking moiety and the metal ion, to allow the blocking moiety to associate with the complex. Secondly, there may be Van der Waals and dipole—dipole interactions. Thirdly, there may be ligand interactions, that is, one or more functionalities of the blocking moiety may serve as coordination atoms for the metal. In addition, linker groups may be chosen to force or favor certain conformations, to drive the equilibrium towards an associated blocking moiety. Similarly, removing degrees of fredom in the molecule may force a particular conformation to prevail. Thus, for example, the addition of alkyl groups, and particularly methyl groups, at positions equivalent to the $R_9$ to $R_{12}$ positions of Structure 7 when the blocking moiety is attached at W, X, Y or Z, can lead the blocking moiety to favor the blocking position. Similar restrictions can be made in the other embodiments, as will be appreciated by those in the art.

Furthermore, effective "tethering" of the blocking moiety down over the metal ion may also be done by engineering in other non-covalent interactions that will serve to increase the affinity of the blocking moiety to the chelator complex, as is depicted below.

Potential blocking moieties may be easily tested to see if they are functional; that is, if they sufficiently occupy or block the appropriate coordination site or sites of the complex to prevent rapid exchange of water. Thus, for example, complexes are made with potential blocking moieties and then compared with the chelator without the blocking moiety in imaging experiments. Once it is shown that the blocking moiety is a sufficient "blocker", the target substance is added and the experiments repeated, to show that interaction with the target substance increases the exchange of water and thus enhances the image.

Thus, as outlined above, the metal ion complexes of the present invention comprise a paramagnetic metal ion bound to a chelator and at least one blocking moiety. In a preferrred embodiment, the metal ion complexes have the formula shown in Structure 6:

Structure 6

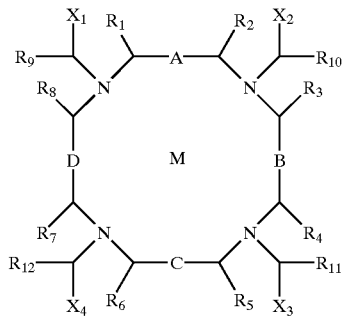

In Structure 6, M is a paramagnetic metal ion selected from the group consisting of Gd(III), Fe(III), Mn(II), Yt(III), and Dy(III). A, B, C and D are each either single or double bonds. The $R_1$ through $R_{12}$ groups are alkyl or aryl groups, as defined above, including substituted alkyl and aryl groups, phosphorus groups, or a blocking moiety, as described above. $X_1$ through $X_4$ are —OH, —COO—, —(CH2)$_n$OH (with —CH$_2$OH being preferred), —(CH2)$_n$COO— (with CH$_2$COO— being preferred) or a blocking moiety. n is from 1 to 10, with from 1 to 5 being preferred. At least one of $R_1$ to $R_{12}$ and $X_1$ to $X_4$ is a blocking moiety.

Structure 6 includes Structures 7 and 8, shown below:

Structure 7

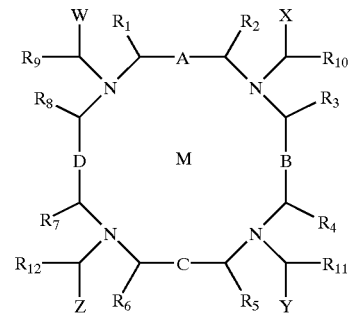

In this embodiment, W, X, Y and Z are as defined above for X, and at least one of the $R_1$ to $R_{12}$ groups is a blocking moiety.

As applied to DOTA, the four nitrogens of the DOTA ring, and the W, X, Y and Z groups provide 8 of the coordination atoms for the paramagnetic metal ion. The ninth coordination atom is provided by a blocking moiety which is substituted at one of the $R_1$ to $R_{12}$ positions. In a preferred embodiment, the other R groups are either hydrogen or methyl; in a particularly preferred embodiment the chelator is Gd-MCTA, which has a single methyl group on the DOTA ring (see Meyer et al., Invest. Radiol. 25:S53 (1990)).

In an alternative embodiment, the metal ion complexes have the formula depicted in Structure 8:

Structure 8

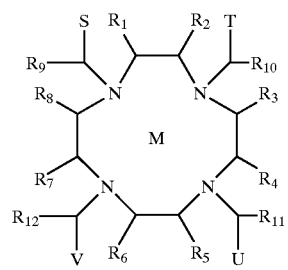

In this embodiment, S, T, U, and V are —OH, —COO—, —(CH2)$_n$OH (with —CH$_2$OH being preferred), —(CH2)$_n$COO— (with CH$_2$COO— being preferred) or a blocking moiety. In this embodiment, the four nitrogens of the DOTA ring, and three of the S, T, U or V groups provide 7 of the coordination atoms for the paramagnetic metal ion. The remaining coordination atoms are provided by a blocking moiety which is substituted at one of the S, T, U or V positions. Alternatively, the coordination sites are either filled by coordination atoms provided by the S, T, U or V groups, or blocked by the S, T, U or V structure, or both. In addition, Structure 8 does not depict the A, B, C and D bonds, but as for the other embodiments, these bonds may be either single or double bonds.

As applied to DOTA, the four nitrogens of the DOTA ring, and the (generally) three S, T and U groups provide 7 of the coordination atoms for the Gd(III) paramagnetic metal ion. The eigth and ninth coordination atoms are provided by a blocking moiety which is substituted at one of the S, T, U and V positions. As above, the other R groups are preferably either hydrogen or methyl, with Gd-MCTA being especially preferred.

In the Structures depicted herein, any or all of A, B, C or D may be a single bond or a double bond. It is to be understood that when one or more of these bonds are double bonds, there may be only a single substitutent group attached to the carbons of the double bond. For example, when A is a double bond, there may be only a single $R_1$ and a single $R_2$ group attached to the respective carbons; in a preferred embodiment, as described below, the $R_1$ and $R_2$ groups are hydrogen. In a preferred embodiment, A is a single bond, and it is possible to have two $R_1$ groups and two $R_2$ groups on the respective carbons. In a preferred embodiment, these groups are all hydrogen with the exception of a single blocking moiety, but alternate embodiments utilize two R groups which may be the same or different. That is, there may be a hydrogen and a blocking group attached in the $R_1$ position, and two hydrogens, two alkyl groups, or a hydrogen and an alkyl group in the $R_2$ positions.

It is to be understood that the exact composition of the $X_1$–$X_4$ (Structure 6) S, T, U, V (Structure 8) or W, X, Y and Z (Structure 7) groups will depend on the presence of the metal ion. That is, in the absence of the metal ion, the groups may be —OH, —COOH, —(CH$_2$)$_n$OH, or (CH$_2$)$_n$COOH; however, when the metal is present, the groups may be —OH, —COO—, —(CH$_2$)$_n$O—, or (CH$_2$)$_n$COO—.

In a preferred embodiment, the compositions have the formula shown in Structure 9:

Structure 9

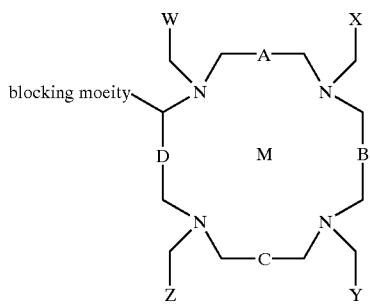

In this embodiment, there is a single blocking moiety attached to the metal ion complex. That is, all but one of the R groups are hydrogen. It should be appreciated that the blocking moiety may be at any of the R positions.

In a preferred embodiment, the magnetic resonance imaging agents are used to detect Ca+2 ions, and have the structure depicted in Structure 10:

Structure 10:

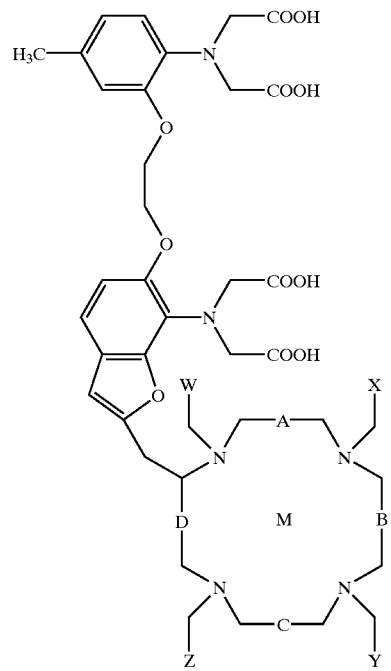

In this embodiment, the blocking moiety comprises a linker and the BAPTA molecule, although any of the fura-type Ca$^{+2}$ ligands may be substituted. Without being bound by theory, it appears that one of the carboxy groups of the BAPTA moiety serves to provide a coordination atom in the absence of Ca+2. However, in the presence of Ca+2, the carboxy group chelates Ca+2, and thus is unavailable as a coordination group, thus allowing the rapid exchange of water. Preferably, the metal ion is Gd(III), the R groups are all hydrogen, and the W, X, Y and Z groups are carboxy.

In one embodiment the carboxylic acid groups of the BAPTA molecule may be protected with acetate protecting groups, resulting a neutral molecule that may then cross membranes. Once inside a cell, intracellular esterases can cleave off the acetate protecting groups, allowing the detection of Ca$^{+2}$. See Li et al., Tetrahedron 53(35):12017–12040 (1997).

In a preferred embodiment, the compositions have the formula shown in Structure 11:

Structure 11

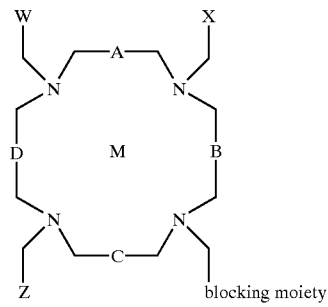

In this embodiment, there is a single blocking moiety attached to the metal ion complex. It should be appreciated that the blocking moiety may be at any of the S, T, U or V positions. Similarly, a single blocking moiety may be attached to DTPA.

In a preferred embodiment, the magnetic resonance imaging contrast agents have the structure shown in Structure 12:

Structure 12

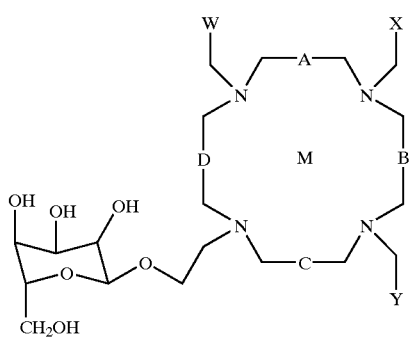

In this embodiment, the blocking moiety comprises a linker and a carbohydrate, attached to the complex via a β(1, 4) linkage such as is recognized by lactose or β-galactosidase. Without being bound by theory, it is apparent that the galactose moiety provides a coordination atom, such that in the absence of β-galactosidase there is reduced exchange of water in the complex. Upon exposure to β-galactosidase, the carbohydrate blocking moiety is cleaved off, removing the coordination atom and allowing the rapid exchange of water. Preferably, the R groups are hydrogen, and the W, X, Y and Z groups are carboxy.

In another embodiment, the metal ion complexes have the formula depicted in Structure 13:

Structure 13:

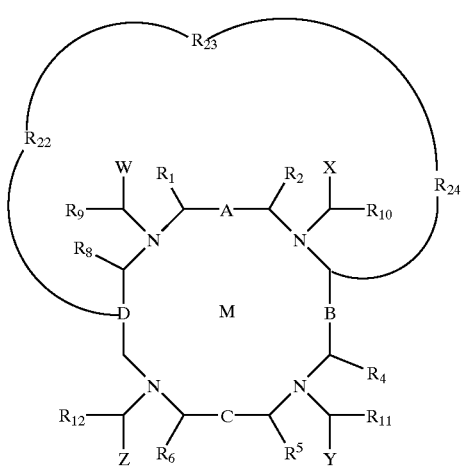

In this embodiment, $R_{22}$, $R_{23}$ and $R_{24}$ comprise a blocking moiety, with $R_{23}$ being a coordination site barrier which also serves to contribute a coordination atom. It is to be understood that the $R_{22}$ and $R_{24}$ groups may be attached at any of the $R_1$ to $R_{12}$ positions. Preferred $R_{23}$ groups include, but are not limited to, compounds listed above that provide a coordination atom, blocking moieties, and those shown in FIG. 2. $R_{22}$ and $R_{24}$ may also comprise a linker, as defined above and as shown in Structure 14, below. Preferred $R_{22}$ and $R_{24}$ groups include enzyme substrates which are cleaved upon exposure to the enzyme, such as carbohydrates and peptides. Accordingly, when the target substance is a carbohydrase such as β-galactosidase, the compositions have the formula shown in Structure 14:

Structure 14

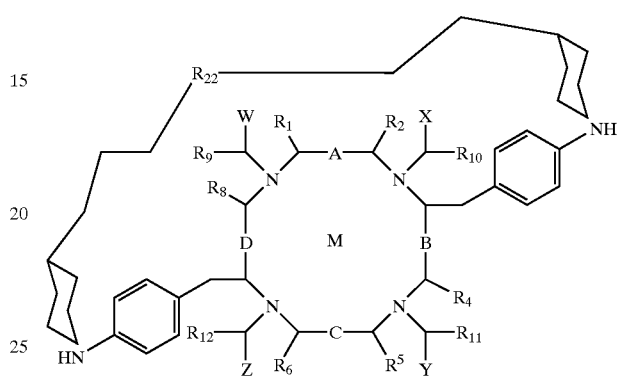

In this embodiment, the blocking moiety comprises two linkers, two carbohydrates, and a coordination site barrier. The carbohydrates are attached to the complex via a linkage which will be recognized by a carbohydrase such as a β(1, 4) linkage such as is recognized by lactose or β-galactosidase. The $R_{22}$ group provides a coordination atom in the absence of the carbohydrase such there is no rapid exchange of water in the complex. Upon exposure to the carbohydrase, such as β-galactosidase, one or both of the carbohydrate blocking moieties are cleaved off, removing the coordination atom and allowing the rapid exchange of water. Preferably, the R groups are hydrogen, and the W, X, Y and Z groups are carboxy. Alternatively, the blocking moiety could comprise peptides for a protease target substance.

In place of the carbohydrates in Structure 14, an alternative embodiment utilizes peptides. That is, a peptide comprising 2 to 5 amino acids or analogs may be "stretched" from one side of the complex to the other, and linker groups may or may not be used. Similarly, nucleic acids may be used.

Alternatively, there may not be covalent attachment at both ends. As discussed above, effective "tethering" of the blocking moiety down over the metal ion may also be done by engineering in other non-covalent interactions that will serve to increase the affinity of the blocking moiety to the chelator complex. Thus, for example, electrostatic interactions may be used, as is generally depicted below for a DOTA derivative in Structure 15:

Structure 15

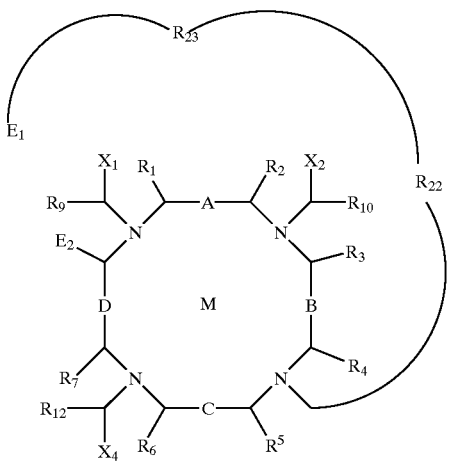

In Structure 15, the blocking moeity/coordination site barrier occupies the $X_3$ position, although any position may be utilized. $E_1$ and $E_2$ and electrostatic moieties bearing opposite charges. In Structure 15, the $E_2$ group is shown a position $R_8$, although any position may be used.

A further embodiment utilizes metal ion complexes having the formula shown in Structure 16:

Structure 16

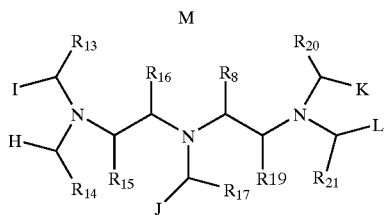

It is to be understood that, as above, the exact composition of the H, I, J, K and L groups will depend on the presence of the metal ion. That is, in the absence of the metal ion, H, I, J, K and L are —OH, —COOH, —$(CH_2)_n$OH, or $(CH_2)_n$COOH; however, when the metal is present, the groups are —OH, —COO—, —$(CH_2)_n$OH, or $(CH_2)_n$COO—.

In this embodiment, $R_{13}$ through $R_{21}$ are alkyl or aryl, including substituted and hetero derivatives, a phosphorus moiety or a blocking moiety, all as defined above. In a preferred embodiment, $R_{12}$ to $R_{21}$ are hydrogen. At least one of $R_{13}$–$R_{21}$, H, I, J, K or L is a blocking moiety, as defined above.

In a preferred embodiment, the MRI contrast agents of the invention comprise more than one metal ion, such that the signal is increased. As is outlined below, this may be done in a number of ways, some of which are shown in FIG. 10.

In a preferred embodiment, the MRI agents of the invention comprise at least two paramagnetic metal ions, each with a chelator and blocking moiety; that is, multimeric MRI agents are made. In a preferred embodiment, the chelators are linked together, either directly or through the use of a linker such as a coupling moiety or polymer. For example, using substitution groups that serve as functional groups for chemical attachment on the chelator, attachment to other chelators may be accomplished. As will be appreciated by those in the art, attachment of more than one MRI agent may also be done via the blocking moieties (or coordination site barriers, etc.), although these are generally not preferred.

In a preferred embodiment, the chelators of the invention include one or more substitution groups that serve as functional groups for chemical attachment. Suitable functional groups include, but are not limited to, amines (preferably primary amines), carboxy groups, and thiols (including SPDP, alkyl and aryl halides, maleimides, α-haloacetyls, and pyridyl disulfides) are useful as functional groups that can allow attachment.

In one embodiment, the chelators are linked together directly, using at least one functional group on each chelator. This may be accomplished using any number of stable bifunctional groups well known in the art, including homobifunctional and heterobifunctional linkers (see Pierce Catalog and Handbook, 1994, pages T155–T200, hereby expressly incorporated by reference). This may result in direct linkage, for example when one chelator comprises a primary amine as a functional group and the second comprises a carboxy group as the functional group, and carbodiimide is used as an agent to activate the carboxy for attach by the nucleophilic amine (see Torchilin et al., *Critical Rev. Therapeutic Drug Carrier Systems*, 7(4):275–308 (1991). Alternatively, as will be appreciated by those in the art, the use of some bifunctional linkers results in a short coupling moiety being present in the structure. A "coupling moiety" is capable of covalently linking two or more entities. In this embodiment, one end or part of the coupling moiety is attached to the first MRI contrast agent, and the other is attached to the second MRI agent. The functional group(s) of the coupling moiety are generally attached to additional atoms, such as alkyl or aryl groups (including hetero alkyl and aryl, and substituted derivatives), to form the coupling moiety. Oxo linkers are also preferred. As will be appreciated by those in the art, a wide range of coupling moieties are possible, and are generally only limited by the ability to synthesize the molecule and the reactivity of the functional group. Generally, the coupling moiety comprises at least one carbon atom, due to synthetic requirements; however, in some embodiments, the coupling moiety may comprise just the functional group.

In a preferred embodiment, the coupling moiety comprises additional atoms as a spacer. As will be appreciated by those in the art, a wide variety of groups may be used. For example, a coupling moiety may comprise an alkyl or aryl group substituted with one or more functional groups. Thus, in one embodiment, a coupling moiety containing a multiplicity of functional groups for attachment of multiple MRI contrast agents may be used, similar to the polymer embodiment described below. For example, branched alkyl groups containing multiple functional groups may be desirable in some embodiments.

In an additional embodiment, the linker is a polymer. In this embodiment, a polymer comprising at least one MRI contrast agent of the invention is used. As will be appreciated by those in the art, these MRI contrast agents may be monomeric (i.e. one metal ion, one chelator, one blocking moiety) or a duplex, as is generally described below (i.e. two metal ions, two chelators, one blocking moiety). Preferred embodiments utilize a plurality of MRI agents per polymer. The number of MRI agents per polymer will depend on the density of MRI agents per unit length and the length of the polymer.

The character of the polymer will vary, but what is important is that the polymer either contain or can be modified to contain functional groups for the the attachment of the MRI contrast agents of the invention. Suitable polymers include, but are not limited to, functionalized dextrans, styrene polymers, polyethylene and derivatives, polyanions including, but not limited to, polymers of heparin, polygalacturonic acid, mucin, nucleic acids and their analogs including those with modified ribose-phosphate backbones, the polypeptides polyglutamate and polyaspartate, as well as carboxylic acid, phosphoric acid, and sulfonic acid derivatives of synthetic polymers; and polycations, including but not limited to, synthetic polycations based on acrylamide and 2-acrylamido-2-methylpropanetrimethylamine, poly(N-ethyl-4-vinylpyridine) or similar quaternized polypyridine, diethylaminoethyl polymers and dextran conjugates, polymyxin B sulfate, lipopolyamines, poly(allylamines) such as the strong polycation poly(dimethyidiallylammonium chloride), polyethyleneimine, polybrene, spermine, spermidine and polypeptides such as protamine, the histone polypeptides, polylysine, polyarginine and polyornithine; and mixtures and derivatives of these. Particularly preferred polycations are polylysine and spermidine, with the former being especially preferred. Both optical isomers of polylysine can be used. The D isomer has the advantage of having long-term resistance to cellular proteases. The L isomer has the advantage of being more rapidly cleared from the subject. As will be appreciated by those in the art, linear and branched polymers may be used.

A preferred polymer is polylysine, as the —NH$_2$ groups of the lysine side chains at high pH serve as strong nucleophiles for multiple attachment of activated chelating agents. At high pH the lysine monomers are coupled to the MRI agents under conditions that yield on average 5–20% monomer substitution.

In some embodiments, particularly when charged polymers are used, there may be a second polymer of opposite charge to the first that is electrostatically associated with the first polymer, to reduce the overall charge of polymer-MRI agent complex. This second polymer may or may not contain MRI agents.

The size of the polymer may vary substantially. For example, it is known that some nucleic acid vectors can deliver genes up to 100 kilobases in length, and artificial chromosomes (megabases) have been delivered to yeast. Therefore, there is no general size limit to the polymer. However, a preferred size for the polymer is from about 10 to about 50,000 monomer units, with from about 2000 to about 5000 being particularly preferred, and from about 3 to about 25 being especially preferred.

It should be understood that the multimeric MRI agents of the invention may be made in a variety of ways, including those listed above. What is important is that manner of attachment does not significantly alter the functionality of the agents; that is, the agents must still be "off" in the absence of the target substance and "on" in its presence.

In a preferred embodiment, the MRI contrast agents of the invention are "duplexes". In this embodiment, the MRI duplex comprises two chelators, each with a paramagnetic metal ion, and at least one blocking moiety that restricts the exchange of water in at least one coordination site of each chelator. In this way, a sort of signal amplification occurs, with two metal ions increasing the signal with a single target molecule. While "duplex" implies two chelators, it is intended to refer to complexes comprising a single blocking moiety donating coordination atoms to more than 1 metal ion/chelator complex. As will be appreciated by those in the art, the MRI agents of this embodiment may have a number of different conformations, as is generally shown in FIG. 10. As will be appreciated by those in the art, the R$_{26}$, R$_{27}$ and R$_{28}$ groups of the figure can be attached to any of the positions described herein, to any R groups or X$_1$–X$_4$, S, T, U, V, W, X, Y, or Z groups.

As outlined above, the MRI duplex moieties may also be combined into higher multimers, either by direct linkage or via attachment to a polymer.

In a preferred embodiment, the blocking moiety is BAPTA, as is generally depicted below in Structure 17, with propyl linking groups between the chelators and the BAPTA derivative:

Structure 17

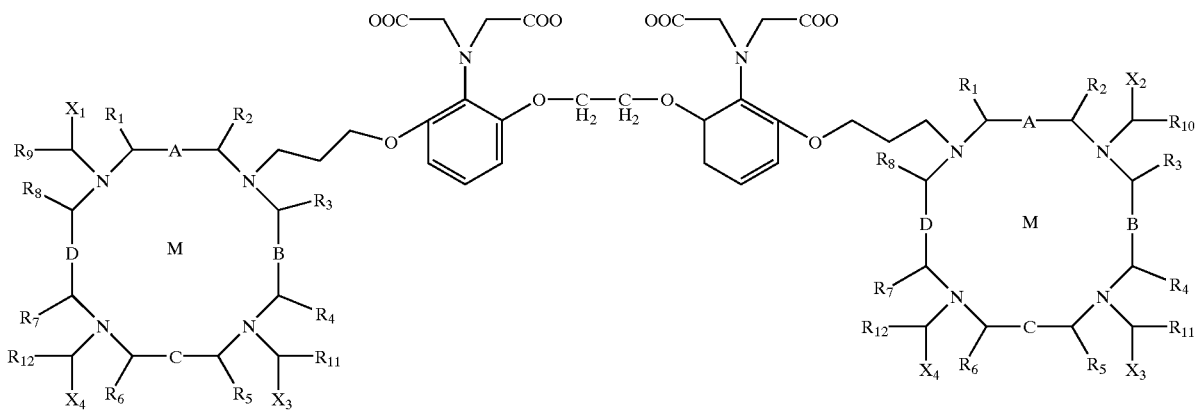

As will be appreciated by those in the art, the structure depicted in Structure 17 may be altered, for example, replacing the phenyl groups of the BAPTA derivative with cycloalkyl groups, or removing them entirely, as is generally depicted in Structure 19:

Structure 19

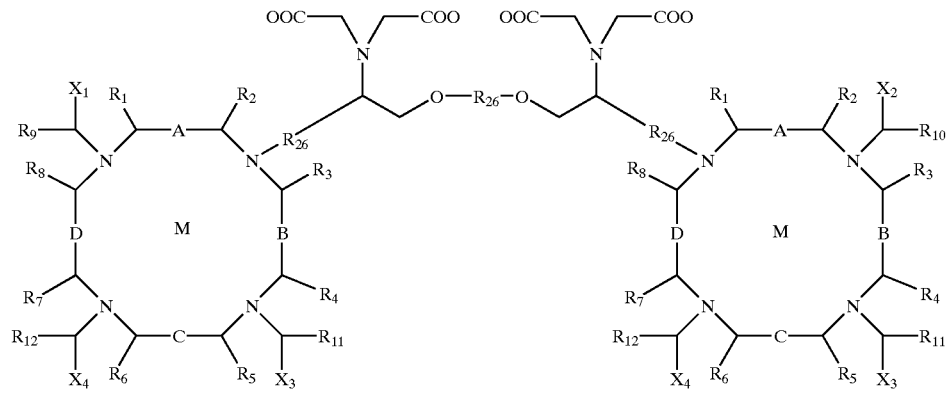

As noted above, the carboxylic acids of the BAPTA molecule may also be protected using acetate protecting groups, to render a neutral molecule for entry into cells, that then can be reactivated via cleavage by intracellular esterases.

In addition, although Structures 17 and 19 have ethylene groups between the oxygens of the bridge of BAPTA, methylene and propylene may also be used, as well as substituted derivatives of these.

In a preferred embodiment, A, B, C and D are single bonds, $R_1$–$R_{12}$ are hydrogen, and each $R_{26}$ is —$CH_2O$—, with the $CH_2$ group being attached to the macrocycle.

In addition, the complexes and metal ion complexes of the invention may further comprise one or more targeting moieties. That is, a targeting moiety may be attached at any of the R positions (or to a linker, including a polymer, or to a blocking moiety, etc.), although in a preferred embodiment the targeting moiety does not replace a coordination atom. By "targeting moiety" herein is meant a functional group which serves to target or direct the complex to a particular location, cell type, diseased tissue, or association. In general, the targeting moiety is directed against a target molecule. As will be appreciated by those in the art, the MRI contrast agents of the invention are generally injected intravenously; thus preferred targeting moieties are those that allow concentration of the agents in a particular localization. Thus, for example, antibodies, cell surface receptor ligands and hormones, lipids, sugars and dextrans, alcohols, bile acids, fatty acids, amino acids, peptides and nucleic acids may all be attached to localize or target the contrast agent to a particular site.

In a preferred embodiment, the targeting moiety allows targeting of the MRI agents of the invention to a particular tissue or the surface of a cell. That is, in a preferred embodiment the MRI agents of the invention need not be taken up into the cytoplasm of a cell to be activated.

As will be appreciated by those in the art, the targeting moieties can be attached in a large number of different ways, and in a variety of configurations, as are schematically depicted in FIG. 23.

In a preferred embodiment, the targeting moiety is a peptide. For example, chemotactic peptides have been used to image tissue injury and inflammation, particularly by bacterial infection; see WO 97/14443, hereby expressly incorporated by reference in its entirety.

In a preferred embodiment, the targeting moiety is an antibody. The term "antibody" includes antibody fragments, as are known in the art, including Fab $Fab_2$, single chain antibodies (Fv for example), chimeric antibodies, etc., either produced by the modification of whole antibodies or those synthesized de novo using recombinant DNA technologies.

In a preferred embodiment, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature 321:522–525 (1986); Riechmann et al., Nature 332:323–329 (1988); and Presta, Curr. Op. Struct. Biol. 2:593–596 (1992)].

Methods for humanizing non-human antibodies are well known in the art. Generally, a humanized antibody has one or more amino acid residues introduced into it from a source which is non-human.

These non-human amino acid residues are often referred to as "import" residues, which are typically taken from an "import" variable domain. Humanization can be essentially performed following the method of Winter and co-workers [Jones et al., Nature 321:522–525 (1986); Riechmann et al., Nature 332:323–327 (1988); Verhoeyen et al., Science 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol. 227:381 (1991); Marks et al., J. Mol. Biol. 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol. 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10:779–783 (1992); Lonberg et al., Nature 368:856–859 (1994); Morrison, Nature 368:812–13 (1994); Fishwild et al., Nature Biotechnology 14:845–51 (1996); Neuberger, Nature Biotechnology, 14:826 (1996); Lonberg and Huszar, Intern. Rev. Immunol. 13:65–93 (1995).

Bispecific antibodies are monoclonal, preferably human or humanized, antibodies that have binding specificities for at least two different antigens. In the present case, one of the binding specificities is for a first target molecule and the other one is for a second target molecule.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J. 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

In a preferred embodiment, the antibody is directed against a cell-surface marker on a cancer cell; that is, the target molecule is a cell surface molecule. As is known in the art, there are a wide variety of antibodies known to be differentially expressed on tumor cells, including, but not limited to, HER2, VEGF, etc.

In addition, antibodies against physiologically relevant carbohydrates may be used, including, but not limited to, antibodies against markers for breast cancer (CA15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

In a preferred embodiment, the targeting moiety is all or a portion (e.g. a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters (particularly GLUT 4 receptor), transferrin receptor (transferrin), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-α and TGF-β), EPO receptor (EPO), TPO receptor (TPO), ciliary neurotrophic factor receptor, prolactin receptor, and T-cell receptors. In particular, hormone ligands are preferred. Hormones include both steroid hormones and proteinaceous hormones, including, but not limited to, epinephrine, thyroxine, oxytocin, insulin, thyroid-stimulating hormone, calcitonin, chorionic gonadotropin, cortictropin, follicle-stimulating hormone, glucagon, leuteinizing hormone, lipotropin, melanocyte-stimutating hormone, norepinephrine, parathryroid hormone, thyroid-stimulating hormone (TSH), vasopressin, enkephalins, seratonin, estradiol, progesterone, testosterone, cortisone, and glucocorticoids and the hormones listed above. Receptor ligands include ligands that bind to receptors such as cell surface receptors, which include hormones, lipids, proteins, glycoproteins, signal transducers, growth factors, cytokines, and others.

In a preferred embodiment, the targeting moiety is a carbohydrate. By "carbohydrate" herein is meant a compound with the general formula $Cx(H2O)y$. Monosaccharides, disaccharides, and oligo- or polysaccharides are all included within the definition and comprise polymers of various sugar molecules linked via glycosidic linkages. Particularly preferred carbohydrates are those that comprise all or part of the carbohydrate component of glycosylated proteins, including monomers and oligomers of galactose, mannose, fucose, galactosamine, (particularly N-acetylglucosamine), glucosamine, glucose and sialic acid, and in particular the glycosylation component that allows binding to certain receptors such as cell surface receptors. Other carbohydrates comprise monomers and polymers of glucose, ribose, lactose, raffinose, fructose, and other biologically significant carbohydrates. In particular, polysaccharides (including, but not limited to, arabinogalactan, gum arabic, mannan, etc.) have been used to deliver MRI agents into cells; see U.S. Pat. No. 5,554,386, hereby incorporated by reference in its entirety.

In a preferred embodiment, the targeting moiety is a lipid. "Lipid" as used herein includes fats, fatty oils, waxes, phospholipids, glycolipids, terpenes, fatty acids, and glycerides, particularly the triglycerides. Also included within the definition of lipids are the eicosanoids, steroids and sterols, some of which are also hormones, such as prostaglandins, opiates, and cholesterol.

In addition, as will be appreciated by those in the art, any moiety which may be utilized as a blocking moiety can be used as a targeting moiety. Particularly preferred in this regard are enzyme inhibitors, as they will not be cleaved off and will serve to localize the MRI agent in the location of the enzyme.

In a preferred embodiment, the targeting moiety may be used to either allow the internalization of the MRI agent to the cell cytoplasm or localize it to a particular cellular compartment, such as the nucleus.

In a preferred embodiment, the targeting moiety is all or a portion of the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldwin et al., EMBO J. 9:1511 (1990), all of which are incorporated by reference.

In a preferred embodiment, the targeting moiety is a nuclear localization signal (NLS). NLSs are generally short, positively charged (basic) domains that serve to direct the moiety to which they are attached to the cell's nucleus. Numerous NLS amino acid sequences have been reported including single basic NLS's such as that of the SV4O (monkey virus) large T Antigen (Pro Lys Lys Lys Arg Lys Val, SEQ ID NO: 13), Kalderon (1984), et al., Cell, 39:499–509; the human retinoic acid receptor-β nuclear localization signal (ARRRRP, SEQ ID NO: 14); NFκB p50 (EEVQRKRQKL, SEQ ID NO: 15; Ghosh et al., Cell 62:1019 (1990); NFκB p65 (EEKRKRTYE, SEQ ID NO: 16; Nolan et al., Cell 64:961 (1991); and others (see for example Boulikas, J. Cell. Biochem. 55(1):32–58 (1994), hereby incorporated by reference) and double basic NLS's exemplified by that of the Xenopus (African clawed toad) protein, nucleoplasmin (Ala Val Lys Arg Pro Ala Ala Thr Lys Lys Ala Gly Gin Ala Lys Lys Lys Lys Leu Asp, SEQ ID NO: 17), Dingwall, et al., Cell, 30:449–458, 1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990.

In a preferred embodiment, targeting moieties for the hepatobiliary system are used; see U.S. Pat. Nos. 5,573,752 and 5,582,814, both of which are hereby incorporated by reference in their entirety.

In a preferred embodiment, the metal ion complexes of the present invention are water soluble or soluble in aqueous solution. By "soluble in aqueous solution" herein is meant that the MRI agent has appreciable solubility in aqueous solution and other physiological buffers and solutions. Solubility may be measured in a variety of ways. In one embodiment, solubility is measured using the United States Pharmacopeia solubility classifications, with the metal ion complex being either very soluble (requiring less than one part of solvent for 1 part of solute), freely soluble (requiring one to ten parts solvent per 1 part solute), soluble (requiring ten to thirty parts solvent per 1 part solute), sparingly soluble (requiring 30 to 100 parts solvent per 1 part solute), or slightly soluble (requiring 100–1000 parts solvent per 1 part solute).

Testing whether a particular metal ion complex is soluble in aqueous solution is routine, as will be appreciated by those in the art. For example, the parts of solvent required to solubilize a single part of MRI agent may be measured, or solubility in gm/ml may be determined.

The complexes of the invention are generally synthesized using well known techniques. See, for example, Moi et al., supra; Tsien et al., supra; Borch et al., J. Am. Chem. Soc., p2987 (1971); Alexander, (1995), supra; Jackels (1990), supra, U.S. Pat. Nos. 5,155,215, 5,087,440, 5,219,553, 5,188,816, 4,885,363, 5,358,704, 5,262,532; Meyer et al., (1990), supra, Moi et al., (1988), and McMurray et al., Bioconjugate Chem. 3(2):108–117 (1992)).

For DOTA derivatives, the synthesis depends on whether nitrogen substitution or carbon substitution of the cyclen ring backbone is desired. For nitrogen substitution, such as is exemplified by the galactose-DOTA structures of the examples, the synthesis begins with cyclen or cyclen derivatives, as is well known in the art; see for example U.S. Pat. Nos. 4,885,363 and 5,358,704. FIGS. 3 and 4 depict the nitrogen substitution as exemplified by galactose-DOTA derivatives.

For carbon substitution, such as is exemplified by the BAPTA-DOTA structures of the examples, well known techniques are used. See for example Moi et al., supra, and Gansow, supra. FIGS. 5 and 6 depict the carbon substitution as exemplified by the BAPTA-DOTA type derivatives.

The contrast agents of the invention are complexed with the appropriate metal ion as is known in the art. While the structures depicted herein all comprise a metal ion, it is to be understood that the contrast agents of the invention need not have a metal ion present initially. Metal ions can be added to water in the form of an oxide or in the form of a halide and treated with an equimolar amount of a contrast agent composition. The contrast agent may be added as an aqueous solution or suspension. Dilute acid or base can be added if need to maintain a neutral pH. Heating at temperatures as high as 100° C. may be required.

The complexes of the invention can be isolated and purified, for example using HPLC systems.

Pharmaceutical compositions comprising pharmaceutically acceptable salts of the contrast agents can also be prepared by using a base to neutralize the complexes while they are still in solution. Some of the complexes are formally uncharged and do not need counterions.

Once synthesized, the metal ion complexes of the invention have use as magnetic resonance imaging contrast or enhancement agents. Specifically, the functional MRI agents of the invention have several important uses. First, they may be used to diagnose disease states of the brain, as is outlined below. Second, they may be used in real-time detection and differentiation of myocardial infraction versus ischemia. Third, they may be used in in vivo, i.e. whole organism, investigation of antigens and immunocytochemistry for the location of tumors. Fourth, they may be used in the identification and localization of toxin and drug binding sites. In addition, they may be used to perform rapid screens of the physiological response to drug therapy.

The metal ion complexes of the invention may be used in a similar manner to the known gadolinium MRI agents. See for example, Meyer et al., supra; U.S. Pat. No. 5,155,215; U.S. Pat. No. 5,087,440; Margerstadt et al., Magn. Reson. Med. 3:808 (1986); Runge et al., Radiology 166:835 (1988); and Bousquet et al., Radiology 166:693 (1988). The metal ion complexes are administered to a cell, tissue or patient as is known in the art. A "patient" for the purposes of the present invention includes both humans and other animals and organisms, such as experimental animals. Thus the methods are applicable to both human therapy and veterinary applications. In addition, the metal ion complexes of the invention may be used to image tissues or cells; for example, see Aguayo et al., Nature 322:190 (1986).

Generally, sterile aqueous solutions of the contrast agent complexes of the invention are administered to a patient in a variety of ways, including orally, intrathecally and especially intraveneously in concentrations of 0.003 to 1.0 molar, with dosages from 0.03, 0.05, 0.1, 0.2, and 0.3 millimoles per kilogram of body weight being preferred. Dosages may depend on the structures to be imaged. Suitable dosage levels for similar complexes are outlined in U.S. Pat. Nos. 4,885,363 and 5,358,704.

In addition, the contrast agents of the invention may be delivered via specialized delivery systems, for example, within liposomes (see Navon, Magn. Reson. Med. 3:876–880 (1986)) or microspheres, which may be selectively taken up by different organs (see U.S. Pat. No. 5,155,215).

In some embodiments, it may be desirable to increase the blood clearance times (or half-life) of the MRI agents of the invention. This has been done, for example, by adding carbohydrate polymers to the chelator (see U.S. Pat. No. 5,155,215). Thus, one embodiment utilizes polysaccharides as substitution R groups on the compositions of the invention.

A preferred embodiment utilizes complexes which cross the blood-brain barrier. Thus, as is known in the art, a DOTA derivative which has one of the carboxylic acids replaced by an alcohol to form a neutral DOTA derivative has been shown to cross the blood-brain barrier. Thus, for example, neutral complexes are designed that cross the blood-brain barrier with blocking moieties which detect Ca+2 ions. These compounds are used in MRI of a variety of neurological disorders, including Alzeheimer's disease. Currently it is difficult to correctly diagnosis Alzeheimer's disease, and it would be useful to be able to have a physiological basis to distinguish Alzeheimer's disease from depression, or other treatable clinical symptoms for example.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. The references cited herein are expressly incorporated by reference.

EXAMPLES

Example 1

Synthesis and Characterization of Galactose-DOTA Derivative

Synthesis of Do3a-hydroxyethyl-beta-galactose Gadolinium complex (FIG. 4). Acetyl protected bromo-galactose (Aldrich) was reacted with bromoethanol. Difference ratios of the alpha- and beta-bromoethyl ether of the acetylgalactose were obtained in good yield. The isomers were separated using silica gel chromatography and their assigments were made by hydrolyzing the acetyl protecting groups and comparing the proton NMR coupling constants to known compounds. Recently an x-ray structure was done confirming these assignments (data not shown).

The beta-isomer was reacted with cyclen at reflux in chloroform with monitoring of the reaction by TLC. Hydrolysis of the acetates was acheived with TEA/MCOH/ $H_2O$ overnight, and the solvent was removed under low vacuum. The resulting product was reacted directly with bromoacetic acid and then maintained at pH 10–10.5 until the pH remained constant. The possible products all would have different charges in ammonia acetate buffer and thus were separated by anion exchange chromatography. An ammonium acetate buffer gradient was used during FPLC anion exchange to elute the desired compound, with detection at 218 nm. Gadolinium oxide in water at 80° C. was used to insert the metal into the complex. The reaction was followed using fluorescence spectroscopy. The product was purified by HPLC reverse phase chromatography using fluorescence spectroscopy for detection and the structure was confirmed using high resolution mass spectrometry. The overall yield for this essentially one pot synthesis was greater than 25%.

Synthesis of aceto-1-ethylbromo-β-galactose (FIG. 3): 1-Bromoethane-2-ol was reacted with 2,3,4,6-aceto-1-a-bromo-galactose to produce a mixture of α and β anomers (10/90) of aceto-1-ethylbromo-β-galactose in 68% yield (8.3 g). The purified β anomer could be obtained using flash chromatography. Stereochemical assignments were made via a X-ray crystal structure of the β anomer.

Aceto-1-ethylbromo-β-galactose was reacted with cyclen (Aldrich Chemical Co.) to produce the monosubsituted product. The acetate protecting groups were cleaved and the 3 carboxylic acid substituents were added using bromoacetic acid at pH 10.5. The product was isolated by anion exchange fast performance liquid chromatography (FPLC) observed by fluorescence spectrascopy in 37% yield. $Gd^{3+}$ or $Tb^{3+}$ was inserted into the complexes and were purified using repeated collections on a reverse phase HPLC analytic $C_{18}$ column with a water/acetonitrile gradient (0–10%) as the elute and fluorescence for detection (274 nm-ex and 315 nm-em) in 70% yield. High resolution mass spectrum analysis of the solid provided a parent molecular ion for the $(M+Na)^+$ which exhibited the correct exact mass and the predicted isotope ratios.

Alternate synthetic route: Do3a methyl ester was synthesized by literature methods. Do3a methyl ester was reacted with beta-bromoethyl ether of the acetylgalactose obtained as described in $D_2O$/d4 methanol while maintaining the reaction at basic pH. The reaction was followed by NMR. First the acetate methyl ester cleaved and the sugar became water soluble as judged by allowing the methanol to evaporate. Next the methyl ester was absorbed to cleave and finally at around pH 10 a shift consistant with the formation of the sugar Do3a was observed.

Summary of the synthesis of Do2a-hydroxyethyl-di-beta-galactose: The reaction of cyclen with beta-bromoethyl ether of the acetylgalactose in chloroform was done. The reaction mixture was purified using silica gel chromatography. While the alpha isomer gave monosubstitution only di-substituted products were obtained for the beta isomer as shown in FIG. 5. The acetic acid derived arm was added as described for the monosubstituted compound above and purified by FPLC cation exchange using an acid water gradient. Individual fractions were detected by TLC spotting.

Characterization: The ability of β-galactosidase to remove the galactopyranosal blocking group from GadGal was examined by HPLC. The cleavage reaction was monitored using the distinct retention times of the complex and the complex without the galactopyranose residue. Upon incubation with native β-galactosidase, a peak with an elution time of 15 min appeared that corresponds to the complex without galactopyranose. In a control experiment, using heat-inactivated β-galactosidase, the retention time of the peak remained constant. Thus, the HPLC experiments confirm the enzymatic processing of the complex by native but not heat-treated enzyme.

The effect the presence of the galactopyranosal residue on the water exchange rate of the complex was tested by measuring the fluorescence spectra of the terbium ($Tb^{3+}$) derivative (545 nm) in water/deuterium oxide mixtures. Terbium was substituted for Gd because of the more intense fluorescence signal and long lifetime when chelated. The fluorescence of the terbium complex is quenched by $H_2O$ but not by $D_2O$. This effect occurs because the excited state of the terbium is coupled to the OH oscillator but not the OD oscillator. Therefore, the lifetime of the fluorescence signal is longer in $D_2O$ than in $H_2O$. A plot of 1/lifetime versus the percentage of $H_2O$ allows the calculation of the number of water molecules, q, that are fast exchange with the complex (Kumar et al., Pure and Appl. Chem. 65:515–520 (1993); Lie et al., J. Am. Chem. Soc. 117:8123–8138 (1995); Zhang et al., Inorg. Chem. 31:5597–5600 (1992)). The q values for the terbium complexes in the presence and absence of the galactopyranose were 0.7 and 1.2, respectively. Therefore, spectrofluorimetry confirms that the galactopyranose blocking group hinders the fast exchange of water.

The effect of the enzymatic cleavage of the galactopyranose on the $T_1$ of the complex was assessed using NMR spectroscopy. The molar quantity related to these $T_1$ values is the relaxivity, R. R values at 500 MHz were determined for the complex plus galactose (1800 mM $s^{-1}$) and minus galactose (2400 mM $s^{-1}$) and compared to that of the related species Prohance (2700 mM $s^{-1}$). The difference in observed relaxivity parallels the results obtained from the $T_1$ measurements for complexes. The increase in water exchange, demonstrated in the spectrofluorimetry experiments, suggested that the $T_1$ of a solution of the agent should decrease upon enzymatic processing. A 20% difference between the measured $T_1$ values in the presence and absence of β-galactosidase confirmed this prediction. The complex exposed to β-galactosidase at two different concentrations showed identical and significant decreases in the solution $T_1$. A 20% change in observed $T_1$ accompanies cleavage of the galactopyranose from the complex, consistent with the change in measured hydration number, q, obtained from fluorescence measurements. Control solutions of the complex together with heat inactivated enzyme show no decrease; in fact, the $T_1$ appeared to increase slightly. MRI microscopy was used to examine if the observed difference in $T_1$ between the complex in the presence and absence of the galactose would be sufficient to serve as a MRI contrast agent. Images obtained using a standard inversion recovery sequence revealed that the $T_1$ change generated by enzymatic processing could be visualized in a MR image (FIG. 9). The complex was placed in 1.5–1.8 mm capillary tubes, either with or without β-galactosidase. The images displayed in FIG. 9 show that the $T_1$ mediated contrast was altered by the action of β-galactosidase, yielding the expected increase in the image contrast.

Example 2

Synthesis of BAPTA-DTPA and BAPTA-DOTA Derivatives

Two representative synthetic schemes are shown for the synthesis of a BAPTA-DTPA derivative in FIGS. 7 and 8. In FIG. 7 (the preferred method), structure I was prepared by modification of published procedures (Tsien et al., supra) and coupled to hexamehtylenediaamine using $NaCNBrH_3$ in dry methanol. The ratio of reactants used was 6:1:0.6 (diamine:BAPTA aldehyde:$NaCNBrH_3$). The reaction was quenched with the addition of concentrated HCl and the product purified by HPLC (II). This material was reacted with the mono (or bis) anhydride of DTPA with the protecting groups left on the BAPTA until after the Gd(III)$Cl_3$ or $Gd_2O_3$ was added (elevated pH, heat). The final product was purified by ion-exchange HPLC.

In FIG. 8, the monoanhydride of DTPA was prepared and reacted with a bisalkylamine (e.g. $NH_2(CH_2)_6(NH_2)$. This material was purified by ion-exchange HPLC and placed in a round bottom flask equipped with argon inlet and pressure equalizing funnel. The BAPTA aldehyde in dry methanol was added dropwise to a solution of alkylamine-DTPA in dry methanol and 6 equivalents of HCl:MeOH was added. The reaction mixture was purified by HPLC, Gd(III) inserted as above, and the protecting groups removed by literature procedures.

Example 3

The Use of R Groups to Increase Signal

The Example 1 compound exhibits an enhancement of roughly 20% upon exposure to the target analyte, in this case β-galactosidase. In order to increase the MR contrast enhancement, our intention was to further decrease the access of bulk water to the Gd(III) site by stabilizing the position of the galactopyranose unit on top of the macrocyclic framework. Several studies dealing with intramolecular dynamic processes in tetraazacarboxyclic macrocycles were recently reported (see Kang et al., Inorg. Chem. 36:2912 (1993); Aime et al., Inorg. Chem. 36:2095 (1997); Pittet et al., J. Am. Chem. Soc. Dalton Trans. 1997, 895–900; Spirlet et al., J. Am. Chem. Soc. Dalton Trans. 1997, 497–500, all of which are incorporated by reference. This work demonstrated that introducing a-methyl groups to the ethylenic groups of carboxyclic arms increases the rigidity of the amino-carboxylate macrocyclic framework. We therefore added sterically bulky α-methyl groups to two distinct sites of the molecule to make two new compounds. The first, "EGADMe", is the GADGAL of Example 1 with a single methyl group on the DOTA arm containing the galactosyl blocking moiety. The second, "CarboxyMe", is the GAD-GAL of Example 1 with three methyl groups on the other three DOTA arms, leaving the arm containing the galoctosyl blocking moiety alone. The final products EGadMe and CarboxyMe as well as the intermediates were characterized by NMR- and mass spectrometry.

The successful and complete enzymatic cleavage of the galactopyranose blocking group from EGadMe and CarboxyMe, respectively, was followed by TLC chromatography (C18 reverse phase plates in 20 mM tris-acetate, 10 mM EDTA buffer pH 7.0, 8% acetonitrile), to produce EGADMecI and CarboxyMecI. While 90% of the galactopyranose units were enzymatically cleaved from EGadMe within 3 days in an aequous solution containing 0.5 mM EgadMe and 5 µM β-galactosidase at 37° C., the same effect was observed for CarboxyMe within a period of 24 hrs under the same conditions. This result implied that the galactopyranose unit of CarboxyMe might be more exposed and accessible for the enzyme, therefore leading to a higher cleavage rate.

The effect of the enzymatic cleavage of the galactopyranose unit from EGadMe and CarboxyMe on relaxation time T1 was determined by NMR spectroscopy at 500 MHz and 24° C. Various aqueous solutions of 0.5 mM EGadMe and CarboxyMe, respectively, were prepared, containing either: (a) no enzyme; (b) heat inactivated 5 $\mu$M β-galactosidase that was treated at 80° C. for 10 min; (c) 5 $\mu$M β-galactosidase where T1 was measured immediately after mixing; or (d) 5 $\mu$M β-galactosidase that was reacted with the complex for 3.5 days at 37° C. A remarkably difference between the T1 of solutions containing EGadMe and those containing EGadMecI is clearly obvious. In the presence of EGadMecI the T1 of water protons is enhanced by 55% with respect to solutions containing EGadMe. These results indicate that EGadMe is a highly effective, fuctional or "smart" MRI contrast agent. A large difference in T1 between uncleaved and cleaved states represents the crucial factor for successful in vivo applications. Preliminary in vivo studies indicate that the compound fulfils these high expectations.

Interestingly, for solutions (a)–(d) containing CarboxyMe no significant variations in T1 were detected. However, for all CarboxyMe solutions the determined T1 values compare well to those obtained for solutions containing EGadMecI. Since the relaxation time of water protons is in the same order of magnitude for CarboxyMe and CarboxyMecI it must be assumed that the galactopyranose unit does not block the Gd(III) site. It is therefore not effective in limiting the access of bulk water to the metal site.

Molecular modeling studies support this hypothesis. The calculated configurations of EGadMe and CarboxyMe were evaluated. In EGadMe the galactopyranose unit is placed on top of the macrocyclic framework, thereby shielding the metal center. When the galactopyranose unit is cleaved off, the metal site becomes readily exposed and accessible for bulk water molecules to complete the Gd(III) coordination sphere. However, with CarboxyMe the galactopyranose unit is facing away from the macrocyclic unit instead of being located on top of it. The steric influence of the α-methyl groups on the carboxyclic arms seems to prevent the galactopyranose unit from taking a position on top of the Gd(III) site. Therefore the metal site is easily accessible for bulk water molecules in the uncleaved state as much as in the cleaved state, leading to comparable T1 data for both structures. Furthermore, a mass spectrum obtained for CarboxyMe reveals that two chloride anions are coordinated to the molecule that complete the two vacant Gd(III) coordination sites. In EGadMe these coordination sites are filled by the galactopyranose unit.

To determine the efficiency of the galactopyranose unit in blocking the access of water molecules to Gd(III), thereby monitoring the water exchange rate of EGadMe, the lifetime of the fluorescence signal of the corresponding terbium derivative (ETbMe) was investigated. The fluorescence of the terbium complex is quenched by H2O, since terbium is strongly coupled to the OH oscillator. This effect is not observed for the OD-oscillator. As a consequence, the lifetime of the fluorescence signal is longer in $D_2O$ than in $H_2O$. Measuring ETbMe (lex=460 nm, lem=545 nm) in various $H_2O/D_2O$ mixtures and plotting the resulting lifetimes vs. the $D_2O$ concentration leads to the number of water molecules q, that are in fast exchange with the complex (see Kumar et al., Pure Appl. Chem 65:515–520 (1993); Li et al, J. Am. Chem. Soc. 117:8132 (1995); Horrocks et al., J. Am. Chem. Soc. 101:334 (1979); Zhang et al., Iorg. Chem. 31:5597 (1992), all of which are incorporated by reference. For ETbMe a value of q=0.6 was determined, which was compared to a value of q=1.2 observed for the tetraaceticacid macrocycle Gd-DOTA (see Lauffer, Chem. Rev. 901–927 (1997). The change in the number of coordinating water molecules is clearly obvious. For the corresponding cleaved complex, ETbMecI, the exponential decay of the fluorescence signal was much faster, indicating a number of q<1. However, attempts to detemine q for ETbMecI correctly were limited by the time-resolution of the fluorimeter.

Assuming a number of 1<q<2 for EGadMecI is in total agreement with the T1 data observed for EGadMe and EGadMecI and structural arrangements, where the hydroxy group in EGadMecI is not tightly coordinating the metal site. Theory predicts that an increase in q is related to an increase in T1. It can therefore be assumed that the large difference in T1 of 55% is a synergetic effect, i.e. effective blocking the access of bulk water to the metal site by the galactopyranose unit in EGadMe and assuming a number of water molecules that are in fast exchange with the complex 1<q<2 in EGadMecI.

Example 4

Synthesis of $Gd^{3+}$-BAPTA-DO3A$_2$ ("CalGad")

The synthetic scheme for Calgad is shown in FIG. 14.

Compound 1: 2-Nitroresorcinol (2 g, 12.9 mmol) was dissolved in 95% ethanol (15 mL), 1 equivalent of NaOH was added slowly. After the addition the solvent was removed under vacuum and the resulting solid was redissolved in 4 mL DMF with 1 equivalent of 3-bromopropanol. After heating the solution at 100° C. for 7 hours, the reaction was quenched with a few drops of acetic acid. After removing the solvent under vacuum, the residue was suspended in methylene chloride and filtered. Flash chromotography ($CH_2Cl_2$/MeOH, 20:1) afforded 1.08 g (42%) of 1. $^1$H-NMR (300 MHz, CDCl$_3$): 2.14(m, 2H, $CH_2CH_2CH_2$), 3.94(t, 2H, $CH_2OH$), 4.26(t, $OCH_2$), 6.6(d, 1H, aromatic H), 6.72(d, 1H, aromatic H), 7.41(t, 1H, aromatic H).

Compound 2: Compound 1 (0.8 g, 3.76 mmol) was dissolved in 8 mL DMF. 1,2Dibromoethane (0.16 mL, 1.88 mmol) and K$_2$CO3 (0.28 g) was then added and the mixture was heated at 120° C. for 10 h. The reaction was quenched with a few drops of acetic acid and the solvent was evaporated under vacuum. The residue was purified by flash chromatography ($CH_2Cl_2$/MeOH, 20:1) and 0.46 g of product (55%) was obtained. $^1$H-NMR (CDCl$_3$): 2.0(m, 4H, $CH_2CH_2CH_2$), 3.85(m, 4H, $CH_2OH$), 4.25(t, 4H, $CH_2O$), 4.46(s, 4H, $OCH_2CH_2O$), 6.66(m, 4H, aromatic H), 7.4(t, 2H, aromatic H).

Compound 3: Compound 2 (0.15 g) was suspended in a mixture of ethyl acetate (10 mL) and 95% ethanol (10 mL). After adding Palladium catalyst (Pa/carbon, 10%, 50 mg), the solution was hydrogenated at 1 atm overnight. The catalyst was filtered off and the filtrate was concentrated under vacuum. The residue was used directly for the next step.

Compound 4: The above residue was mixed with acetonitrile (2 mL), DIEA (0.25 mL, 1.37 mmol) and bromoethylacetate (0.15 mL, 1.37 mmol). The solution was refluxed under argon for 24 h and then cooled down to RT. Toluene (20 mL) was added to precipitate the DIEA salt. After filtering off the precipitation, the filtrate was purified on flash chromotography ($CH_2Cl_2$/MeOH, 20:1) and 0.15 g of product (61% for 2 steps) was obtained. MS (Electrospray) m/z (M+H)⁺, calcd 737 ($C_{36}H_{53}O_{14}N_2$), obsd 737.6, 759.4 (M+Na)⁺. ¹H-NMR (CDCl₃): 1.25(t, 12H, $CH_3$), 2.08(m, 4H, $CH_2CH_2CH_2$), 3.9(m, 4H, $CH_2OH$), 4.05–4.4(m, 24H), 6.62(m, 4H, aromatic H), 7.0(m, 2H, aromatic H).

Compound 5: Compound 4 (245 ma, 0.33 mmol), triphenylphosphine (262 ma, 1 mmol) and carbon tetrabromide (332 ma, 1 mmol) were dissolved in diethyl ether (3 mL). After stirring at RT for 40 min, flash chromatography ($CH_2Cl_2$ to $CH_2Cl_2$/MeOH, 20:1) purification gave 0.19 g of product (67%). ¹H-NMR (CDCl₃): 1.21(t, 12H, $CH_3$), 2.34(m, 4H, $CH_2CH_2CH_2$), 3.67(t, 4H, $CH_2Br$), 4.05–4.34 (m, 24H), 6.62(m, 4H, aromatic H), 7.0(m, 2H, aromatic H).

Compound 6: Compound 5 (42 ma, 49 μmol) was reacted with cyclen (43 ma, 0.25 mmol) in $CHCl_3$ (0.5 mL) for 30 hours. Flash chromatography ($CHCl_3$/MeOH/$NH_3$ $H_2O$ 12:4:1) afforded the product as a clear glass (41 ma, 80%). MS (Electrospray) m/z (M+H)⁺, calcd 1046 ($C_{52}H_{89}O_2N_{10}$), obsd 1046.0(M+H)⁺, 1067.8(M+Na)⁺, 1089.8(M+2Na—H)⁺, 523.4(M+2H)²⁺, 534.4(M+H+Na)²⁺, ¹H-NMR (CDCl₃): 1.2(t, 12H, $CH_3$), 2.0(br, 4H, $CH_2CH_2CH_2$), 2.6–2.85(br. 36H), 4.0–4.4(br, 24H), 6.64(br, 4H. aromatic H), 6.95(br, 2H, aromatic H).

Compound 7: Compound 6 (38 ma, 38 umol) was mixed with bromoacetic acid (37 ma, 266 μmol) in $H_2O$ (0.2 mL). Sodium hydroxide (SN) was slowly added to keep the pH of the solution above 10. When the pH of the solution reached stable, the reaction was quenched with small amount of acetic acid. The product was purified by reverse phase chromatography (LiChroprep RP-18, $CH_3CN/H_2O$, 5%–50%) and 38 mg (82%) of white powder was obtained after lyophilization. MS (Electrospray) m/z (M+H)⁺, calcd 1280 ($C_{56}H_{83}N_{10}O_{24}$), obsd 1279.4(M—H)⁻, 639.3(M—2H)²⁻. ¹H-NMR (D₂O): 2.32(br, 4H, $CH_2CH_2CH_2$), 3.05–3.83(br, 48H), 4.05(s, 8H), 4.27(br, 4H), 4.7(s, 4H), 6.8(d, 2H, aromatic H), 6.95(d, 2H, aromatic H), 7.4(t, 2H, aromatic H)

Gd³⁺-complex of compound 7: The above ligand (compound 6, 16.5 ma, 12.9 μmol) was dissolved in $H_2O$ (0.5 mL) containing GdCl3 (10.6 ma, 28.4 μmol). NaOH (1N) was slowly added to keep the pH around 5–6. The pH of the solution reached stable within 2 h indicating the completion of the reaction. The mixture was passed through a column packed with the Chelex resin (Biorad, Chelex 100, Na⁺ form) and the fractions containing the product were further purified by reverse phase chromatography (LiChroprep RP-18, $CH_3CN/H_2O$, 5%–50%). The final product was obtained as a white powder (17 ma, 81%). MS (Electrospray) m/z (M+H)⁺: calcd 1583–1597 ($C_{56}H_{78}N_{10}O_{24}Gd_2$, 1590 highest abundance). obsd (the peak of the highest abundance) 1611.4 (M—2H+Na)⁻, 1633.2(M3H+2Na)⁻, 804.8(M—3H+Na)²⁻, 793.6(M—2H)²⁻.

The effect of Ca2⁺ on the relaxivity of the complex

In the presence of Ca²⁺, R=5.53 mM⁻¹ sec⁻¹

In the absence of Ca²⁺, R=3.03 mM⁻¹ sec⁻¹

The effect of pH on the relaxivity of the complex

The T1 of the Gd³⁺-complex (0.4 mM in the buffer containing 100 mM KCl, 10 mM MOPS, 2 mM $K_2H_2EGTA$ or 2 mM $K_2CaEGTA$) was measured under different pH. Changing pH from 6.80 to 7.40 in 0.2 pH unit steps had minimum effects on the relaxivity of the complex, either in the presence or in the absence of Ca²⁺.

| pH | 6.80 | 7.00 | 7.20 | 7.40 |
|---|---|---|---|---|
| T1 (msec, $K_2H_2EGTA$) | 600 | 605 | 604 | 608 |
| T1 (msec, $K_2CaEGTA$) | 390 | 393 | 394 | 397 |

The effect of Mg²⁺ on the relaxivity of the complex

The T1 of the Gd³⁺-complex (0.4 mM in the buffer containing 132 mM KCl, 10 mM MOPS, 1 mM $K_2H_2EGTA$, pH 7.20) was measured. Changing Mg²⁺ concentration from 0 to 20 mM had minimum effects on the relaxivity of the complex.

| Mg²⁺ (mM) | 0 | 1 | 2 | 5 | 10 | 20 |
|---|---|---|---|---|---|---|
| T1 (msec) | 607 | 602 | 601 | 609 | 607 | 610 |

Example 5

MR Imaging of *Xenopus laevis* Embryos

In vivo experiments using EGadMe were carried out in *Xenopus laevis* embryos. To permit an independent tracking of which cells were descendants of the β-gal injected cell, mRNA for nuclearly localized GFP (nGFP) was co-injected. Since the first mitosis approximately defines the plane dividing the future left and right sides of the embryo, these injections introduce EGadMe to both sides of the embryo; while β-galactosidase and nGFP will only be expressed in a subset of the cells located primarily on one side of the animal. Therefore, each embryo will contain cells in which EGadMe is expected to be enzymatically processed and other cells with unprocessed contrast agent.

Synthetic mRNA was transcribed using the SP6 mMessage Machine Kit (Ambion, Austin, Tex.) according to the manufacturer's protocol. Embryos at the 2-cell stage in 1×Marc's Modified Ringer's Solution (MMR) were injected with 4 nL of 400 mM EGadMe to both cells. One cell was injected with either 4 nL 0.5 μg/μl β-galactosidase mRNA, 0.025 μg/μl nGFP mRNA, or water. This yields approximately 13,000 copies of the 3,000 bp sequence per cell in the 100,000 cells stage animal, this is in the range of a high copy endogenous gene. The bolus volume was controlled using a pulsed constant-pressure picoinjector system (PLI-100, Medical Systems, Greenvale, N.Y.). Additional embryos were injected with water alone as a control for viability of the given batch of embryos. Embryos were incubated at 16° C. following injections. Twenty minutes to one hour after injection, embryos were moved to 0.1×MMR. After gastrulation the embryos were moved to room temperature for 24 hours prior to imaging.

Images were acquired using a Bruker AMX500 (Bruker Instruments, Billerica, Mass.) microimaging system with a wide-bore (89 mm) 11.7 T magnet and a laboratory-built solenoid imaging probe. Multiple embryos were imaged simultaneously in a 2.5 mm diameter quartz tube containing 0.1×MMR solution. In order to minimize embryo movement during imaging, MS-222 anaesthestic was added to a final concentration of 0.01% (Finquel, Argent, Redmond, Wash.) and the embryos were maintained at 15° C. A 3D spin-echo sequence was used to acquire images with $T_R/T_E$=400/21 ms, 512×128×128 image points, and a field of view of 1.4×0.4×0.4 cm (acquisition time=3 hours 45 minutes). The data was zero-filled to 512×256×256 points before Fourier Transformation yielding a final voxel size of 27×16×16 μm.

Images were processed using VoxelView (Vital Images. Inc., Minneapolis, Minn.) on a Silicon Graphics O2 workstation. To make water transparent, the opacity was adjusted to zero for those voxels with the signal intensity expected of Ringer's solution (region surrounding the embryos).

β-galactosidase images were obtained on embryos fixed for 15 minutes in 250 mM Na cacodylate, 1% glutaraldehyde, and washed for 5 minutes with CMAP [7.2 mM $Na_2HPO_4$, 2.8 mM $NaH_2PO_4$, 150 mM NaCl, 1 mM $MgCl_2$, 3 mM $K_3Fe(CN)6$, 3 mM $K_4Fe(CN)_6$ $3H_2O$], followed by staining for 60 minutes at 37° C. in 0.027% X-gal and 0.1% Triton X-100. Embryos were photographed using a Zeiss Stemi SV 11 equipped with a Prog/Res/3012 camera (Kontron Elektronik, Eching, Germany) controlled by a Roche Image Analysis System and processed with Photoshop 4.0 (Adobe, San Jose, Calif.).

Fluorescence images were obtained with a Zeiss Axioplan epifluorescence microscope (5x magnification) equipped with a Hammamatsu C2400 SIT camera, and an image processor (Imaging Technology 151, Bedford, Mass.) controlled by the Vidlm software package (Belford, Stollberg, and Fraser, unpublished data) using boxcar averaging of 16 frames. Acquired images were rendered using Photoshop 4.0 (Adobe, San Jose, Calif.).

Images of the embryos (collected using a three-dimensional, spin-echo, $T_1$-weighted pulse sequence) revealed the expected increase in the signal intensity for those regions of the embryo containing the mRNA for β-galactosidase (FIG. 17). This increase depends on the presence of EGadMe; embryos injected with mRNA alone (no contrast agent) resembled those injected with water alone. Comparison of the two embryos in FIG. 17 illustrates the significant signal enhancement achieved in those cells with both EgadMe and β-galactosidase.

The difference between the cleaved and uncleaved states of EGadMe is clearly demonstrated by comparing regions within a single embryo. FIG. 18 compares the dorsal views of a living embryo by fluorescence (nGFP; FIG. 18A) and MRI (FIG. 18B). The embryo was subsequently fixed and stained for β-gal activity (FIG. 18C). More intense signal is evident on the right side of the embryo by all techniques and there is a good correlation between the regions showing nGFP-fluoresence, X-gal staining for β-galactosidase, and regions of intense signal in the MR image. The MRI shows both the region of heavy labeling on the right side of the embryo and a region of sparse labeling on the left side that are confirmed in the β-galactosidase staining of the fixed embryo (FIG. 18C). Autofluorescence in the embryo and the limited depth of penetration by light microscopy make it difficult to perform a point to point comparision between the nGFP-fluoresence, the β-galactosidase labeling, and the 3D MR images. There is a 57% enhancement of MRI signal intensity in the somites expressing β-galactosidase compared to the equivalent somites not expressing β-galactosidase (signal intensity is approximately 10–15 times the noise level in the image).

These results document the ability of EGadMe to render three-dimensional images of marker expression. The present results emphasize that EgadMe does not serve merely as a lineage tracer but is sensitive to beta-galactose activity.

Example 6

MRI Detection of Gene Expression in *Xenopus laevis* Embryos

To test the ability of this approach to detect in vivo gene expression (i.e. transcription and translation), both cells of Xenopus embryos at the two cell stage were injected with EgadMe and then one of the blastomeres was injected with a DNA construct carrying the lacZ gene. Comparison of the MR image for a live embryo (FIG. 19A) with the image of the same embryo after fixation and staining for β-galactosidase activity (FIG. 19B) shows good correlation between areas of intense MRI signal and those staining positive for the enzyme after fixation. Both images show strong labeling in the stripe of endoderm running the length the embryo and in two dinstinct spots located ventral to the cement gland (arrows). Both techniques also detect β-galactosidase expression in the eye, regions of the head, and ventral regions.

Expression of injected DNA is known to be mosaic; injected DNA is not expressed in every cell in which it is introduced. Therefore, these results emphasize that EgadMe does not serve merely as an inert lineage tracer but is sensitive to gene expression. Furthermore, these images demonstrate the advantages of MRI for visualizing deep tissue. These data demonstrate that MR imaging with EGadMe offers both the contrast and spatial resolution to clearly detect positive domains at cellular resolution in living animals.

We claim:

1. A composition comprising:

a) a polymer;

b) at least one MRI agent comprising:

i) at least one chelator comprising a paramagnetic metal ion; and, ii) a PMALWMR peptide blocking moiety (SEQ ID NO: 11) covalently attached to said chelator, such that upon interaction of said PMALWMR peptide blocking moiety with a target substance, the $T_1$ of said MRI agent is decreased; and c) a linker group attaching said MRI agent to said polymer.

2. An MRI agent according to claim 1 having the formula comprising:

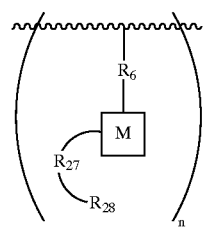

wherein $\sim\!\!\sim\!\!\sim$ is a polymer

M is a chelator comprising a paramagnetic metal ion;

$R_{26}$ and $R_{27}$ are linker groups;

$R_{28}$ is a PMALWMR peptide blocking moiety (SEQ ID NO: 11); and, n is an integer.

3. An MRI agent according to claim 1 having the formula comprising:

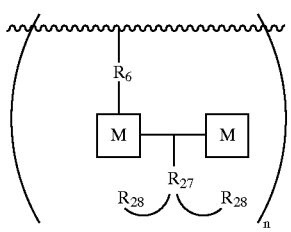

wherein $\sim\!\!\sim\!\!\sim$ is a polymer;

M is a chelator comprising a paramagnetic metal ion;

$R_{26}$ and $R_{27}$ are linker groups;

$R_{28}$ is a PMALWMR peptide blocking moiety (SEQ ID NO: 11); and n is an integer.

4. An MRI agent according to claims 1, 2, or 3 wherein said paramagnetic metal ion is selected from the group comprising gadolinium III (Gd+3 or Gd(III)), iron III(Fe+3 or Fe(III)), manganese II (Mn+2 or Mn(II)), dysprosium (Dy+3 or Dy(III)), or chromium (Cr+3 or Cr(III).

5. An MRI agent according to claim 4 where said paramagnetic ion is Gd(III).

6. An MRI agent according to claims 1, 2, or 3 wherein said linker groups are alkyl groups.

7. An MRI agent according to claim 6 wherein said alkyl groups are substituted alkyl groups.

8. An MRI agent according to claims 1, 2, or 3 wherein said linker groups are aryl groups.

9. An MRI agent according to claim 8 wherein said aryl groups are substituted aryl groups.

10. An MRI agent according to claims 1, 2, or 3 wherein at least one of said linker groups are selected from the group comprising p-aminobenzyl, methyl, ethyl, propyl, butyl, pentyl, hexyl, propionic acid, aminobutyl, p-alkyl phenols, and 4-alkylimidazaole.

11. An MRI agent according to claims 1, 2, or 3 wherein said PMALWMR peptide blocking moiety (SEQ ID NO: 11) binds to a metalloproteinase.

12. An MRI agent according to claims 1, 2, or 3 wherein said polymer is selected from the group comprising functionalized dextrans, styrene polymers, polyethylene, polyanionic polymers, polycationic polymers, and mixed polymers.

13. An MRI agent according to claim 12 wherein said polycation is polylysine.

14. An MRI agent according to claims 1, 2, or 3 wherein said polymer comprises a plurality of said MRI agents.

15. A method of magnetic resonance imaging of a cell, tissue or patient comprising administering an MRI agent according to claims 1, 2, or 3 to a cell, tissue or patient and rendering a magnetic resonance image of said cell, tissue or patient.

16. An MRI agent according to claims 1, 2, or 3 wherein

∿∿∿ is a dextran polymer;

M is a DOTA chelator comprising a Gd(III) paramagnetic metal ion;

$R_{26}$ and $R_{27}$ are alkyl linker groups;

$R_{28}$ is the peptide blocking moiety PMALWMR (SEQ ID NO: 11); and, n is an integer.

* * * * *

UNITED STATES PATENT AND TRADEMARK OFFICE
CERTIFICATE OF CORRECTION

PATENT NO. : 6,770,261 B2
DATED : August 3, 2004
INVENTOR(S) : Meade et al.

It is certified that error appears in the above-identified patent and that said Letters Patent is hereby corrected as shown below:

Column 1,
Line 19, please insert heading immediately preceding the heading "FIELD OF THE INVENTION":

-- STATEMENT AS TO FEDERALLY SPONSORED RESEARCH
This invention was made with government support under Grant Number AR-42671, awarded by the National Institutes of Health. The Government has certain rights to this invention. --

Signed and Sealed this

Twenty-eighth Day of December, 2004

JON W. DUDAS
*Director of the United States Patent and Trademark Office*